(12) United States Patent
Cole et al.

(10) Patent No.: US 8,435,289 B2
(45) Date of Patent: May 7, 2013

(54) RAPID EXCHANGE IOL INSERTION APPARATUS AND METHODS OF USING

(75) Inventors: Mark S. Cole, Trabuco Canyon, CA (US); Rod T. Peterson, Tustin Ranch, CA (US); Nicholas E. Martin, Laguna Hills, CA (US); Steven R. Anderson, Rancho Santa Margarita, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 864 days.

(21) Appl. No.: 11/779,230

(22) Filed: Jul. 17, 2007

(65) Prior Publication Data

US 2008/0058830 A1     Mar. 6, 2008

Related U.S. Application Data

(63) Continuation-in-part of application No. 11/627,931, filed on Jan. 26, 2007, which is a continuation-in-part of application No. 11/056,501, filed on Feb. 11, 2005.

(60) Provisional application No. 60/762,918, filed on Jan. 26, 2006.

(51) Int. Cl.
*A61F 2/16*     (2006.01)
*A61F 9/00*     (2006.01)

(52) U.S. Cl.
USPC .......................................... 623/6.12; 606/107

(58) Field of Classification Search ................. 623/6.12, 623/6.11; 606/107, 166
See application file for complete search history.

(56) References Cited

U.S. PATENT DOCUMENTS

| | | | |
|---|---|---|---|
| 4,205,747 A | 6/1980 | Gilliam et al. |
| 4,862,885 A | 9/1989 | Cumming |
| 5,275,604 A | 1/1994 | Rheinish et al. |
| 5,281,227 A | 1/1994 | Sussman |
| 5,304,182 A | 4/1994 | Rheinish et al. |

(Continued)

FOREIGN PATENT DOCUMENTS

| | | |
|---|---|---|
| BE | 1016692 A3 | 4/2007 |
| EP | 270257 A1 | 6/1988 |

(Continued)

*Primary Examiner* — Kathleen Holwerda
*Assistant Examiner* — Jocelin Tanner
(74) *Attorney, Agent, or Firm* — Abbott Medical Optics Inc.

(57) ABSTRACT

A system for easily transferring an intraocular lens (IOL) from a lens case to an inserter, and then into a patient's eye. The lens case has a transfer mechanism therein which retains the IOL until engagement with the inserter. The transfer mechanism may include jaws having a closed configuration for retaining the IOL and an open configuration for releasing the IOL. Engagement of the inserter with the lens case automatically opens the jaws and transfers the IOL to the inserter. The IOL is transferred into a load chamber of a nosepiece rotatably coupled to a handpiece. After transfer of the IOL, the nosepiece is rotated from a load position to a delivery position. The IOL may have an optic and a haptic coupled to the optic, and the lens case may be capable of configuring the haptic as desired to facilitate its transfer into an inserter and/or into the eye. For instance, the lens case may fold one or both of the haptics over the optic. Preferably, the lens case maintains the haptic in this position during transfer of the intraocular lens into an inserter and/or inserter cartridge. A manifold for easily distributing a viscoelastic medium to the load chamber of the inserter is also provided.

7 Claims, 33 Drawing Sheets

U.S. PATENT DOCUMENTS

| | | | |
|---|---|---|---|
| 5,425,734 A | 6/1995 | Blake | |
| 5,468,246 A | 11/1995 | Blake | |
| 5,616,148 A | 4/1997 | Eagles et al. | |
| 5,620,450 A | 4/1997 | Eagles et al. | |
| 5,728,102 A | 3/1998 | Feingold et al. | |
| 5,772,666 A | 6/1998 | Feingold et al. | |
| 5,807,400 A | 9/1998 | Chambers et al. | |
| 5,860,984 A | 1/1999 | Chambers et al. | |
| 5,902,307 A | 5/1999 | Feingold et al. | |
| 6,010,510 A | 1/2000 | Brown et al. | |
| 6,048,347 A | 4/2000 | Erdman | |
| 6,056,757 A | 5/2000 | Feingold et al. | |
| 6,143,000 A | 11/2000 | Feingold | |
| 6,162,229 A | 12/2000 | Feingold et al. | |
| 6,174,315 B1 | 1/2001 | Chambers et al. | |
| 6,203,549 B1 | 3/2001 | Waldock | |
| 6,214,015 B1 | 4/2001 | Reich et al. | |
| 6,228,094 B1 | 5/2001 | Erdman | |
| 6,241,737 B1 | 6/2001 | Feingold | |
| 6,248,170 B1 | 6/2001 | Sirejacob | |
| 6,336,932 B1 | 1/2002 | Figueroa et al. | |
| 6,371,960 B2 | 4/2002 | Heyman et al. | |
| 6,386,357 B1* | 5/2002 | Egawa | 206/5.1 |
| 6,387,101 B1 | 5/2002 | Butts et al. | |
| 6,406,481 B2 | 6/2002 | Feingold et al. | |
| 6,468,282 B2 | 10/2002 | Kikuchi et al. | |
| 6,471,708 B2 | 10/2002 | Green | |
| 6,491,697 B1 | 12/2002 | Clark et al. | |
| 6,506,195 B2 | 1/2003 | Chambers et al. | |
| 6,537,283 B2 | 3/2003 | Van Noy | |
| 6,558,395 B2 | 5/2003 | Hjertman et al. | |
| 6,685,740 B2 | 2/2004 | Figueroa et al. | |
| 6,712,848 B1 | 3/2004 | Wolf et al. | |
| 7,156,854 B2 | 1/2007 | Brown et al. | |
| 7,476,230 B2 | 1/2009 | Ohno et al. | |
| 7,754,953 B2 | 7/2010 | Takegawa | |
| 2001/0001822 A1 | 5/2001 | Chambers et al. | |
| 2001/0015593 A1 | 8/2001 | Polla et al. | |
| 2001/0041897 A1 | 11/2001 | Feingold et al. | |
| 2002/0022881 A1 | 2/2002 | Figueroa et al. | |
| 2002/0077633 A1* | 6/2002 | Kikuchi et al. | 606/107 |
| 2002/0082609 A1 | 6/2002 | Green | |
| 2002/0151904 A1 | 10/2002 | Feingold et al. | |
| 2002/0193805 A1 | 12/2002 | Ott et al. | |
| 2003/0036765 A1 | 2/2003 | Van Noy | |
| 2003/0045930 A1 | 3/2003 | Nguyen | |
| 2003/0050646 A1 | 3/2003 | Kikuchi et al. | |
| 2003/0212406 A1 | 11/2003 | Kobayashi et al. | |
| 2003/0212409 A1 | 11/2003 | Kobayashi et al. | |
| 2004/0127911 A1 | 7/2004 | Figueroa et al. | |
| 2004/0193121 A1 | 9/2004 | Kadziauskas | |
| 2004/0243141 A1 | 12/2004 | Brown et al. | |
| 2004/0267359 A1 | 12/2004 | Makker et al. | |
| 2005/0125000 A1 | 6/2005 | Tourrette et al. | |
| 2006/0085013 A1 | 4/2006 | Dusek et al. | |
| 2006/0149315 A1 | 7/2006 | Kebel et al. | |
| 2007/0060925 A1* | 3/2007 | Pynson | 606/107 |
| 2008/0097459 A1 | 4/2008 | Kammerlander et al. | |
| 2008/0114313 A1 | 5/2008 | Gomez et al. | |
| 2009/0125034 A1* | 5/2009 | Pynson | 606/107 |
| 2010/0217273 A1 | 8/2010 | Someya et al. | |
| 2010/0228260 A1 | 9/2010 | Callahan et al. | |
| 2010/0278261 A1 | 11/2010 | Chujoh et al. | |
| 2012/0022549 A1 | 1/2012 | Someya et al. | |
| 2012/0071887 A1 | 3/2012 | Ichinohe et al. | |

FOREIGN PATENT DOCUMENTS

| | | |
|---|---|---|
| EP | 402138 A1 | 12/1990 |
| EP | 467814 A1 | 1/1992 |
| EP | 1338254 A1 | 8/2003 |
| EP | 1421917 A2 | 5/2004 |
| EP | 1481652 A1 | 12/2004 |
| EP | 1360944 B1 | 9/2007 |
| EP | 2161005 A1 | 3/2010 |
| EP | 1737393 B1 | 6/2010 |
| EP | 2123239 B1 | 3/2012 |
| FR | 2875126 A1 | 3/2006 |
| JP | 4707016 B2 | 6/2011 |
| WO | 94/22402 | 10/1994 |
| WO | WO9628121 A1 | 9/1996 |
| WO | WO9715253 | 5/1997 |
| WO | WO9933411 A1 | 7/1999 |
| WO | WO9958086 A1 | 11/1999 |
| WO | 01/74427 | 10/2001 |
| WO | WO0187186 A1 | 11/2001 |
| WO | WO0187187 A1 | 11/2001 |
| WO | WO03024356 A2 | 3/2003 |
| WO | WO2004010903 A1 | 2/2004 |
| WO | WO2004045467 A1 | 6/2004 |
| WO | WO2005020853 A2 | 3/2005 |
| WO | WO2005030097 A1 | 4/2005 |
| WO | WO2005070341 A1 | 8/2005 |
| WO | WO2006070219 A1 | 7/2006 |
| WO | 2006/086495 A1 | 8/2006 |
| WO | 2007/028368 A1 | 3/2007 |
| WO | 2007/087641 A2 | 8/2007 |
| WO | WO2008014260 A1 | 1/2008 |
| WO | WO2008060869 A2 | 5/2008 |

* cited by examiner

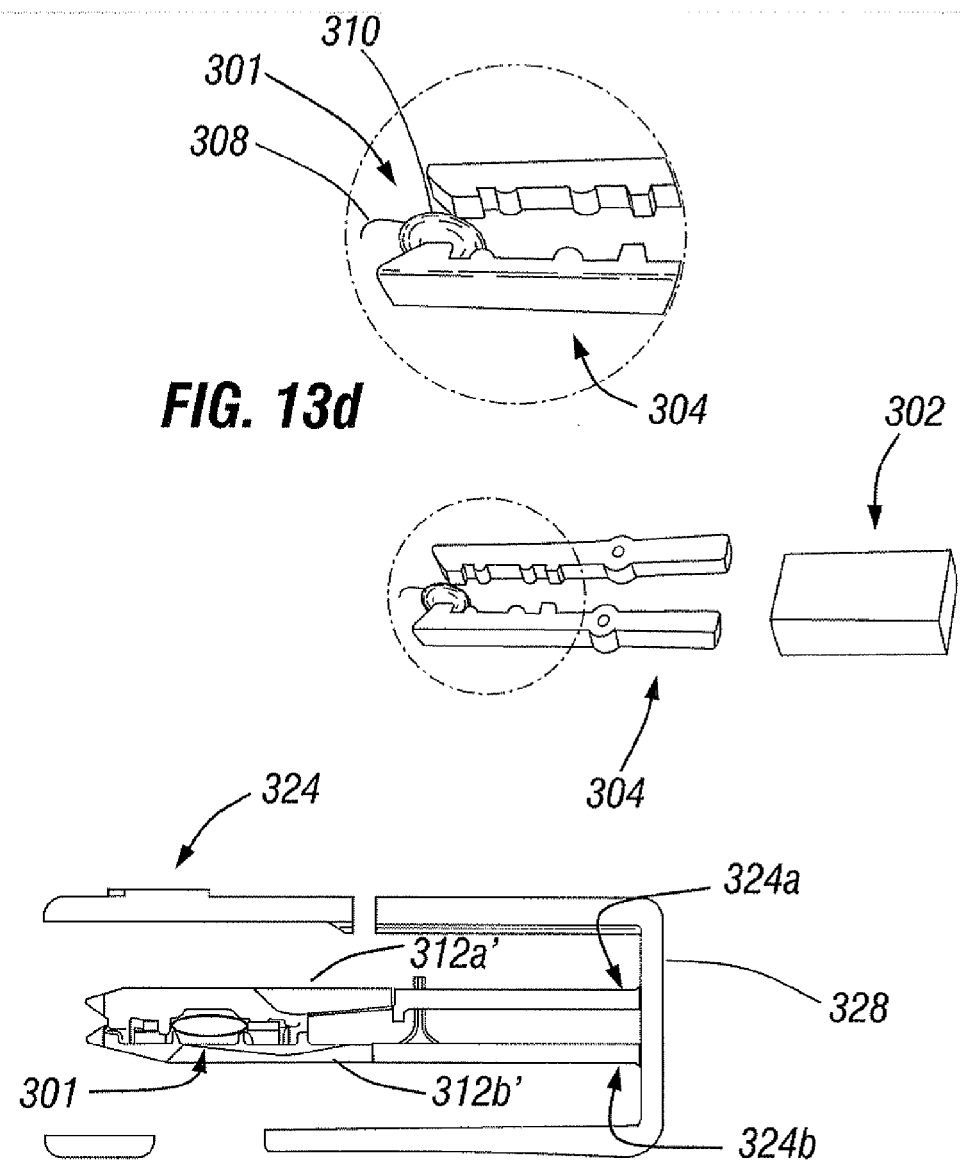
FIG. 13d
FIG. 14a
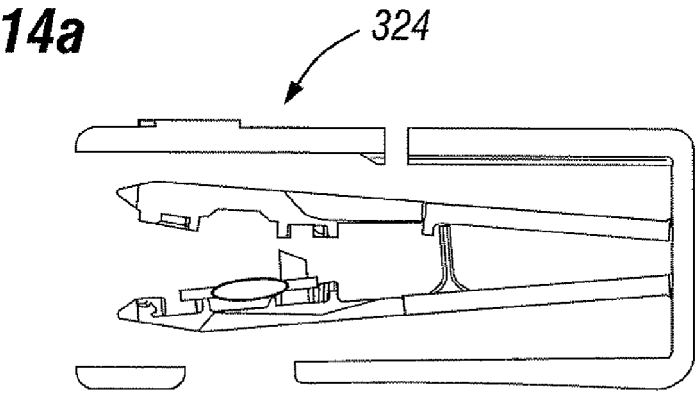
FIG. 14b

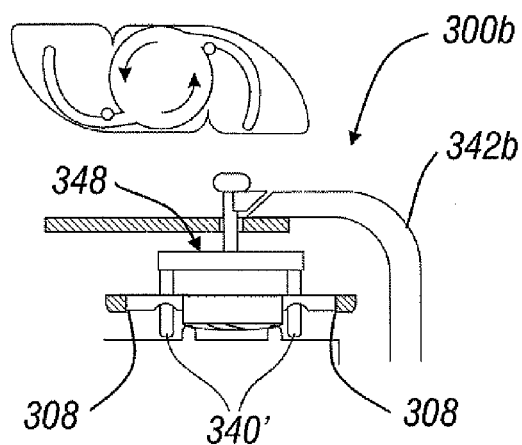
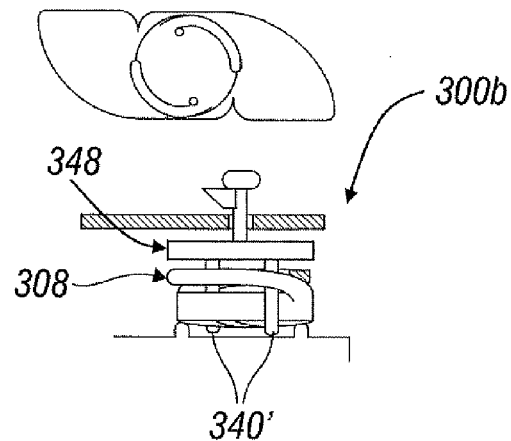
FIG. 18a    FIG. 18b
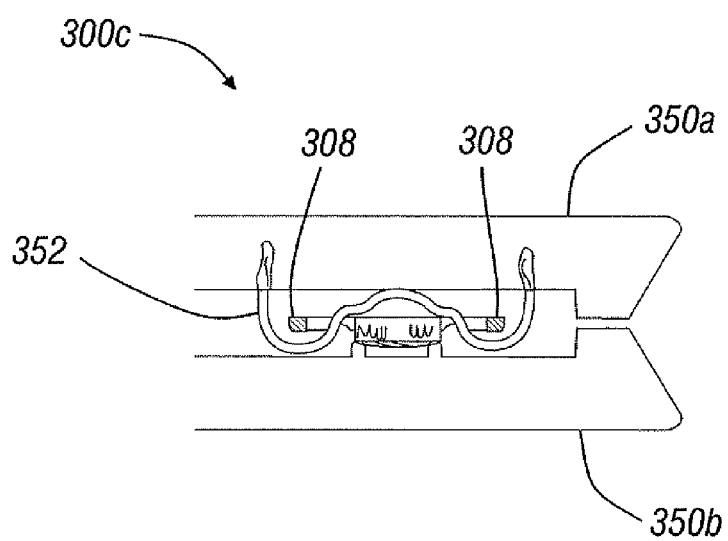
FIG. 19

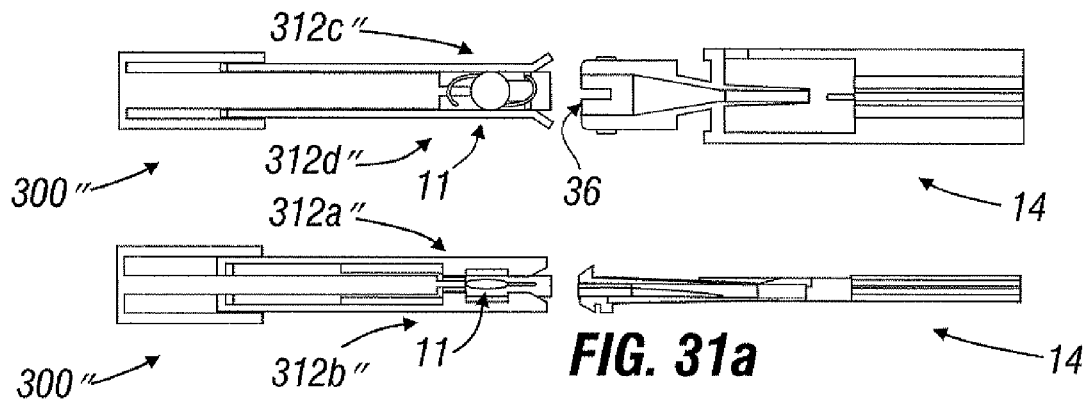
FIG. 31a
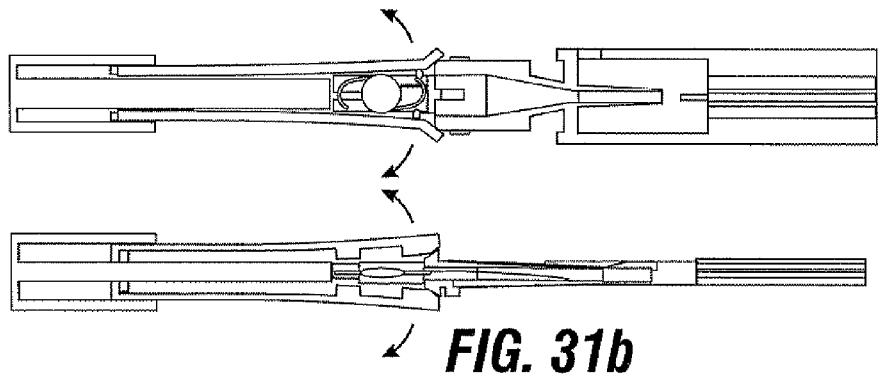
FIG. 31b
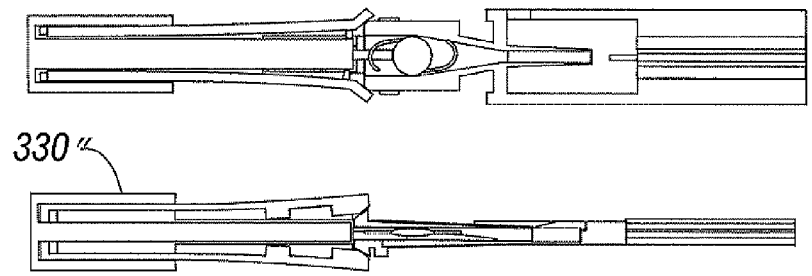
FIG. 31c
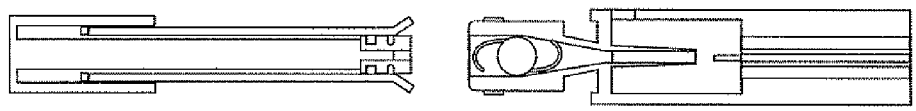
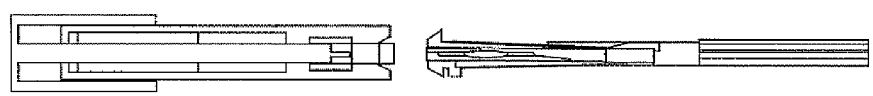
FIG. 31d

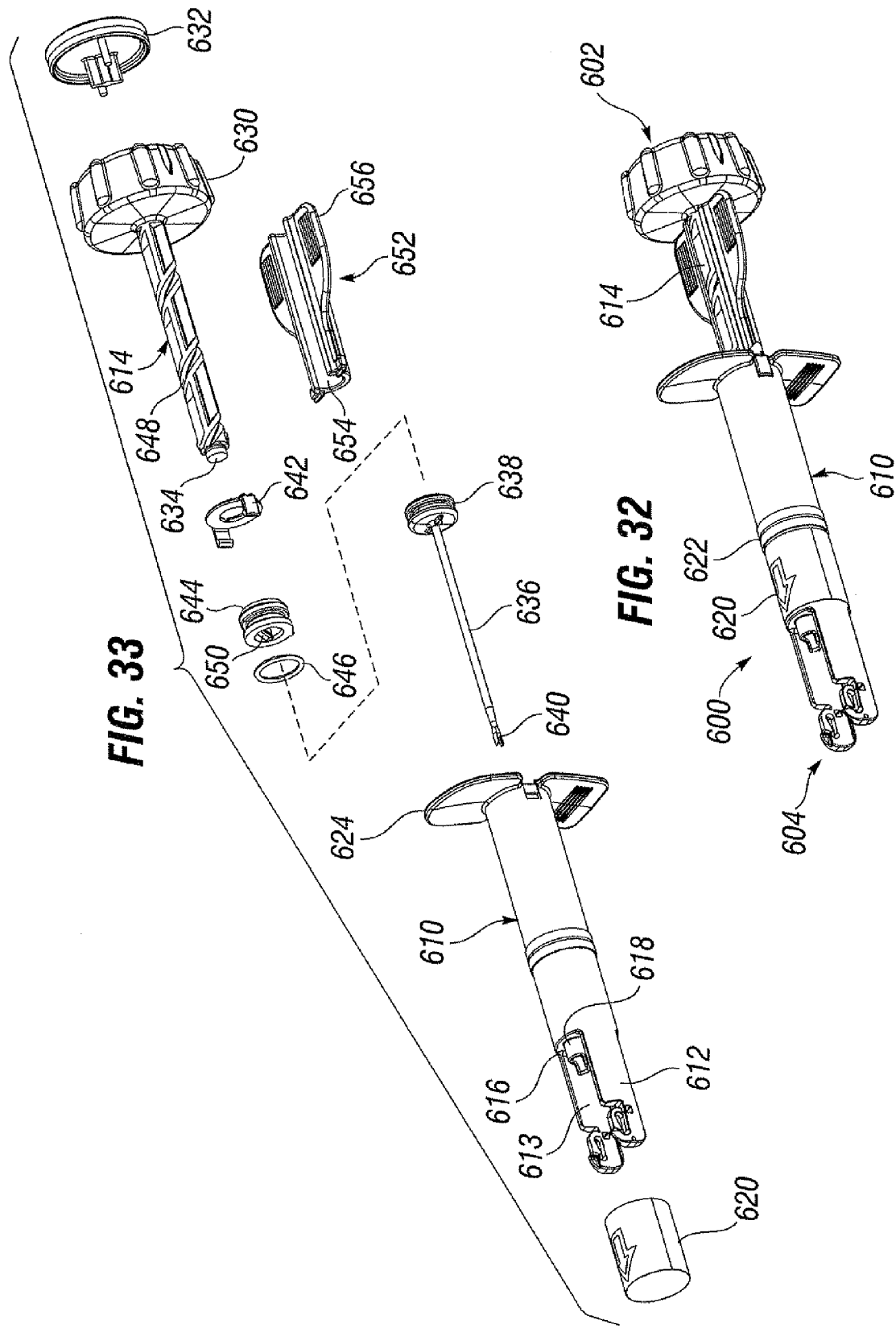

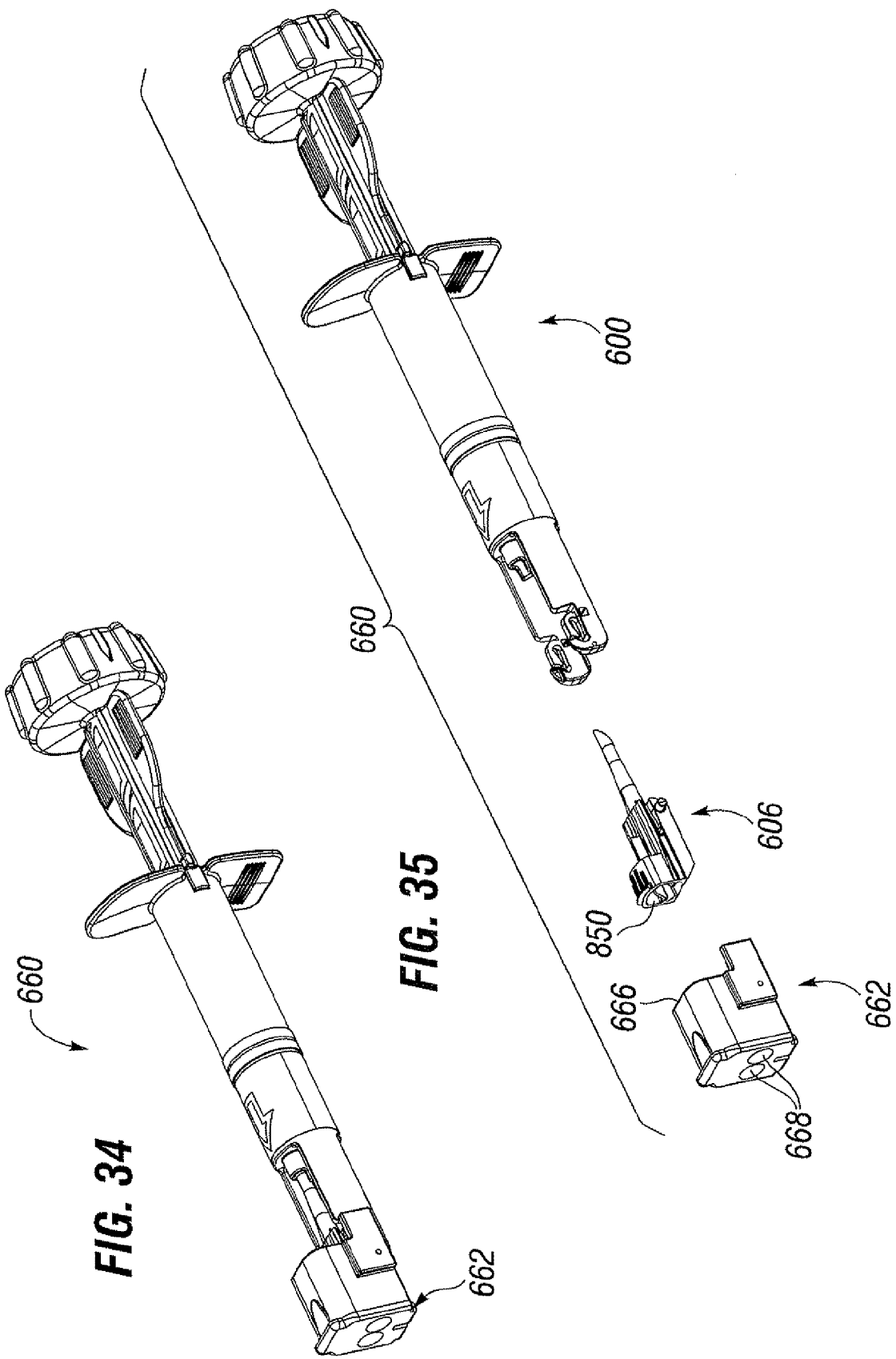

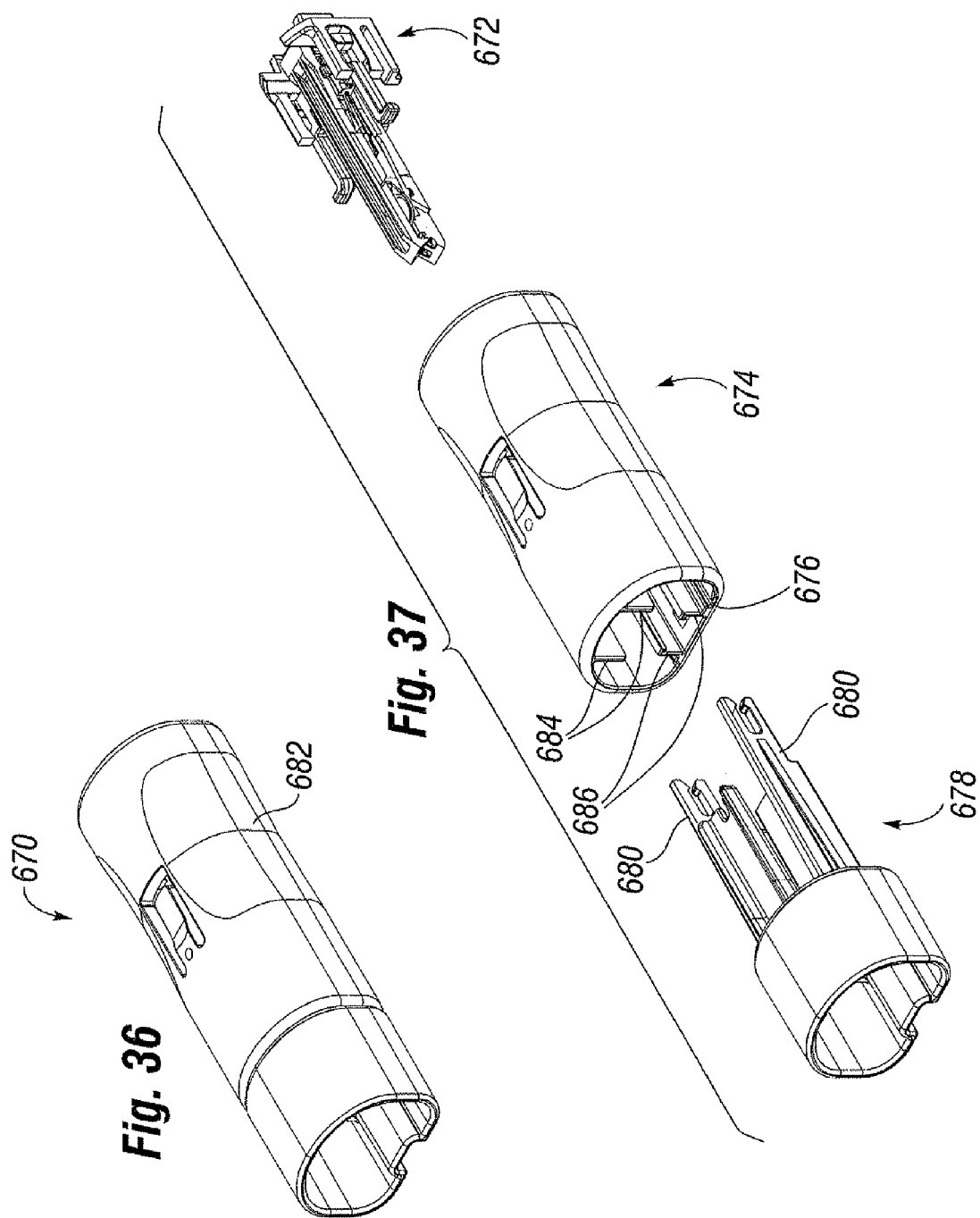

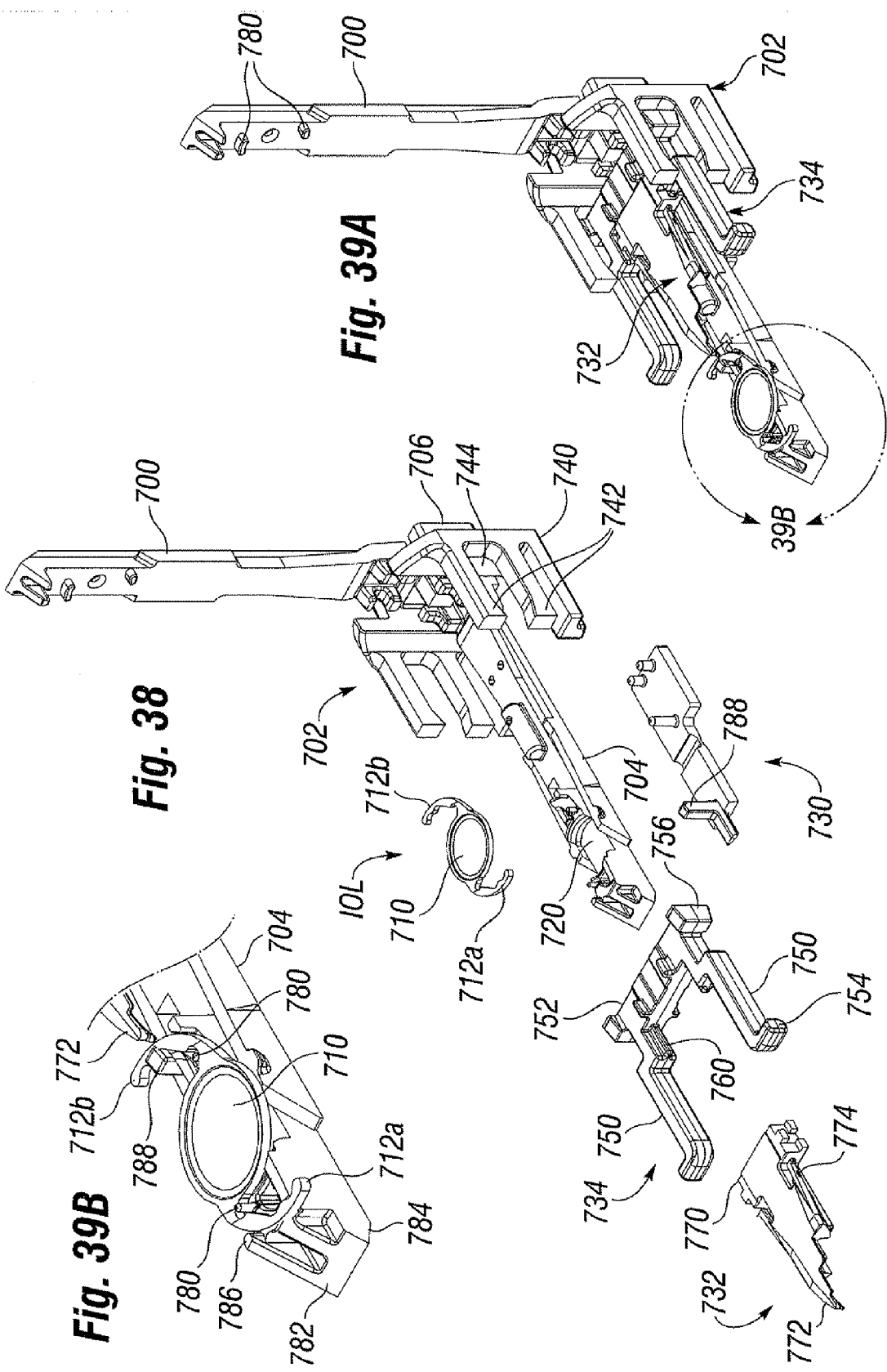

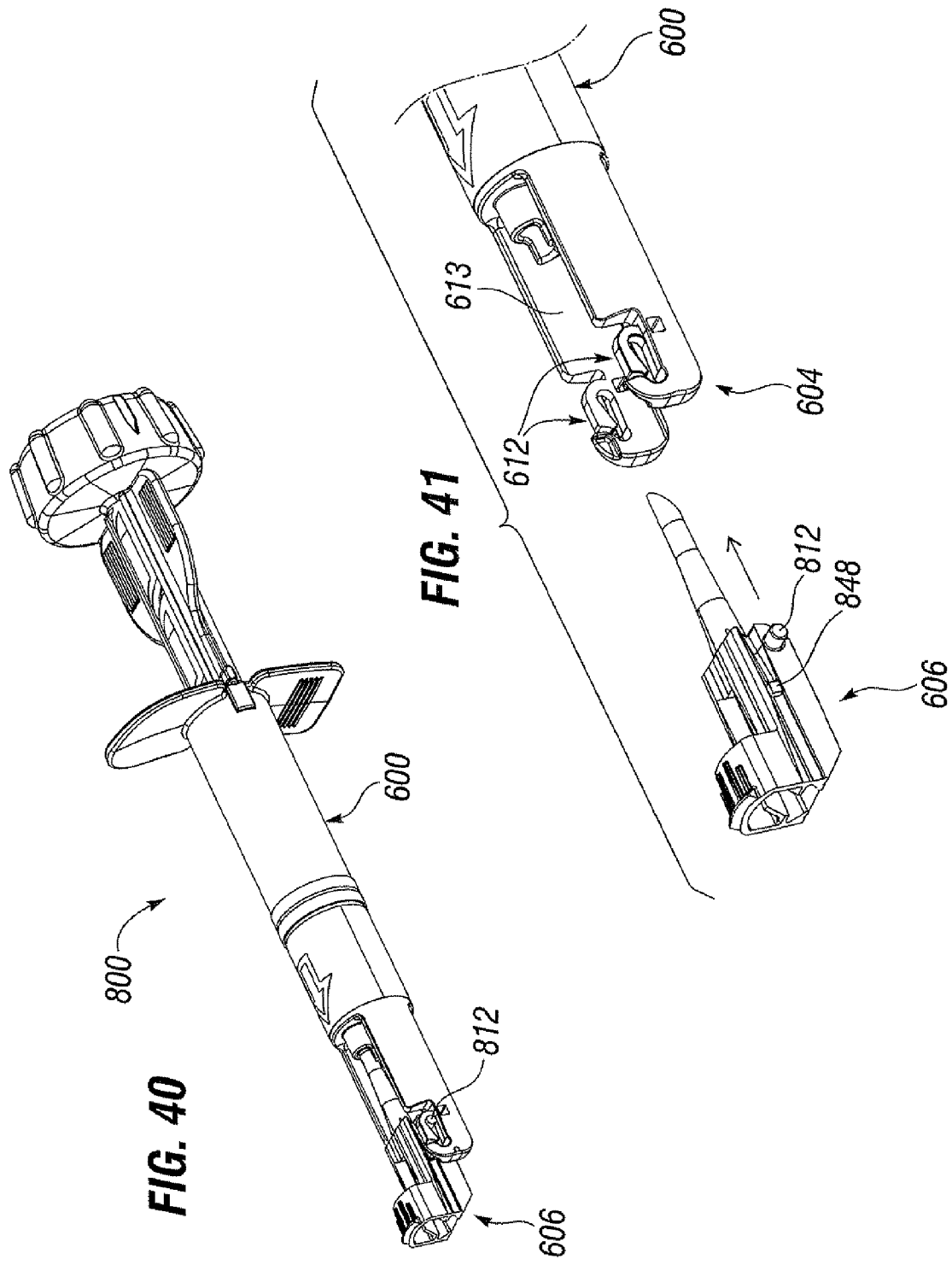

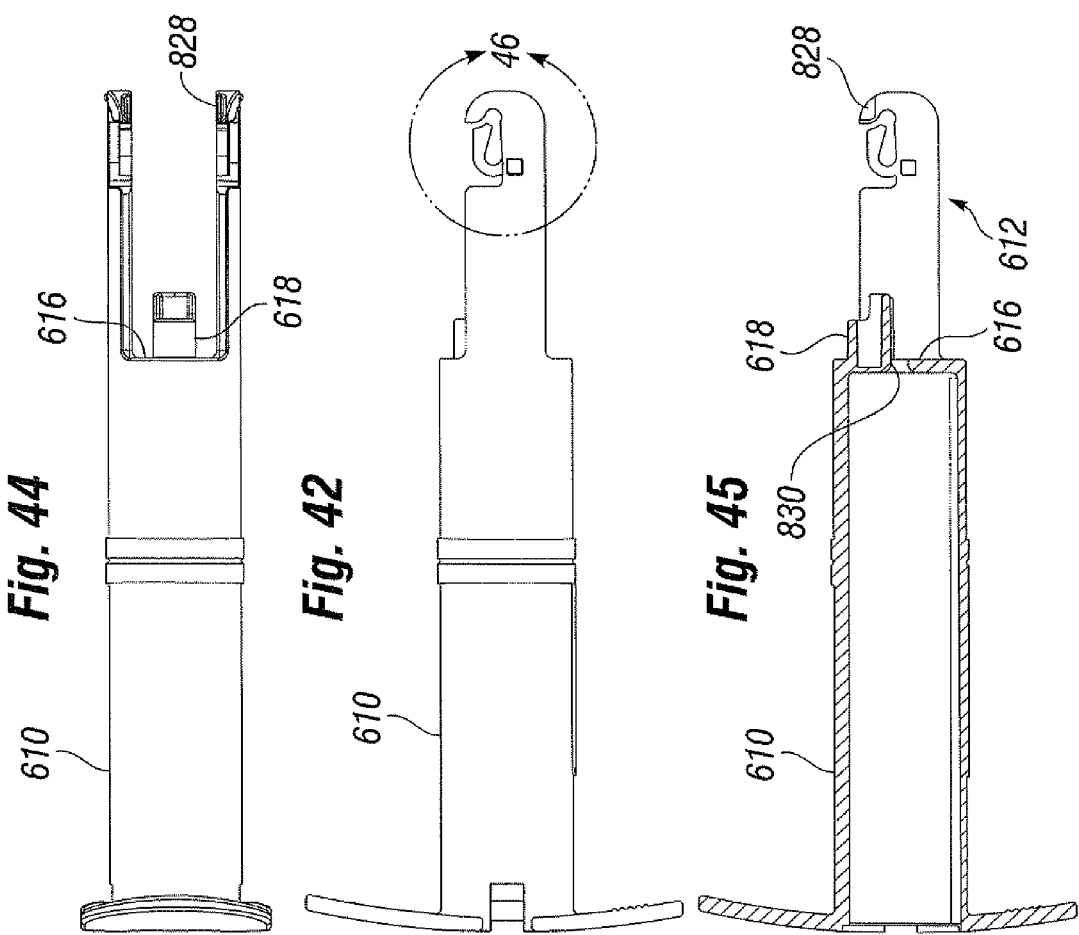

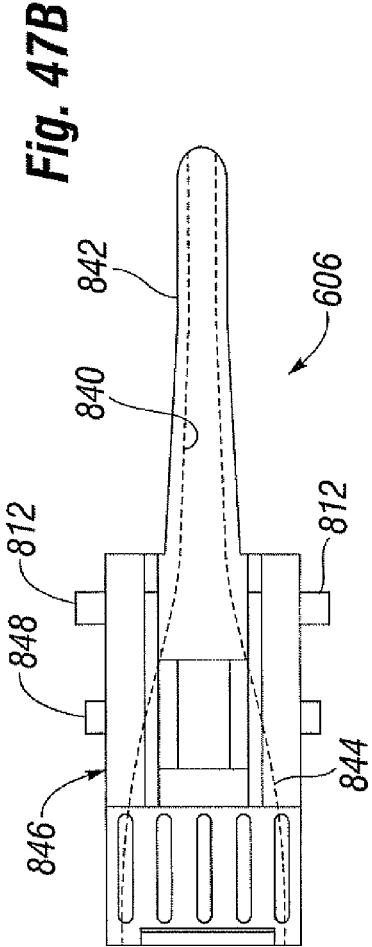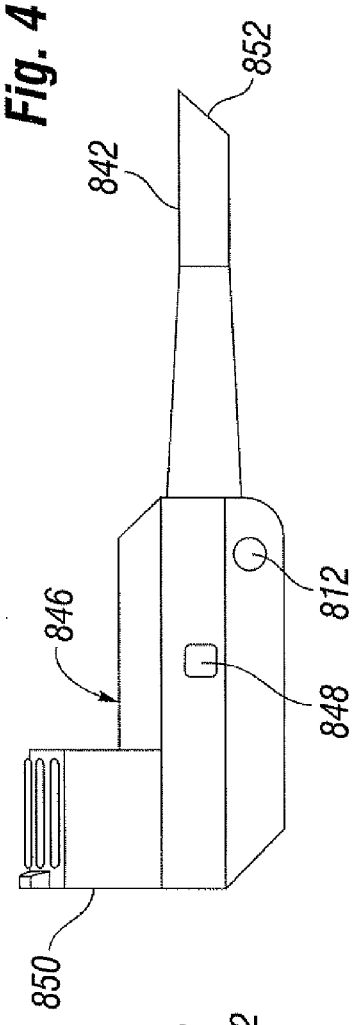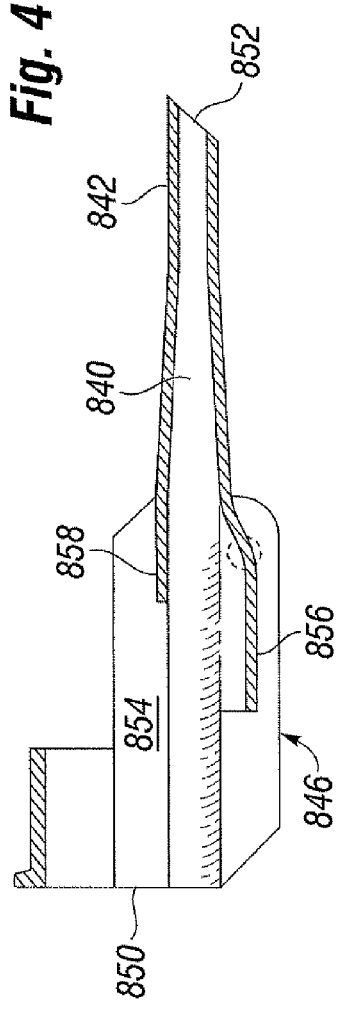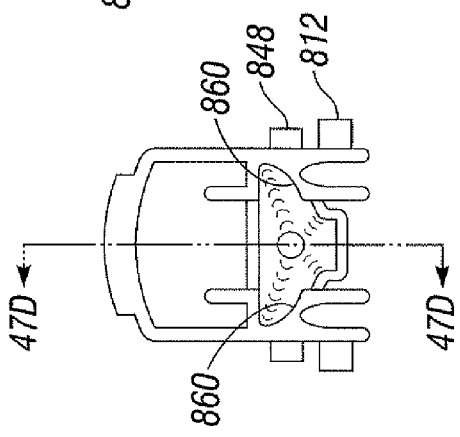

RAPID EXCHANGE IOL INSERTION APPARATUS AND METHODS OF USING

RELATED APPLICATIONS

This application is a continuation-in-part of U.S. application Ser. No. 11/627,931, filed Jan. 26, 2007, which is a continuation-in-part of U.S. application Ser. No. 11/056,501, filed Feb. 11, 2005, and claims priority under 35 U.S.C. §119(e) from U.S. Provisional Application No. 60/762,918, filed Jan. 26, 2006, each of which are incorporated herein by reference in their entireties.

FIELD OF THE INVENTION

The present invention relates to devices, systems, and methods for delivering an intraocular lens into an eye. More particularly, the invention relates to devices, systems, and methods in which the intraocular lens is loaded from the front end of the device.

Intraocular lenses (IOLs) may be implanted in the eye of a subject to replace the natural crystalline lens or to otherwise modify the vision of an eye containing either the natural lens or another IOL. IOLs commonly include an optic and one or more flexible fixation members or haptics extending from the optic to secure and center the optic within the eye. When the IOL replaces the natural lens, the natural lens must first be removed, for instance, using a phacoemulsification system. The IOL is then generally implanted using an insertion apparatus or device that rolls, folds, or otherwise configures the lens for delivery through a small incision in the eye in a way that reduces trauma and expedites post-surgery healing.

Inserters or injectors for delivering IOLs into the eye generally employ a cartridge having a hollow insertion tube or cannula through which the folded IOL is passed using a pushrod. The inserter may be designed for reuse, in which case the inserter components are usually made of some type of metal alloy. Alternatively, disposable inserters may be used that are made of less expensive materials, such as plastics, and that remain in a sterile package until ready for use. The pushrod and insertion tube may be designed to advantageously provide the surgeon precise control of the IOL as it is placed inside the eye, for example as disclosed in U.S. Pat. No. 6,093,193, herein incorporated by reference.

One problem encountered with existing inserters is difficulty in loading the IOL into the inserter. The IOL is typically manually moved from a sterile environment to an inserter or associated cartridge using forceps or tweezers. Manual transfer of the IOL presents difficulties in maintaining both sterility of the IOL and the correct orientation of the IOL within the cartridge or inserter. Improper orientation of the IOL can result in inadequate surgeon control and even damage to the IOL during delivery into the eye.

These problems may be mitigated by preloading the IOL at the manufacturer into a cartridge or container that is designed to attach directly to the inserter during transfer of the IOL. The cartridge or container may be attached to the inserter either at the manufacturer or by the user just prior to surgery. In either case, the IOL is generally not stored directly in the inserter, since it is desirable to maintain the IOL in an unstressed state during storage in order to prevent deformation of the optic element. Thus, some type of transfer process is still generally necessary for loading the IOL into the inserter.

Prior to transferring the IOL into the inserter, the IOL is stored in an unstressed state inside some type of storage case. During loading, the storage case is typically attached above or to one side of a load chamber that is in line with a pushrod used during insertion of the IOL into an eye. As the IOL is loaded into the load chamber, various means and mechanisms known in the art may be used to manipulate the IOL from an unstressed storage state to a state more suitable for delivery of the IOL into the eye of a subject or patient. In transferring the IOL from the holding chamber, the IOL is thus moved along an axis that is normal to the longitudinal axis of travel of the inserter pushrod. Such designs require relatively complex mechanisms to move IOL along two substantially orthogonal axes (i.e., the transfer axis and the longitudinal axis of the inserter pushrod). Another potential problem with such loading configurations is that the mechanisms for transferring the IOL may fail to provide adequate visibility of the IOL within the inserter. Inadequate visibility of the IOL makes it more difficult to provide adequate lubrication and ensure proper orientation and of the IOL.

It would be advantageous to provide devices, systems, and methods to better facilitate the transfer of IOLs into an inserter and/or placement of IOLs into the eye of a subject during an ocular surgery.

SUMMARY OF THE INVENTION

The present invention relates to devices, systems, and methods for delivering an intraocular lens into the eye of a subject or patient that addresses at least some of the problems discussed above. Using embodiments of the invention, an intraocular lens may be transferred from a storage case to an inserter handpiece and/or inserter cartridge in preparation for placement into the eye of the subject. In certain embodiments, portions of the intraocular lens, such as the optic or haptics, may be manipulated during transfer into the inserter handpiece from a configuration that is more suitable for storage of the intraocular lens to a configuration that is more suitable for insertion into the eye.

In accordance with one aspect of the invention, a system for delivering an intraocular lens (IOL) into the eye of a subject is provided, comprising an IOL inserter having a handpiece and a nosepiece. The nosepiece has a transfer interface for receiving an IOL, a load chamber open to the transfer interface, and an insertion tube open to the load chamber. The inserter further includes a pushrod movable through the nosepiece for urging the IOL from the load chamber and through the insertion tube in a delivery procedure. A lens case stores the IOL prior to usage and defines a transfer port that engages the transfer interface of the nosepiece. A transfer mechanism in the lens case automatically transfers the IOL to the load chamber upon engagement between the lens case and nosepiece. The transfer mechanism further permits disengagement of the lens case from the nosepiece upon IOL transfer therebetween.

In the exemplary IOL delivery system the nosepiece may be movable relative to the handpiece between a first position for loading the intraocular lens and a second position for delivering the intraocular lens into the subject's eye. Desirably, the transfer interface of the nosepiece faces away from the handpiece in the first position, and the insertion tube faces away from the handpiece in the second position, for instance by rotating 180° about the handpiece between the first and second positions. The nosepiece may include a pivot shaft moveable between two ends of a slot in the handpiece, and wherein the pivot shaft is positioned at a first end in the first position of the nosepiece and at a second end in the second position of the nosepiece. In on embodiment, the nosepiece is restrained from rotation about the handpiece when the pivot shaft is positioned at the first end.

The exemplary IOL delivery system may further include a viscoelastic manifold adapted to engage the transfer interface of the nosepiece, the manifold having at least one inlet port leading to internal channels such that a viscoelastic medium injected into the inlet port is guided by the internal channels into the load chamber. Also, the IOL may comprise an optic configured to focus light onto the retina of an eye when placed inside the eye and a haptic coupled to the optic for holding the optic within the eye, and the lens case includes a haptic folder configured to move the haptic to a predetermined position relative to the optic prior to IOL transfer and then to transfer with the IOL to the inserter. The lens case may have a cap that displaces the haptic folder upon removal of the cap from the lens case such that the haptic folder moves the haptic to its predetermined position relative to the optic.

In accordance with a preferred method for delivering an intraocular lens (IOL) into the eye of a subject an IOL inserter is provided having a nosepiece with a transfer interface for receiving an IOL and a load chamber open to the transfer interface. A lens case is also provided for storing the IOL prior to delivery into the subject's eye, the lens case having a transfer port adapted to engage the transfer interface of the nosepiece and a transfer mechanism. The transfer port of the lens case engages with the transfer interface of the load chamber which automatically actuates the transfer mechanism and transfers the IOL to the load chamber of the nosepiece. The lens case is disengaged from the nosepiece, and the IOL delivered through the nosepiece into the subject's eye.

In the aforementioned method, the inserter may have a handpiece and a nosepiece, wherein the method includes placing the nosepiece in a first position relative to the handpiece for engaging the lens case, and then moving the nosepiece into a second position relative to the handpiece after disengaging the lens case for delivering the intraocular lens into the subject's eye. The inserter may also comprise an insertion tube open to the load chamber and the nosepiece rotates 180° about the handpiece, wherein the transfer interface of the nosepiece faces away from the handpiece in the first position and the insertion tube faces away from handpiece in the second position. The method also desirably includes engaging a viscoelastic manifold with the transfer interface of the nosepiece in the first position, the manifold having at least one inlet port leading to internal channels, and injecting a viscoelastic medium into the inlet port to be guided by the internal channels into the load chamber. The IOL may have an optic and a haptic coupled to the optic, the lens case further includes a movable haptic folder, and the method includes displacing the haptic folder to move the haptic to a predetermined position relative to the optic prior to IOL transfer, and transferring the haptic folder with the IOL to the inserter. The haptic folder may be displaced automatically by simply removing the cap to pro-position the haptic.

Another aspect of the invention is an intraocular lens (IOL) and lens case combination for cooperating with an IOL inserter. The combination has intraocular lens comprising an optic and a haptic coupled to the optic, and a lens case for storing the IOL prior to usage. The lens case has a transfer port adapted to engage the inserter and a transfer mechanism within the lens case that retains the IOL during storage and automatically releases the IOL upon engagement between the lens case and inserter. The transfer mechanism further permits disengagement of the lens case from the inserter after IOL transfer therebetween, and has a haptic folder configured to move the haptic to a predetermined position relative to the optic prior to IOL transfer and then to transfer with the IOL to the inserter.

In the combination above, a cap may be provided for the lens case that displaces the haptic folder upon removal of the cap from the lens case such that the haptic folder moves the haptic to its predetermined position relative to the optic. Also, the transfer mechanism desirably has a haptic retention finger that displaces upon removal of the cap from the lens case. The transfer mechanism may comprise jaws that retain the IOL in a fixed location during storage and separate to release the IOL upon engagement of the transfer port with the inserter. Desirably, the jaws are molded and connect at a living hinge.

One aspect of the present invention involves a lens case for storing an intraocular lens. The lens case comprises a housing for storing an intraocular lens and a support member configured to support the intraocular lens. The support member comprises a plurality of jaws, the jaws having a closed configuration for holding the intraocular lens and an open configuration for releasing the intraocular lens. The lens case further comprises a passage formed when the jaws are in the open configuration, the passage including an opening in the lens case for transfer of the intraocular lens into an intraocular lens inserter or inserter cartridge for placing the intraocular lens into an eye of a subject. The lens case may further comprise an intraocular lens that is disposed between the jaws, the intraocular lens comprising an optic and a haptic coupled to the optic. The lens case may be configured to maintain the haptic in either a first position in which a distal portion of the haptic is disposed farther from the optic or a second position in which the distal portion of the haptic is disposed closer to optic. Preferably, the lens case is configured to provide the second position during transfer of the intraocular lens into an inserter and/or inserter cartridge.

In another aspect of the invention, the above lens case is part of an insertion system for delivering an intraocular lens into the eye of a subject. The insertion system further comprises an inserter configured for receiving the intraocular lens from the lens case and for placing the intraocular lens into the eye of the subject. The inserter comprises a load chamber configured to receive the intraocular lens from the lens case and an insertion tube coupled to the load chamber for delivering the intraocular lens into an eye. The inserter may farther comprise a nosepiece or cartridge disposed at a distal end of the inserter, the nosepiece comprising a rotational axis substantially perpendicular to the longitudinal axis and a load chamber with a transfer interface for receiving an intraocular lens. The nosepiece may be adapted to rotate approximately 180 degrees about the rotational axis between a first orientation for loading the intraocular lens and a second orientation for delivering the intraocular lens into the eye of a subject.

In yet another aspect of the invention, a lens case for storing an intraocular lens comprises an intraocular lens including an optic and a haptic coupled thereto, a housing for storing the intraocular lens, a support member configure to support the intraocular lens, and a transfer mechanism. The lens case may further comprise a shuttle that is configured to move with the intraocular lens so as to carry and/or support the intraocular lens during transfer from the lens case to an inserter or cartridge that is used to place the intraocular lens into the eye of a subject. In some embodiments, the shuttle is replaced by or supplemented by a haptic manipulator or haptic folder that is configured to move the haptic to a predetermined position relative to the optic, for example, during transfer of the lens from the lens case to the inserter.

In still another aspect of the present invention, a method of preparing an intraocular lens for delivery into the eye of a subject comprises providing an inserter for delivering an intraocular lens into the eye of a subject, the inserter comprising a load chamber for receiving the intraocular lens. The method also comprises providing a lens case according to an embodiment of the invention that includes a plurality of jaws for holding an intraocular lens. The method additionally comprises engaging the lens case with the inserter and moving the jaws from a closed configuration to an open configuration. The method further comprises disengaging the lens case from the inserter and transferring the intraocular lens to the inserter.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIG. 13d is an enlarged perspective view of the components of lens case in FIG. 13a.

FIG. 14a is a another embodiment of a lens case according to the invention showing a pair of jaws in a closed configuration.

FIG. 14b is a side view of another embodiment of a lens case according to the invention showing a pair of jaws in an open configuration.

FIG. 15 is a perspective view of the components of the lens case in FIG. 14a.

FIG. 17b is a side view of the lens case shown in FIG. 17a.

FIGS. 18a and 18b are side and top views, respectively, of another embodiment of a lens case according to the invention showing means for rotating an intraocular lens.

FIG. 19 is a side view of another embodiment of a lens case according to the invention showing a chord configured to move the haptics of an intraocular lens.

FIGS. 31a-d are side views showing use of the lens cartridge shown in FIG. 15.

FIGS. 32 and 33 are perspective assembled and exploded views of an exemplary handpiece of an inserter according to an embodiment of the invention.

FIGS. 34 and 35 are perspective assembled and exploded views of an insertion system according to an embodiment of the invention showing the handpiece of FIG. 32 coupled to a nosepiece and having a viscoelastic application manifold connected thereto.

FIGS. 36 and 37 are perspective assembled and exploded views of an exemplary intraocular lens (IOL) case and internal IOL transfer mechanism of the present invention.

FIGS. 38 and 39A are enlarged perspective exploded and assembled views of the IOL transfer mechanism shown in FIG. 37 with a top jaw shown pivoted upward to expose internal components thereof.

FIG. 39B is an enlargement in the circle 39B-39B of FIG. 39A showing details of an IOL retaining system in the IOL transfer mechanism.

FIG. 40 is perspective assembled view of the handpiece of FIG. 32 shown coupled to the nosepiece of FIG. 35 in an IOL transfer mode.

FIG. 41 is an enlarged perspective exploded view of a distal end of the handpiece and the nosepiece.

FIGS. 42-46 are various views of a tubular barrel of the exemplary handpiece of FIG. 32.

FIGS. 47A-47D are several views of the nosepiece of the present invention.

DETAILED DESCRIPTION OF THE PREFERRED EMBODIMENTS

Figure 1:
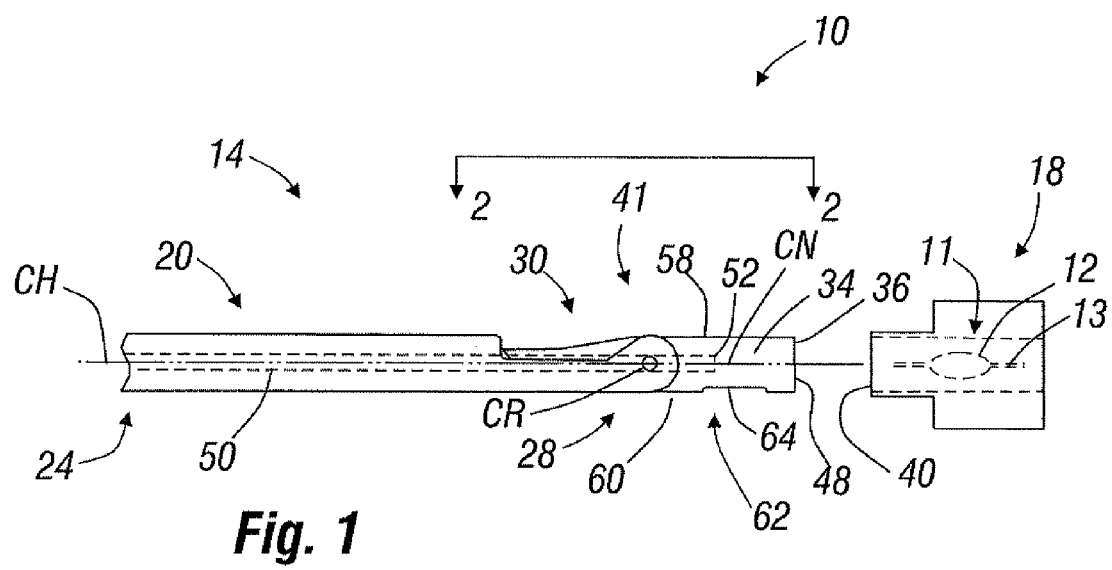
FIG. 1 is a side view of an insertion system according to an embodiment of the invention showing a lens case and an inserter with a nosepiece disposed in a load position.

Referring to FIGS. 1-6, in certain embodiments, an insertion system 10 for delivering an intraocular lens 11 into the eye of a subject comprises an inserter (injector) 14 for delivering the intraocular lens 11 and a lens case 18 for holding the intraocular lens 11 prior to delivery into the eye by the inserter 14. The intraocular lens 11 comprises an optic 12 that is configured, in conjunction with the cornea of the eye and/or an additional IOL, to focus light onto the retina of eye. The intraocular lens 11 may further comprise one or more fixation members or haptics 13 configured to hold and/or center the optic 12 within the eye. The inserter 14 comprises handpiece 20 having a longitudinal axis CH, a proximal end 24, and a distal end 28. The inserter 14 further comprises a cartridge or nosepiece 30 disposed at the distal end 28 of the inserter 14. The nosepiece 30 has a rotational axis CR that is substantially perpendicular to the longitudinal axis CH and a load chamber 34 with a transfer interface 36 for receiving the intraocular lens 11. The lens case 18 has a transfer port 40 for delivering, moving, or transferring the intraocular lens 11 from the lens case 18 and into the load chamber 34.

Figure 4:
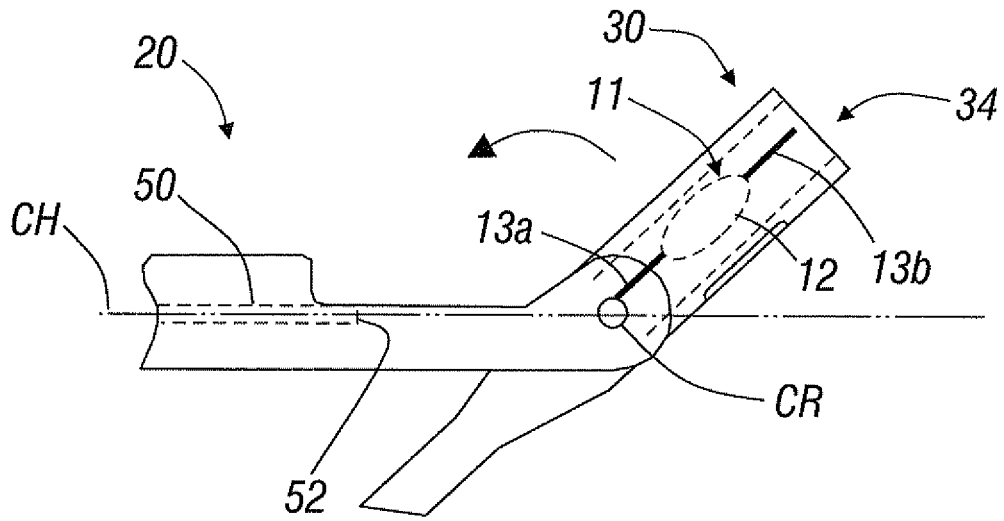
FIG. 4 is a side view of the inserter illustrated in FIG. 1 showing the nosepiece disposed in an intermediate position.
Figure 5:
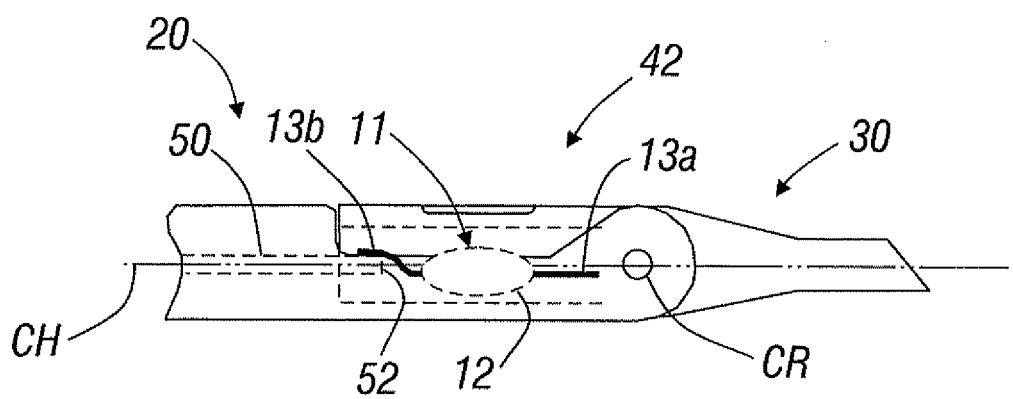
FIG. 5 is a side view of the inserter illustrated in FIG. 1 showing the nosepiece disposed in a delivery position.
Figure 6:
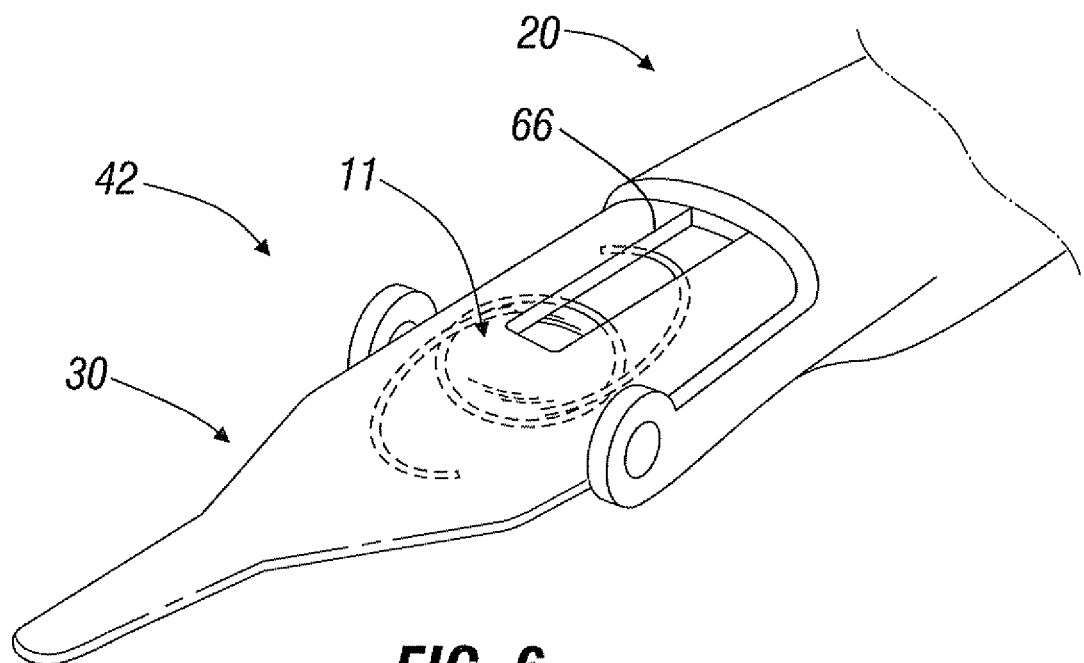
FIG. 6 is a perspective view of an inserter according to an embodiment of the invention showing an intraocular lens disposed for insertion into the eye of a subject.

The nosepiece 30 is adapted to move or rotate between a first position 41 suitable for loading or transferring the intraocular lens 11 (illustrated in FIG. 1) and a second position 42 suitable for delivering the intraocular lens 11 into the eye (illustrated in FIG. 5). For example, the nosepiece 30 may be adapted to rotate approximately 180 degrees about the rotational axis CR between the first position 41 and the second position 42 (compare FIGS. 1, 4, and 5). In certain embodiments, the nosepiece 30 may be adapted for placement in intermediate positions between the first and second positions 41, 42 and/or beyond the first position 41 or the second position 42. For example, an intermediate position between the first and second positions 41, 42 might be utilized for insertion of a viscoelastic or other substance either before and/or after loading of the intraocular lens 11 into the nosepiece 30.

Prior to use by a practitioner, the intraocular lens 11 is preferably disposed inside the lens case 18. The lens case 18 may be used to secure and protect the intraocular lens 11 during shipment from the manufacturer and for storage of the intraocular lens 11 over an extended period of time, for example, over a period of at least about six months, one year, or even over a period of at least 2 years to at least 4 years. The lens case 18 preferably maintains the intraocular lens 11 in a non-stress or low-stress condition in order to prevent permanent deformation of the optic 12 that could result in undesirable optical effects or aberrations after placement inside an eye. The interior of the lens case 18 may be filled or partially filled with a substances such as a liquid or gel; for example, a viscoelastic material or OVD. Such substances may be supplied prior to shipment by the manufacturer and/or by a practitioner prior to transfer between the lens case 18 and the inserter 14 (or associated lens cartridge). The viscoelastic material may be used, for example, to protect or preserve the intraocular lens 11 or to maintain the intraocular lens 11 in non-stress or low stress condition.

In certain embodiments, the interior of the lens case 18 is filled or partially filled with a balanced salt solution (BSS) or similar fluid. In other embodiments, the interior of the lens case 18 is filled or partially filled with a viscoelastic or OVD in combination with a BSS or similar fluid. The use of a BSS, alone or in combination with OVD's, may favorably reduce friction. For example, the use of a BSS may be used to increase lubricity between the intraocular lens 11 and the internal walls of the inserter 14 (e.g., the insertion tube wall of the inserter cartridge). In addition, a BSS, alone or in combination with OVD's, may be used to reduce tackiness of the haptics 13, especially in the case where the intraocular lens 11 is a one-piece intraocular lens in which the optic and haptics are integrally fabricated from a single material. In other embodiments, a combination of OVD's, with or without a BSS, may be used to reduce friction or tackiness.

The lens case 18 may be disposable and made of plastic material suited for storage and protection of the intraocular lens 11. Alternatively, at least portions of the lens case 18 may be reusable, in which case the at least portions may be made of a metal material or some other material that may be used to increase the strength, durability, or function of the lens case 18.

The inserter 14 may be constructed for delivery of any of the various types of intraocular lenses known in the art. For example, the intraocular lens 11 may be a foldable lens made of at least one of the materials commonly used for resiliently deformable or foldable optics, such as silicone polymeric materials, acrylic polymeric materials, hydrogel-forting polymeric materials, such as polyhydroxyethylmethacrylate, polyphosphazenes, polyurethanes, and mixtures thereof and the like. In one embodiment, the inserter 14 is used with an intraocular lens 11 having an optical zone that is made of SENSAR® brand of acrylic. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins. The lens material preferably has a refractive index allowing a relatively thin, and preferably flexible optic section, for example, having a center thickness in the range of about 150 microns to about 1000 microns, depending on the material and the optical power of the intraocular lens 11. At least portions of the intraocular lens 11, for example one or more haptics or fixation members, may be constructed of a more rigid material including such polymeric materials as polypropylene, polymethylmethacrylate PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like.

Additionally, the inserter 14 may be configured to deliver intraocular lenses having either a single focus or producing two or more foci using refraction, diffraction, or some combination thereof. The inserter 14 may also be used to deliver an accommodating intraocular lens or system of lenses, either together or separately. The inserter 14 may be configured to deliver the intraocular lens 11 into the capsular bag of the eye or into some other portion of the eye, such as the anterior chamber of the eye. The inserter 14 may be used to deliver the intraocular lens 11 into either a phakic or aphakic eye. Additionally, the inserter 14 may be used to deliver the intraocular lens 11 into the eye of a subject already having an intraocular lens located either in the capsular bag or otherwise located within or on the eye.

The transfer port 40 of lens case 18 may be used during transfer of the intraocular lens 11 and configured to couple the transfer interface 36 of load chamber 34. The transfer port 40 may further comprise a cover (discussed below) for sealing the interior of the lens case 18. The cover may be manually removed just prior to transfer of the intraocular lens 11 into the load chamber 34. Alternatively, the cover may be constructed to automatically move out of the way to allow transfer of the intraocular lens 11 when the lens case 18 engages the nosepiece 30.

Figure 2:
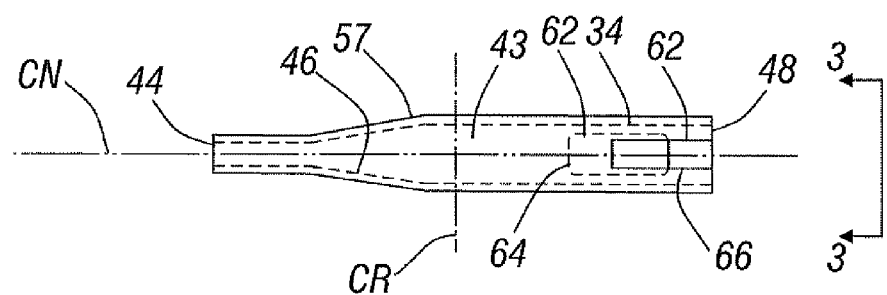
FIG. 2 is a top view of a nosepiece of the inserter illustrated in FIG. 1.

As illustrated in FIG. 2, the nosepiece 30 further comprises a delivery channel 43 for delivering the intraocular lens 11 into the eye, the delivery channel 43 having a delivery port 44 with a cross-sectional area that is preferably less than a cross-sectional area of the load chamber 34. Unless otherwise indicated, the term "cross-sectional area," as used herein, means the area of a referenced element in a plane that is perpendicular to the longitudinal axis CH of the handpiece 20. The delivery channel 43 comprises a tapered portion 46 extending from the load chamber 34 and is substantially disposed along the longitudinal axis CH when the nosepiece 30 is disposed in the first position 41 and when the nosepiece 30 is disposed in the second position 42. The tapered portion 46 may be used to compress and form the intraocular lens 11 into an elongated and/or compressed configuration suitable for delivery into the eye through the delivery port 44.

Figure 3:
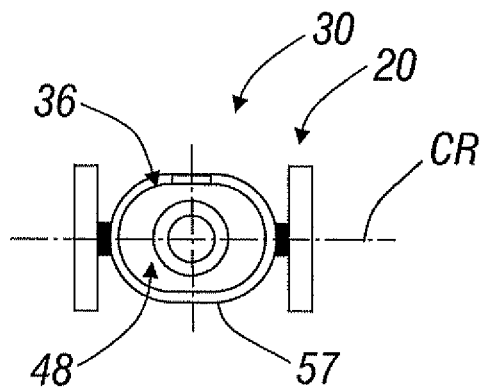
FIG. 3 is an end view of the inserter illustrated in FIG. 1.

Referring to FIG. 3, the interface 36 of the nosepiece 30 may comprise an aperture 48 that is preferably substantially centered about the longitudinal axis CH and distally located relative to the delivery channel 43 when the nosepiece 30 is in the first position 41. The interface 36 may alternatively or additionally comprise other elements or means, such as a cover, for providing protection of the intraocular lens 11 and/or for providing transfer of the intraocular lens 11 to the inserter 14.

Referring again to FIG. 1, the inserter 14 preferably comprises a pushrod 50 with a tip 52 that is preferably attached at the proximal end 24 of the handpiece 20. With the inserter 14 in the second position 42, the tip 52 of the pushrod 50 traverses substantially along the longitudinal axis CH and may be used to advance the intraocular lens 11 down the nosepiece 30 and into the eye. The handpiece 20 of the inserter 14 directs the tip 52 of the pushrod 50 along the longitudinal axis CH towards the distal end 28 and into the load chamber 34, where the tip 52 engages the intraocular lens 11 during delivery of the intraocular lens 11.

In certain embodiments, the pushrod 50 may be configured to traverse through the nosepiece 30 when the nosepiece 30 is in the first position. In such embodiments, for example, the tip 52 may be used to control one or more of the haptics of the intraocular lens 11 during transfer from the lens case 18. The pushrod 50 may also be used to help maintain the nosepiece 30 in the first position 41, as illustrated in FIG. 1.

The tip 52 of the pushrod 50 may engage the intraocular lens 11 using any of the devices or methods known in the art.

For example, the tip 52 of the pushrod 50 may either push against an edge portion of the intraocular lens 11. Alternatively, the tip 52 of the pushrod 50 may engage an inner portion of the intraocular lens 50 in order to more evenly distribute the pushing force over a greater area of the lens surface. In other embodiments, the tip 52 of the pushrod 50 does not directly contact the intraocular lens 11, but instead engages an intermediate device or substance, such as a viscoelastic, that distributes pressure across the intraocular lens 11 that causes it to proceed through the nosepiece 30 and into the eye.

The inserter 14 is adapted to receive the intraocular lens 11 from the lens case 18 and to deliver the intraocular lens 11 into the eye, for example, after the natural lens has been removed. The inserter 14 and its various components may be made of any of the materials common in the art such as plastic or metal. Plastic materials are preferable if the inserter 14 is made for one-time use or a limited number of uses before disposing of the inserter 14. Metal materials are preferable if the inserter is constructed for reuse, where the inserter 14 is sterilized prior to each use using either heat and/or sterilizing agents such as alcohol.

In the illustrated embodiment, a longitudinal axis CN of the nosepiece 30 is substantially centered within the handpiece 20. The term "substantially centered," as used here, means that a small amount of translational or rotational offset may be present in certain embodiments when the nosepiece 30 is in at least one of the first and second positions 41, 42. For instance, a small amount of translational or rotational offset may be used to provide a predetermined amount of transverse force between the tip 52 of the pushrod 50 and at least some portion of the nosepiece 30, as describe in further detail below herein. In some embodiments, the longitudinal axis CN is offset from the longitudinal axis CH of the handpiece 20, for example, to provide a desired position of the intraocular lens 11 relative to the tip of the pushrod 50.

The nosepiece 30 may be coupled to the handpiece 20 using devices and means known to those of skill in the art. In certain embodiments, the nosepiece 30 is lockably coupled to the handpiece 20 when the nosepiece 30 is in the first position 41, the second position 42, and/or one or more intermediate positions. The means or devices used to lock the nosepiece 30 in the first and/or second positions 41, 42 preferably provide a locking force of sufficient magnitude to substantially prevent the nosepiece 30 from moving during loading of the intraocular lens 11 into the nosepiece 30 and/or delivery of the intraocular lens 11 into the eye. Preferably, the magnitude of the locking force is low enough to allow relatively easy manipulation of the nosepiece 30 between the first and second positions 41, 42. Alternatively, the nosepiece 30 may be locked in the first and/or second positions using a lock mechanism or device (e.g., a pin or spring latch) that may be released or disengaged when manipulating the nosepiece 30 between the first and second positions 41, 42. In one embodiment, the nosepiece 30 is locked in the first position 41 by either pressing the tip 52 of the pushrod 50 against the delivery port 44 of the nosepiece 30 or by at least partially traversing the pushrod 50 through the delivery channel 43 of the nosepiece 30.

In certain embodiments, the longitudinal axis CN of the nosepiece 30 is substantially coaxial with the longitudinal axis CH of the handpiece 20 when the nosepiece 30 is in either the first position 41 or the second position 42. The term "substantially coaxial" as used herein means that the axes CH and CN are coaxial or that there is an offset angle between the axes CH and CN when the nosepiece 30 is in at least one of the first position 41 and the second position 42. In other embodiments, the axes CH and CN are offset from one another. In yet other embodiments, there is an offset angle between the axes CH and CN in either a clockwise or counter-clockwise direction when the nosepiece 30 is in the first and/or second positions 41, 42 (e.g., FIG. 27). In such embodiments, the offset angle is preferably less than about 10 degrees, more preferably less than about 5 degrees, and even more preferably less than about 2 degree. In one embodiment, an offset angle exist between the axes CH and CN when the nosepiece 30 is in the second position 42 such that the pushrod 50 produces a transverse force on at least some portion of the nosepiece 30, such as in the delivery channel 43, as the pushrod 50 advances along the longitudinal axis CH. This transverse force may be advantageously used to prevent the tip 52 of the pushrod from moving on top of a portion of the intraocular lens 11 during delivery into the eye. In other embodiments, The nosepiece 30 may further comprise an outer surface 57 that substantially surrounds the load chamber 34 and the delivery channel 43. Preferably, the outer surface 57 is generally tapered from one end of the nosepiece 30 (e.g., near the transfer interface 36) having a relatively large cross-section, to an opposite end (e.g., near the delivery port 44) having a relatively small cross-section. The relatively small cross-section allows, among other things, the nosepiece 30 to be inserted into a relatively small incision in the eye, while the relatively large cross-section allows the intraocular lens 11 to be loaded into the load chamber 34 of the nosepiece 30 in a substantially uncompressed state. The outer surface 57 of the nosepiece 30 may further comprise a top face 58 and a bottom face 60 containing one or more openings 62. The openings 62 may be in the form of an aperture, notch, or some other type of void for providing at least partial access to the load chamber 34 and/or the delivery channel 43. For example, referring to FIGS. 1 and 2, the bottom face 60 is disposed below the load chamber 34 and comprises an aperture 64 that is rectangular in shape. The aperture 64 may, of course, take other shapes such as circle or a slit. As illustrated in FIG. 2, the top face 58 is disposed above the load chamber 34 and comprises an elongated notch 66. In other embodiments, for example as illustrate in FIG. 6, the elongated notches 66 are disposed on both the top and bottom faces 58, 60. In still other embodiments, there is only one opening 62 on either the top face 58 or the bottom face 60. Alternatively, one or more openings may be disposed at locations other than or in addition to the top and bottom faces 58, 60, for instance, on the sides of the outer surface between the top and bottom faces 58, 60.

The openings 62 may be used to visually inspect the insides of load chamber 34 prior to, during, or after transfer of the intraocular lens 11 into the nosepiece 30. The opening 62 may also be used to introduce one or more substances, for example a viscoelastic, into the load chamber 34 or some other portion of the nosepiece 30. Such substances may be introduced into the load chamber 34 from the transfer interface 36 of the load chamber 34 and visually inspected via the opening 62. The opening 62 may also be used as an overflow port through which excess amounts of injected substances exit the load chamber 34. Other uses of the opening 62 are consistent with embodiments of the inserter 14 or the insertion system 10. For instance one or more openings 62 may be configured to receive inspection instruments or tools for manipulating or otherwise preparing the intraocular lens 11 for delivery through the delivery channel 43 and into the eye. The opening 62 may also be used to aid in alignment of inserter 14 components with lens case 18 components when the nosepiece 30 is in either the first or second positions 41, 42.

Figure 7:
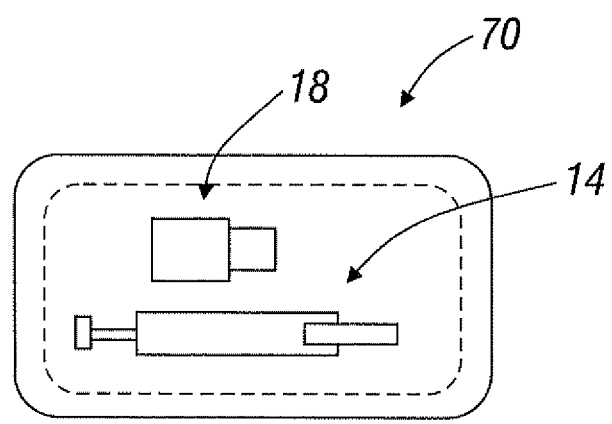
FIG. 7 is a top view of a container according to an embodiment of the invention for holding an insertion system that includes an inserter and a lens case.

Referring to FIG. 7, in certain embodiments, the insertion system 10 further comprises a package or container 70 for holding the inserter 14 and the lens case 18. For example, the container 70 may be in the form of a shrink-wrap package 70 illustrated in FIG. 7 and comprising top and bottom sheets of material that envelop the inserter 14 and the lens case 18. The inserter 14 and the lens case 18 are preferably placed inside the container 70 in a sterile environment and sealed in a manner that maintains the sterility of the inserter 14 and the lens case 18 until they are ready for use. Alternatively, the inserter 14 and the lens case 18 may be sterilized after being enclosed inside the container 70. In other embodiments, the lens case 18 and the inserter 14 are packaged in separate containers, for example, to reduce inventory costs. In such embodiments, the individual containers may be placed together by the manufacturer, distributor, or user in a larger container or package, for example, for shipping or storage. In some embodiments, an inserter is packaged in one type of container for shipment with one or more lens cases 18 containing intraocular lenses having, for instance, differing Diopter powers, differing spherical aberration, or some other optical or mechanical characteristic.

The container 70 may be made of plastic, metal, or any other suitable material suitable for sealing the inserter 14 and the lens case 18 and providing a sterile environment during storage. Combinations of such material are also possible. For example, the bottom sheet of the shrink-wrap package 70 may be made of a metal foil, while the top sheet is made of a transparent plastic material that is bondable to the metal foil, thus allowing visible inspection of the inserter 14 and the lens case 18 while inside the container 70. The container 70 may take other configurations, besides that illustrated in FIG. 7, for example a cardboard box.

Figure 8:
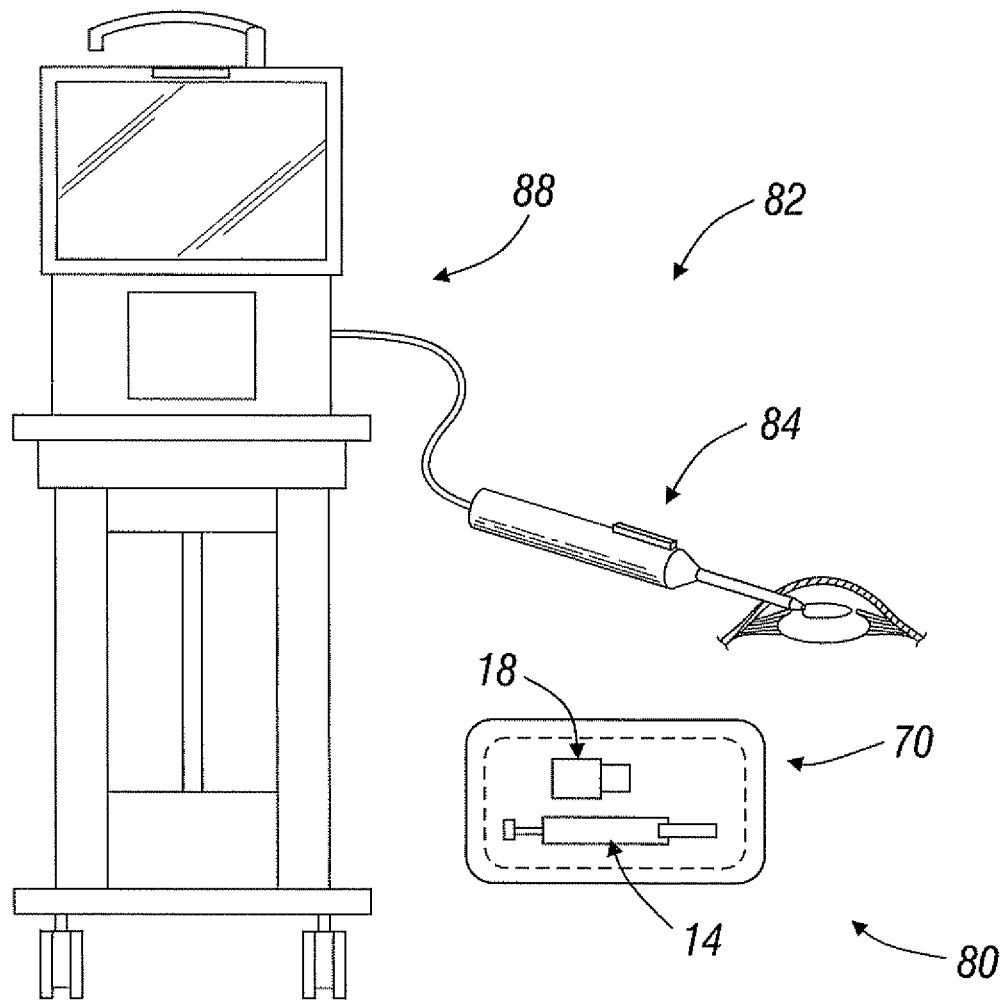
FIG. 8 illustrates a surgical system according to the present invention for performing an ocular surgery.

Referring to FIG. 8, in certain embodiments, a surgical system 80 for performing an ocular surgery comprises a phacoemulsification system 82 having a surgical handpiece 84 for removing the natural lens of an eye and an electronic controller 88 for controlling the fluidics of surgical handpiece 84 and/or the phacoemulsification power into the surgical handpiece 84. The system 80 further comprises at least one inserter, such as the inserter 14, and at least one lens case, such as the lens case 18, wherein the lens case 18 preferably has an intraocular lens enclosed therein. The system 80 may include a plurality of lens cases, such as the lens case 18, and/or inserters, such as the inserter 14. Alternatively, the system 80 may include a plurality of containers 70, each containing at least one inserter 14 and at least one lens case 18, preferably containing an intraocular lens therein. Such configurations allow a practitioner to perform multiple surgeries. In certain embodiments, the controller 88 controls the delivery of electrical power into a transducer, such as a piezo-electric driver, that is part of the surgical handpiece 84. In such embodiments, the piezo-electric driver changes size in accordance with changes in the electrical voltage and/or current provided by the controller 88. The controller 88 may also be used to control and/or monitor the irrigation fluid entering the eye and/or the aspiration used to remove fluid from the eye.

Figure 9:
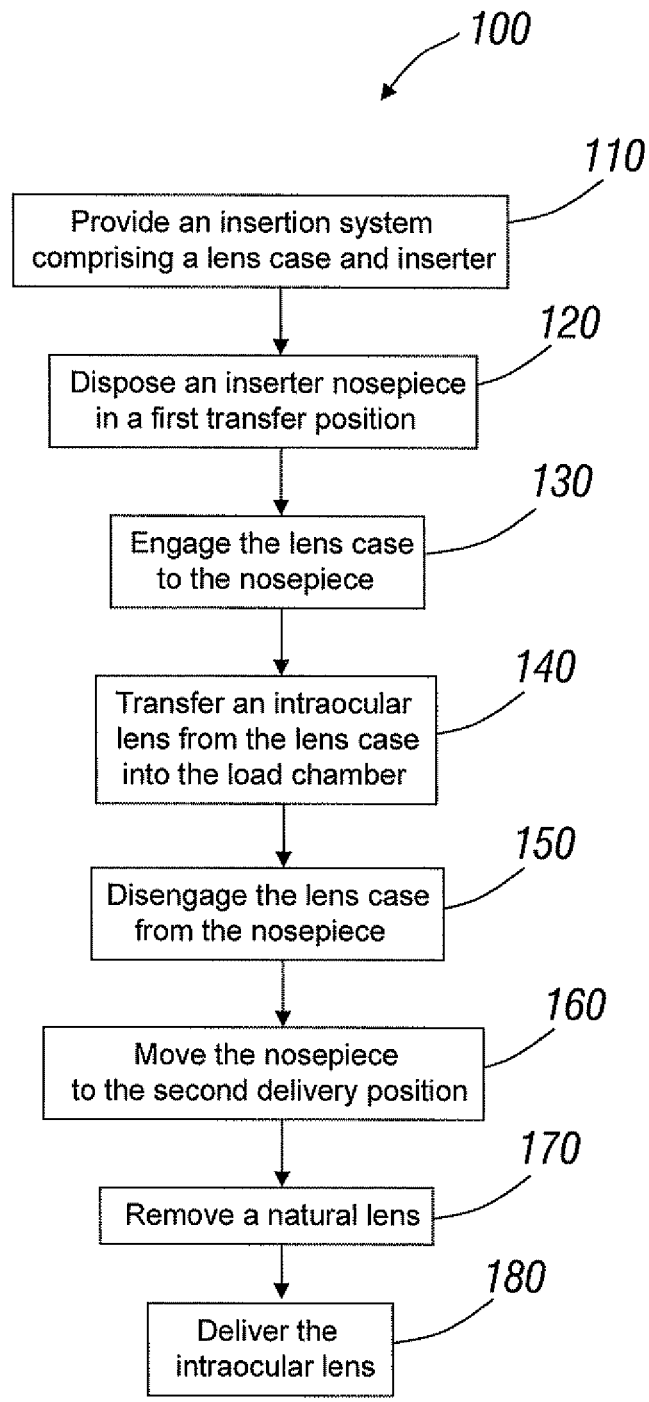
FIG. 9 is a block diagram illustrating a method according to an embodiment of the present invention for delivering an intraocular lens into eye of a subject.

Referring to FIG. 9, in certain embodiments, a method 100 for delivering the intraocular lens 11 into the eye of a subject comprises an operational block 110, which comprises providing the insertion system 10, including the inserter 14 and the lens case 18. The method 100 further comprises an operational block 120, which comprises disposing the nosepiece 30 in the first position 41, with the delivery channel 43 being disposed along the longitudinal axis CH. The method 100 also comprises an operational block 130, which comprises engaging the lens case 18 to the nosepiece 30 such that the transfer port 40 of the lens case 18 operably connected to the transfer interface 36 of the load chamber 34. The method 100 further comprises an operational block 140, which comprises transferring the intraocular lens 11 from the lens case 18 into the load chamber 34. The method 100 additionally comprises an operational block 150, which comprises disengaging the lens case 18 from the nosepiece 30. The method 100 also comprises an operational block 160, which comprises moving the nosepiece 30 to the second position 42, which is suitable for delivering the intraocular lens 11 into the eye of a subject. The method 100 optionally comprise an operational block 170, which comprises optionally removing a natural lens from the eye of a subject. The method 100 also comprises an operational block 180, which comprises delivering the intraocular lens 11 into the eye of a subject.

In operational block 110, the insertion system 10 may be packaged in a container such as the container 70 illustrated in FIG. 7. Preferably, the intraocular lens 11 is preloaded in the lens case 18 by the manufacturer such that the intraocular lens 11 is in a sterile, unstressed environment.

In operational block 120, the nosepiece 30 is oriented in the first position 41, as illustrated in FIG. 1. By disposing the nosepiece 30 in this position, the load chamber 34 and the transfer interface 36 are distally located from the remaining portions of the inserter 14 and are thus readily accessible for transfer of the intraocular lens 11 from the lens case 18.

Figure 10:
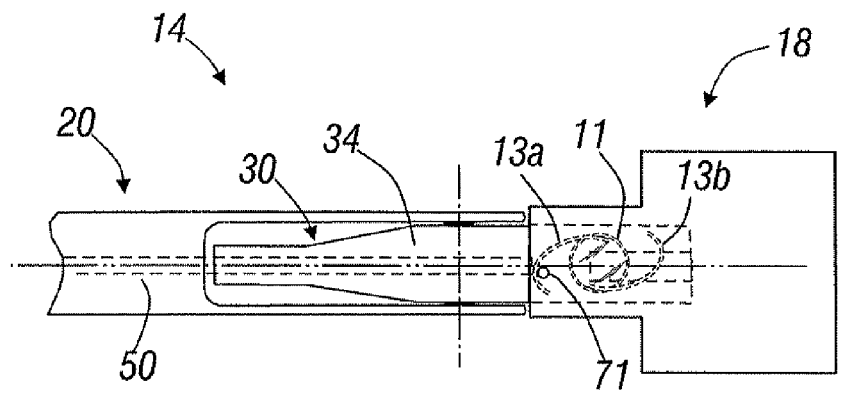
FIG. 10 is a top view of the insertion system shown in FIG. 1 illustrating engagement of the lens case with the nosepiece.

Referring to FIG. 10, in operational block 130, lens case 18 is engaged with the nosepiece 30. During engagement, the lens case 18 may at least partially surround the load chamber 34 of the nosepiece 30 such that the transfer interface 36 of the load chamber 34 is aligned and/or coupled to the transfer port 40 of the lens case 18. The engagement may be secured by means for at least partially locking the lens case 18 and the nosepiece 30 together, for example through the use of detents or spring loading. In certain embodiments, the load chamber 34 at least partially engages the nosepiece 30 prior to use by a practitioner and/or before shipment by the manufacturer or distributor. In such embodiments, the lens case 18 may be more fully engaged with the nosepiece 30 at operational block 130 of the method 100 or, alternatively, the operational block 130 becomes unnecessary altogether.

In operational block 140, the intraocular lens 11 is transferred from the lens case 18 and into the load chamber 34 of the nosepiece 30 in preparation for delivery of the intraocular lens 11 into the eye of a subject. This operation may be totally distinct from the engagement of the lens case 18 with the nosepiece 30 (operational block 130) or may occur simultaneously with the lens case 18 is engaged with the nosepiece 30. In certain embodiments, the tip 52 of the pushrod 50 may be used to manipulate one or more haptics 13a, 13b of the intraocular lens 11 either during transfer of the intraocular lens 11 from the lens case 18 to the load chamber 34 and/or subsequent to the delivery of the intraocular lens 11 into the load chamber 34.

Figure 11:
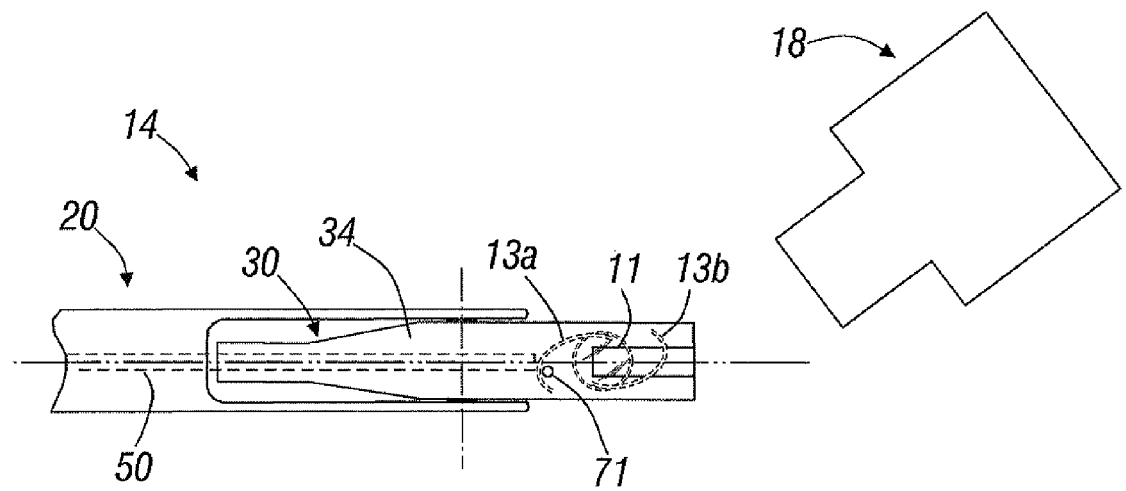
FIG. 11 is a top view of the insertion system shown in FIG. 1 illustrating disengagement of the lens case from the nosepiece.

Referring to FIG. 11, in operational block 150, the lens case 18 is disengaged or separated from the nosepiece 30. After disengagement, the lens case 18 may be disposed of or prepared for receiving a new lens in the same or a subsequent surgery. Structure and/or means may be provided for maintaining the intraocular lens 11 within the load chamber 34 of the nosepiece 30 upon disengagement of the load chamber 34 from the nosepiece 30. For instance, the load chamber 34 may contain one or more catches, hooks, or similar structures for engaging one or more haptics 13a, 13b of the intraocular lens 11 as it moves into the load chamber 34. For example, FIGS. 10 and 11 illustrate a catch 71 that engages the haptic 13a of the intraocular lens 11. During the loading of the intraocular lens 11 into the load chamber 34, the leading edge of the haptic 13a advances past the catch 71 in a way that prevents or impedes the intraocular lens 11 from sliding back towards the aperture 48 of the load chamber 34. In certain embodiments, the catch 71 may be part of the distal tip 52 of the pushrod 50.

Referring again to FIGS. 4 and 5, in operational block 160, the nosepiece 30 is moved to the second position in preparation for delivery of the intraocular lens into the eye of a subject. As illustrated in FIG. 4, moving the nosepiece 30 to the second position 42 preferably comprises rotating the nosepiece 30 about the rotational axis CR to the second position 42, as illustrated in FIG. 5. As seen in FIG. 4, the nosepiece 30 is preferably rotated in a direction such that load chamber 34 and the intraocular lens 11 are disposed above the longitudinal axis CH of the handpiece 20 during rotation from the first position 41 to the second position 42. Alternatively, rotation in the opposite direction may also be used to rotate the nosepiece 30 from the first position 41 to the second position 42. In certain embodiments, the nosepiece 30 rotates between the first position 41 and the second position 42 about the rotational axis CR by approximately 180 degrees. In other embodiments, the nosepiece 30 rotates greater or less than 180 degrees, preferably in the range of about 170 degrees or less to about 190 degrees or more, more preferably about 175 degrees to about 185 degrees, and even more preferably between about 178 degrees and about 182 degrees.

In certain embodiments, the nosepiece 30 moves or rotates between the first position 41 and the second position 42 in an automated or semi-automated fashion. For example, the handpiece 20 may be configured such that nosepiece 30 rotates from the first position 41 to the second position 42 as the pushrod 50 traverses the longitudinal axis CH of the handpiece 20. This may be accomplished, for instance, by using a spring, cam, and/or linkage mechanism that is engaged by the pushrod 50 as is nears the nosepiece 30.

Referring again to FIG. 5, in certain embodiments, moving or rotating the nosepiece 30 from the first position 41 to the second position 42 transversely displaces at least a portion of the haptic 13b from the pushrod 50. For instance, by rotating the nosepiece 30 in the direction indicated in FIG. 4, the haptic 13b may be disposed above the pushrod 50 as the nosepiece 30 arrives at the second position 42 and is pushed in an upward direction by the pushrod 50. By disposing the haptic 13b above the pushrod 50, the intraocular lens 11 is advantageously positioned so that the haptic 13b is not deformed or damaged by the pushrod 50 as the pushrod 50 advances the intraocular lens 11 down the delivery channel 43 for delivery into the eye. This geometry between the pushrod 50 and the haptic 13b is accomplished simply by moving the nosepiece 30 from the first position 41 to the second position 42, with little or no additional manipulation of the haptic 13b by a practitioner, such as a surgeon or assisting nurse. Alternatively, the tip 52 of the pushrod 50 may be moved proximally along the longitudinal axis CH or otherwise adjusted to obtain a predetermined geometric relationship between the intraocular lens 11 and the tip 52 of the pushrod 50. For example, the tip 52 of the pushrod 50 may initially be disposed along a portion of the optic body of the intraocular lens 11 when the nosepiece 30 is rotated from the first position 41 to the second position 42. Subsequently, the tip 52 of the pushrod 50 may then be retracted slightly such that the tip 52 engages or is disposed along the edge of the optic body of the intraocular lens 11.

In the illustrated embodiment, the rotational axis CR of the nosepiece 30 is generally perpendicular to the longitudinal axis CH of the handpiece 20 and intersects, or substantially intersects, the longitudinal axis CH of the handpiece 20. Alternatively, the rotational axis CR may be displaced above or below the longitudinal axis CH (not shown). For example, the rotational axis may be disposed below the longitudinal axis CH by an amount selected to locate the optic 12 of the intraocular lens 11 at a predetermined vertical height relative to the tip 52 of the pushrod 50 and/or the tip of the haptic 13b.

In certain embodiments, the nosepiece 30 may be configured to be movable between the first position 41 and the second position 42 in a manner that combines both rotation and translation of the nosepiece 30. For example, the nosepiece 30 may be rotated from the first position 41 by approximately 180 degrees and then pushed back distally along the longitudinal axis CH of the handpiece 20. The translation motion may be used, for instance, to secure the nosepiece 30 against the body of the handpiece 20 in preparation for delivery of the intraocular lens 11. Other combinations of rotation and/or translation may be use for moving the nosepiece 30 between the first position 41 and the second position 42.

In operational block 170, the natural lens may be removed, for instance using the phacoemulsification system 82. In such instances, the surgical handpiece 84 is used to remove the natural lens of the eye and is under the control of the electronic controller 88, which may be used to control the fluidics of the surgical handpiece 84 and/or the power into the surgical handpiece 84. In certain embodiments, the controller 88 is used to adjust the fluidics of the surgical handpiece 84 and/or power into the surgical handpiece 84 in accordance to system conditions. The amount of power into the surgical handpiece 84 and/or the fluidics of the surgical handpiece 84 may be changed due to the presence of an occlusion in an aspiration line, for example, as disclosed in U.S. Pat. No. 5,700,240, herein incorporated by reference. The removal of the natural lens may be performed before, during, or after the other operational blocks of the method 100. For instance, a nurse or assistant may perform operational blocks 110 through 160 while a surgeon is performing operational block 170. In certain embodiments, the natural lens is not removed or has been removed during a previous surgery and the method 100 would not include the operational block 170. For instance, the intraocular lens 11 may be phakic intraocular lens (e.g., an intraocular lens that is delivered into an eye still containing the natural lens) or a lens that is used to supplement another intraocular lens placed into the eye during a previous surgery.

In operational block 180, the intraocular lens 11 is delivered into the eye by advancing the lens down the delivery channel 43 using the pushrod 50 until the lens passes through the delivery port 44 and into the eye. The tip 52 of the pushrod 50 may have any of the various configurations used in the art or incorporate an innovative configuration designed to provide a predetermined advantage. In certain embodiments, the tip 52 of the pushrod 50 may be made of a relatively soft material and/or be disposed to engage a portion of the intraocular lens 11, for example a fold in the body of the intraocular lens. In other embodiments, the tip 52 of the pushrod 50 may be made of a relatively hard material and/or be disposed to engage an edge or peripheral portion of the intraocular lens 11. The specific characteristics of the pushrod 50 and the tip 52 may be selected depending on the type of intraocular lens being delivered, for example, depending or whether the intraocular lens 11 is made of silicone based material or a relatively stiffer material such as an acrylic based material. Other parameters of the intraocular lens 11 may also be used in determining the specific characteristics of the pushrod 50 and the tip 52.

During delivery of the intraocular lens 11 into the eye, the pushrod 50 is preferably substantially disposed along the longitudinal axis CH. In certain embodiments, the tip 52 and/or the pushrod 50 may be configured to provide a biasing force against at least a portion of the delivery channel 43 during delivery of the intraocular lens 11. Such a biasing force may be used to prevent the tip 52 of the pushrod 50 from moving onto the intraocular lens 11, for example, when the intraocular lens 11 is made of an acrylic material and/or the tip 52 is made of a relatively hard material. In certain embodiments, at least a portion of the pushrod 50, for example the tip 52 of the pushrod 50, may be offset asymmetrically from the longitudinal axis CH. In other embodiments, at least a portion of the pushrod 50 may have an offset angle relative to the longitudinal axis CH. In yet other embodiments, a portion of the inserter 14, for example the delivery channel 43, may have an offset angle relatively to at least one of the longitudinal axis CH and a longitudinal axis along which the tip 52 of the pushrod 50 travels.

The method 100 may additionally comprise introducing one or more substances, for example a viscoelastic, into at least a portion of the nosepiece 30 and/or the lens case 18. The substance may be introduced at any time or at various times during the method 100, for example through one or more of the openings 62 or through the transfer interface 36 of the load chamber 34.

Figure 12:
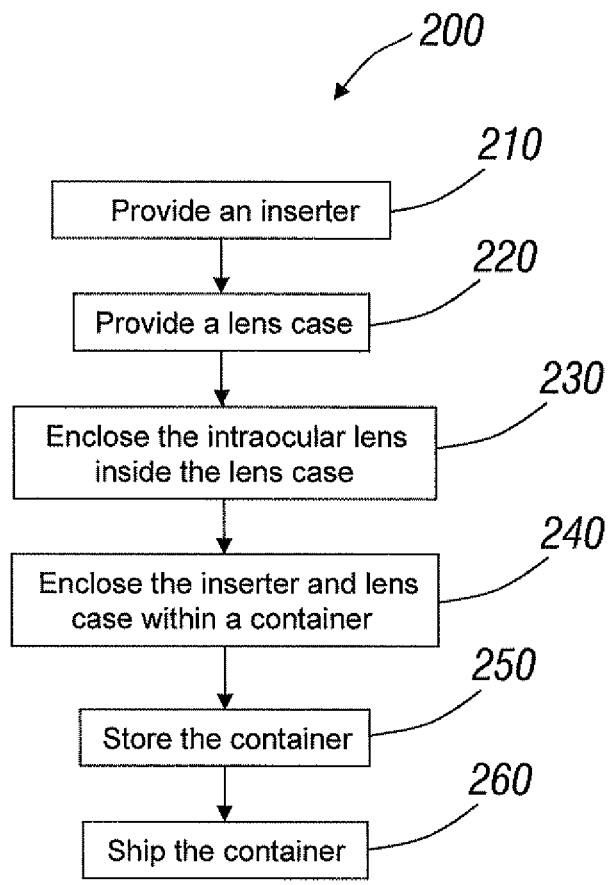
FIG. 12 is a block diagram illustrating a method according to an embodiment of the present invention for packaging and providing an insertion system to a user for delivery of an intraocular lens into the eye of a subject.

Referring to FIG. 12, in certain embodiments, a method 200 for packaging and delivering the insertion system 10 to a user comprises an operational block 210, which comprises providing the inserter 14. The method 200 further comprises an operational block 220, which comprises providing the lens case 18. The method 200 also comprises an optional operational block 230, which comprises optionally enclosing the intraocular lens 11 inside the lens case 18. The method 200 additionally comprises an operational block 240, which comprises enclosing the inserter 14 and lens case 18 within the container 70. The method 200 further comprises an optional operational block 250, which comprises optionally storing the container 70. The method 200 further includes an operational block 260, which comprises shipping the container 70.

In operational block 230, the lens case 18 preferably contains an intraocular lens, for example the intraocular lens 11, prior to packaging inside the container 70. Preferably, the intraocular lens 11 is disposed inside the lens case 18 prior to shipment by the manufacturer or distributor, so as to advantageously maintain the intraocular lens 11 in a sterile environment until ready for use by a practitioner or their assistant. The intraocular lens 11 may be maintained in a low stress or essentially stress free state inside the lens case 18, allowing the intraocular lens 11 to be stored over long periods of time without unwanted permanent deformation that could reduce visual acuity or perception inside the eye.

In operational block 240, the inserter 14 and the lens case 18 are enclosed in the container 70, as illustrated in FIG. 7 and described in greater detail above herein. The inserter 14 and the lens case 18 are preferably packaged such that they are separate from one another; however, other configurations are possible. For example, the inserter 14 and the lens case 18 may be placed adjacent to one another and sealed so as to provide a container 70 that is relatively small. Also, the lens case 18 and the nosepiece 30 may be coupled together prior to shipment to a practitioner and placed and/or sealed inside the container 70.

In operational block 250, the container 70 is stored till ready for shipment, distribution, or use. In operational block 260, the container 70 is shipped by the manufacturer or distributor either individually, as a part of a set of containers 70, or as part of the phacoemulsification system 80. In certain embodiments, several lens cases 18, each containing a different intraocular lens 11, may be packaged, stored, and/or shipped together to a customer or storage location. Each container 70 may contain an intraocular lens 18 having the same optical power as other containers 70. Alternatively, each container 70 may have a predetermined optical power that is different from other containers 70.

Figure 13A:
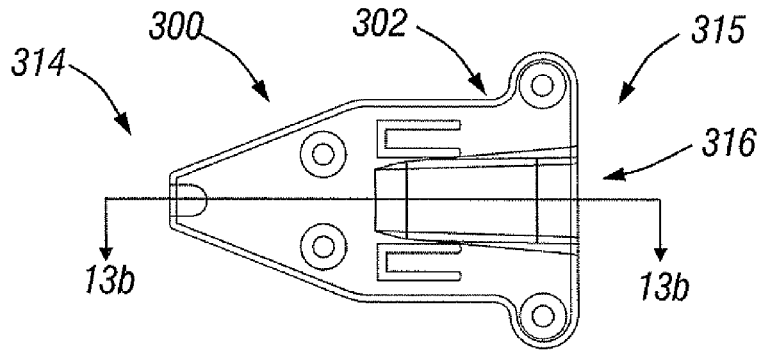
FIG. 13a is a top view of a lens case according to embodiments of the invention for holding an intraocular lens.
Figure 13B:
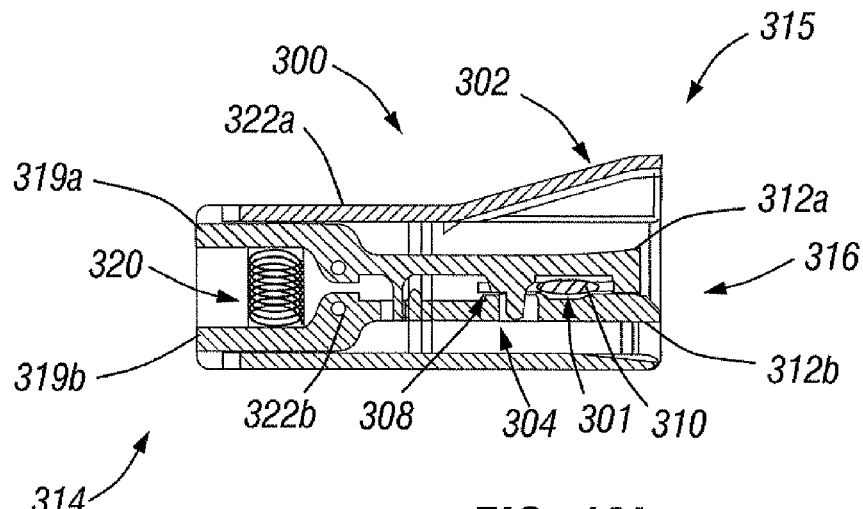
FIG. 13b is a side view of the lens case in FIG. 13a showing a pair of jaws in a closed configuration.
Figure 13C:
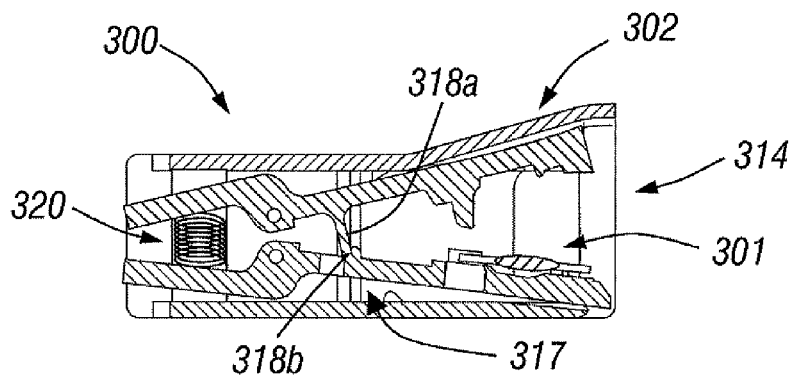
FIG. 13c is a side view of the lens case in FIG. 13a showing a pair of jaws in an open configuration.

Referring to FIGS. 13a-d, in some embodiments a lens case 300, for storing an intraocular lens 301, comprises a housing 302 and a support member 304. The housing 302 is configured for holding the intraocular lens 301 until it is ready to be transferred to the inserter 14 or another inserter configured to engage the lens case 300. The intraocular lens 301 comprises one or more haptics 308 connected to an optic 310. The support member 304 is configured to support the intraocular lens 301 and comprises a plurality of jaws 312, for example the top jaw 312a and the bottom jaw 312b illustrated in FIG. 13b. The jaws 312 have a closed configuration for confining and/or holding the intraocular lens 11, for example as illustrated in FIG. 13b. The jaws 312 also have an open configuration for releasing the intraocular lens 301 that is suitable for transferring the intraocular lens 301 into the inserter 14, for example, as illustrated in FIG. 13c. The lens case 300 is configured for transferring the intraocular lens 301 into the inserter 14 upon or during the process of engagement and/or subsequent disengagement between the lens case 300 and the inserter 14.

The housing 302 generally encloses the intraocular lens 301 and preferably maintains the intraocular lens 301 in a sterile environment until it is ready to be transferred to the inserter 14. The housing may be made of a plastic, metal, or any other material suitable for a surgical environment. The lens case housing 302 and the lens case 300 have a proximal end 314 and a distal end 315. An opening 316 through which the intraocular lens 301 is transferred is disposed on the distal end 315. The housing 302 may have additional openings or windows, for example, for insertion of a viscoelastic or other material, for attachment of other components such as a pusher mechanism, or to provide visibility of intraocular lens 301 and/or support member 304. In some embodiments, the housing 302 and/or the rest of the lens case 300 is disposable. In other embodiments, all or part of the lens case 300 and/or the housing 302 are reusable. In such embodiments, the lens case 300 is configured to allow placement of an intraocular lens into the housing 302 by a user (e.g., a nurse, surgeon, or supplier) and is preferably autoclavable.

The support member 304 and/or the jaws 312 are generally configured to be biased toward a closed configuration, as illustrated, for example, in FIG. 13b. In the closed configuration, the intraocular lens 301 is preferably secured or held so as to prevent damage, for example, during storage, shipping, and/or handling prior to use. The jaws 312 may be configured such that portions of opposing jaws (e.g., portions of top jaw 312a and bottom jaw 312b) are touching and/or pressed against one another when disposed in the closed configuration. In such embodiments, the optic 310 and/or the haptics 312 may be disposed within voids provided between mating faces of opposing jaws 312 when in the closed configuration.

The bias may be overcome, for example when the intraocular lens 301 is to be transferred into the inserter 14, so that the jaws 312 are in an open configuration, for example as illustrated in FIG. 13c. In certain embodiments, the lens case 300 further comprises means for holding or maintaining the jaws 312 in the open configuration once the bias has been overcome. For example, referring to FIG. 13c, the support member 304 may comprise a locking mechanism 317 that maintains the jaws in the open configuration upon engagement between the lens case and the inserter. The locking mechanism may comprise a projection 318a protruding from the top jaw 312a having a distal end that is configured to engage a portion 318b of the bottom jaw 312b when the jaws 312a, b are in the open configuration. Variation on this approach, as well as other devices, principles, and mechanisms, may additionally or alternatively be used to provide the holding means. For example the jaws 312 and/or other portions of the support member may be configured to form magnets that attract more strongly to one another as the jaws 312 move from the closed configuration to the open configuration.

FIG. 13b illustrates one method of providing a predetermined bias for maintaining the jaws 312 in the closed configuration. In such embodiments, the top jaw 312a is pivotally attached to a first arm 319a and the bottom jaw 312b is pivotally attached to a second arm 319b, the bias being produced by a force, for example a spring force, between the arms 319a, b. The bias is produces by a spring 320 that tends to push the arms 319a, 319b away from one another. Pivots 322a, 322b are disposed such that the force pushing the arms 319a, 319b apart also tends to push jaws 312a, b together to produce the desired biasing of the jaws 312 toward the closed configuration. The use of spring 320 is illustrative only and other devices, configurations, and methods of producing the bias toward the closed configuration of the jaws 312 are anticipated. For example, in another embodiment illustrated in FIG. 14a, a top jaw 312a' has a first proximal end 324a and a bottom jaw 312b' has a second proximal end 324b, the first and second proximal ends 324a, b being fixed relative to one another by attachment to a fixed structure 328. The top jaw 312a' and the bottom jaw 312b' are made of a resilient material and are disposed relative to one another so as to produce a bias toward a closed configuration. The jaws 312' may be moved to an open configuration by overcoming the bias force, as illustrated in FIG. 14b.

Figure 15:
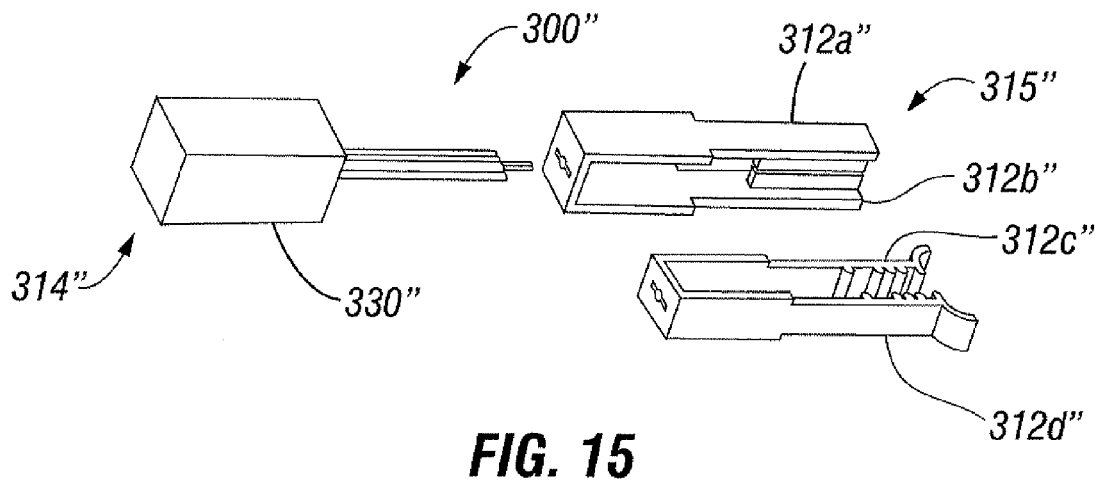

Referring to FIG. 15, in certain embodiments, a lens case 300" comprises four jaws 312", for examples top jaw 312a", bottom jaw 312b", right jaw 312c" (as seen from a distal end 315"), and left jaw 312d". The additional jaws 312", as compared to the two jaws 312 for lens case 300, may be used to provide additional stability and/or protection of the intraocular lens 11. In certain embodiments, additional jaws 312" may be used to provide enhanced performance during delivery of the intraocular lens 301 to the inserter 14. The lens case 300" also comprises a triggering device 330". The triggering device 330" may be configured to be a push member that is used deliver or aid in the delivery of the intraocular lens 301 into the inserter 14 by pushing the intraocular lens 301 towards the distal end 315" of the lens case 300". In certain embodiments, the triggering device 330" may additionally or alternatively be configured to perform other functions, for example to move or hold one or more of the haptics 308 in a preferred position or configuration, as discussed in greater detail below. In some embodiments, the triggering device 330" may be a tab that is pulled, rotated, twisted, or otherwise moved to provide a predetermined action. In yet other embodiments, the triggering device 330" may be a cap that is used to perform a predetermined function while simultaneously providing an opening in the lens case 300". For example, the cap 330" may be disposed at the distal end 315" of the lens case 300" in order to simultaneously provide an opening for the delivery of the intraocular lens 301 and move one or more haptics 315 to a predetermined position or configuration.

In some instances, it is desirable to control the location of the haptics of an intraocular lens during loading of the intraocular lens into the inserter and/or as the intraocular lens is compress during injection into an eye. This may become especially desirable in the case of so called one-piece IOLs in which the haptics are typically made of softer less rigid materials that may become twisted or poorly positioned when the IOL is compressed during insertion. This can be particularly problematic with a trailing haptic, which is more likely to come into contact with the inserter tip and can, therefore, become damaged or torn by the inserter. In such situations, it may be desirable to place at least the trailing haptic above or below the optic of the IOL so that it does not come into contact with the inserter tip during insertion into the eye.

Figure 16A:
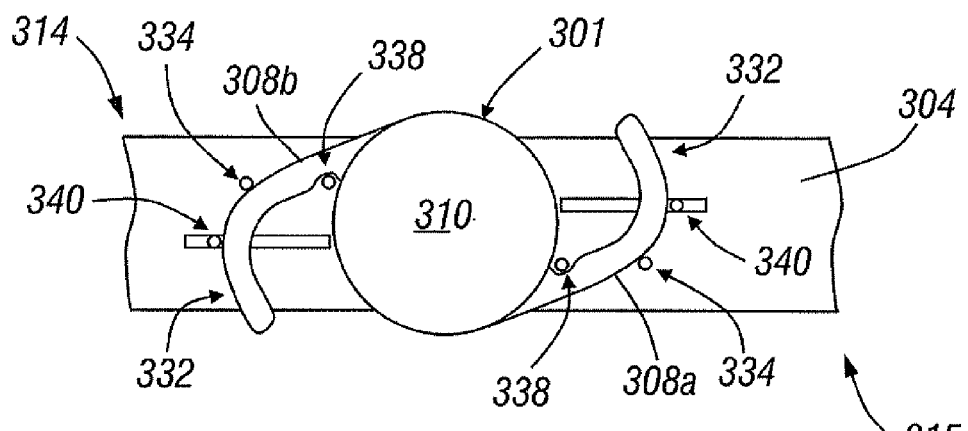
FIG. 16a, b is a top of another embodiment of a lens case according to the invention showing means for moving at least one haptic.
Figure 16B:
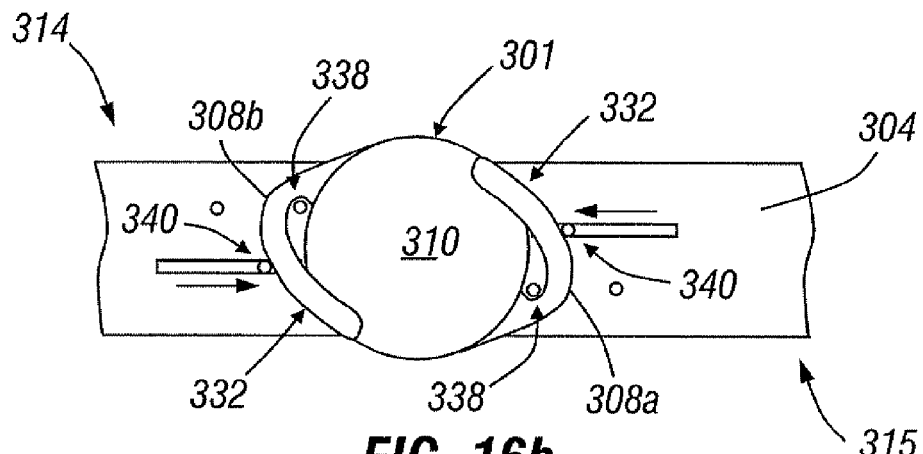
FIG. 16c is a side view of the lens case shown in FIGS. 16a, b.
Figure 16C:
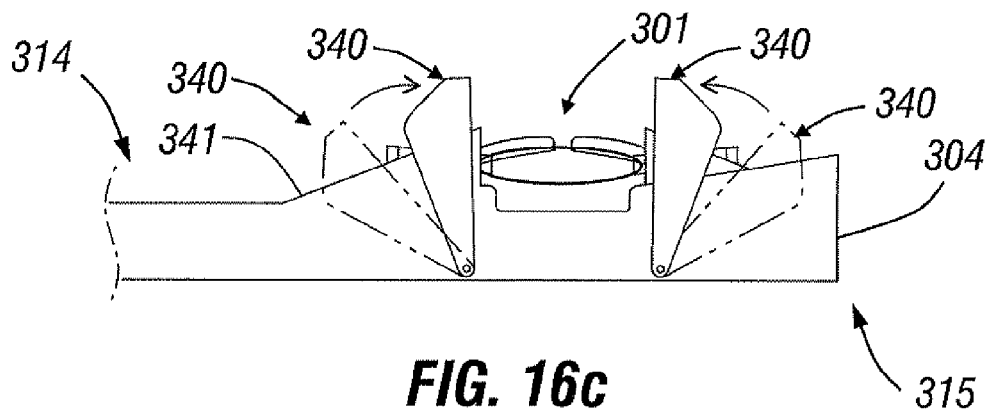

Referring to FIGS. 16a-16c, in certain embodiments, the lens case 300 is configured to place and maintain a distal portion 332 of at least one of the haptics 308 either above or below the optic 310. In the illustrated embodiment, the intraocular lens 301 comprises a leading haptic 308a and a trailing haptic 308b. The lens case 300 is used to place and maintain the distal portion 332 of the haptic 308 in either a first position (e.g., a storage position) in which the distal portion 332 of the haptic 308 is disposed farther from the optic 310, as illustrated in FIG. 16a, or a second position (e.g., a delivery position) in which the distal portion 332 of the haptic 308 is disposed closer to optic, as illustrated in FIG. 16b. Preferably, the storage position leaves the intraocular lens 301 in an unstressed or low stress condition so that the lens 310 does not become deformed during long storage periods in the lens case 300, which can result in degradation of the optical performance of the intraocular lens 11. Prior to insertion, the haptic 308 and/or the optic 310 are temporary placed in a higher stress condition in order prevent the haptic 308 from becoming damaged during insertion into the eye. The lens case 300 is generally configured to move the distal portion 332 of the haptic 308 to the delivery position during or in preparation for transfer of the intraocular lens 301 into the inserter 14. Thus, the lens case 300 is able to automatically move the haptic 308 from the storage position to the delivery position either as the lens case 300 engages the inserter 14 or just prior to engagement by using means such as those discussed herein.

In the currently illustrated embodiment, the support member 304 of the lens case 300 comprises a pair of gripper pins 334 and a pair of folding pins 338. The pins 334, 338 may be used help rotationally stabilize the intraocular lens 301 and may be configured to retract when the intraocular lens 301 is ready to be transferred to the inserter 14. The folding pins may act as pivot points around which the haptics 308 rotate as they are moved from the storage position to the delivery position shown in FIGS. 16a and 16b, respectively. The support member 304 further comprises one or more actuating pins or arms 340 that are moved to place the distal portion 332 of the haptic 308 closer to or over the optic 310 of the intraocular lens 11. In the illustrated embodiment, the support member 304 of the lens case 300 features one or more ramp surfaces 341 that extend between the haptic 308 being moved and the optic 310. The ramp surface 341 rises up to a level above the optic 310 at the edge of the optic. Movement of the actuating arm 340 as seen in FIG. 16c cams the haptic 308 up the ramp surface 341 and on top of the optic 310. The combination of the actuating arm 340 and ramp surface 341 therefore acts as a haptic folder.

In some embodiments, as illustrated in FIGS. 16b and 16c, the distal portions 332 of both the leading and trailing haptics 308a, 308b are disposed over the outer portions of the optic 310. Alternatively, only the distal portion 332 of the leading haptic 308a or of the trailing haptic 308b are disposed over the optic 310. In other embodiments, the distal portion 332 of only one of the haptics 308 is initially placed over or near the optic 310 in preparation for transfer of the intraocular lens 301 to the inserter 14, while the distal portion 332 of the remaining haptic 308 is disposed over or near the optic 310 during or after the transfer of the intraocular lens 11. The distal portion 332 or some other portion of at least one of the haptics 308 may be place near, above, or below the optic 310. The portion of the haptic 308 may be disposed at the periphery of the optic 310 of the intraocular lens 301 or closer to the center of the optic 310. Other locations of portions of the haptic 308 are consistent with embodiments of the invention in which the haptic 308 is favorably positioned to protect the haptic during transfer to the inserter 14 and/or during insertion into the eye of a subject.

Figure 17A:
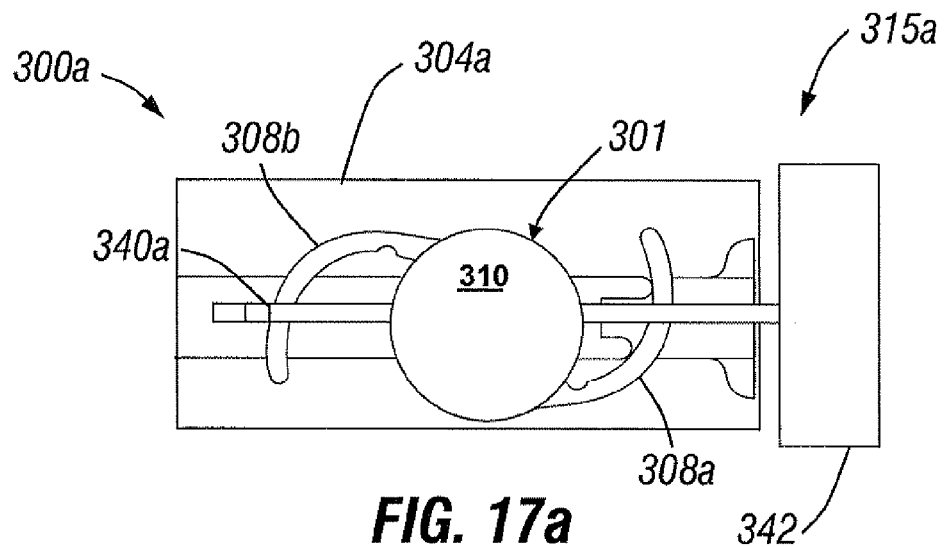
FIG. 17a is a top view of another embodiment of a lens case according to the invention showing a cap for moving at least one haptic.
Figure 17B:
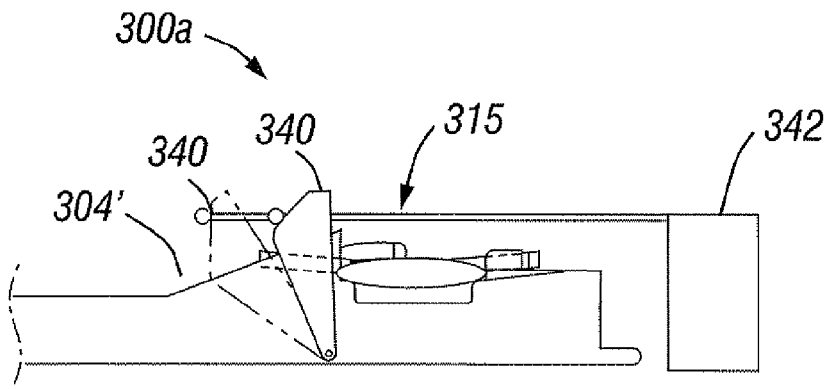

Actuation of the movement of one or more of the haptics 308 may be provided by engagement and/or disengagement between the lens case 300 and the inserter 14. Alternatively or additionally, the lens case 300 may comprise a triggering device or means that is used to actuate movement of a portion of one or more of the haptics 308 from the initial storage position to the final delivery position. For example, FIGS. 17a and 17b illustrate an embodiment in which a lens case 300a comprises a support member 304a and a cap or cover 342 that is disposed at a distal end 315a of the lens case 300a. The cap 342 is configured to cover an opening of a housing (not shown) and is connected by a tether 344 or some other means to an actuating arm 340a. When the intraocular lens 301 is ready to be transferred, the cap 342 is removed so as to expose the opening and move the actuating arm 340a so as to place one or more of the haptic 308 to a predetermined location or orientation. FIG. 17b illustrates the two positions of the actuating arm 340a (i.e., before and after removal of the cap 342). Alternatively, the triggering device may be something other than the cap 342, for example a tab or push member or other device that is engaged by a user to initiate movement of the haptics from a storage position to a delivery position.

Referring to FIGS. 18a and 18b, which each show top and side views of a lens case 300b, a cap 342b may be used to actuate positioning of the haptics 308 by coupling the cap 342b to rotation device 348 to which the actuating arms 340' are attached. In this embodiment, the rotation device 348 is held in an initial position by the cap 342b in which the haptics 308 are in a predetermined low-stress configuration. When the cap 342b is removed, the rotation device 348 is allowed to rotate to a final biased position (e.g., delivery position) in which the actuating arms 340' rotate the entire intraocular lens 301 so as to wrap both the leading and trailing haptics 308 about the optic 310.

Figure 20:
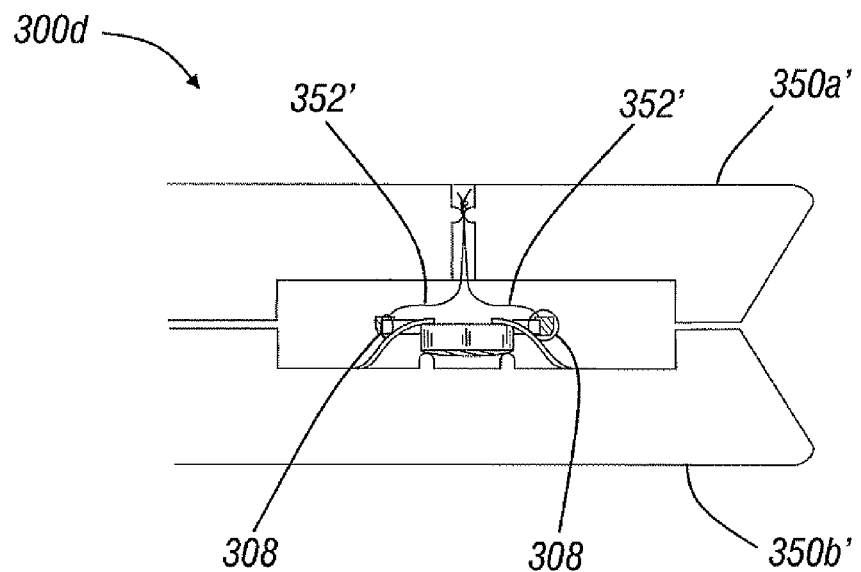
FIG. 20 is a side view of another embodiment of a lens case according to the invention showing two chords configured to move the haptics of an intraocular lens.

Referring to FIG. 19, in some embodiments, movement of one or more of the haptics 308 to a delivery position, in which the haptics 308 are more favorably disposed for insertion into the eye, may be accomplished as a lens case 300c engages the inserter 14. A lens case 300c comprises upper and lower jaws 350a, 350b and a thread, cord, or foil 352. The two ends of the thread, cord, or foil 352 are attached to the upper jaw 350a and are wrapped around one or more of the haptics 308 so that when the jaws 350 are separated, the foil 352 moves the one or more haptics into a delivery position in preparation for insertion into an eye. In some embodiments, as illustrated in FIG. 20, a lens case 300d comprises one or more threads, cords, or foils 352' that are attached at one end to an upper jaw 350a'. The other end of the threads, cords, or foils 352' are wrapped around or otherwise engaged with one or more of the haptics 308 of the intraocular lens 11. Similar to the previous embodiment when the upper and lower jaws 350a', 350b' are separated, the threads, cords, or foils 352' move the one or more haptics into a delivery position suitable for insertion of the intraocular lens 301 into an eye.

Figure 21:
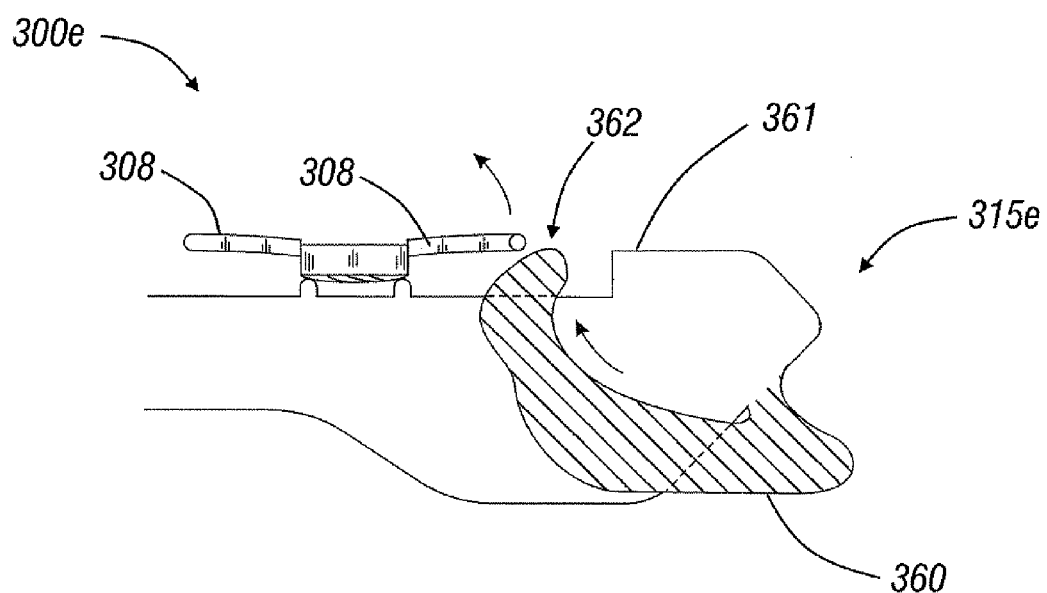
FIG. 21 is a side view of another embodiment of a lens case according to the invention showing a finger configured to move the haptics of an intraocular lens.
Figure 22:
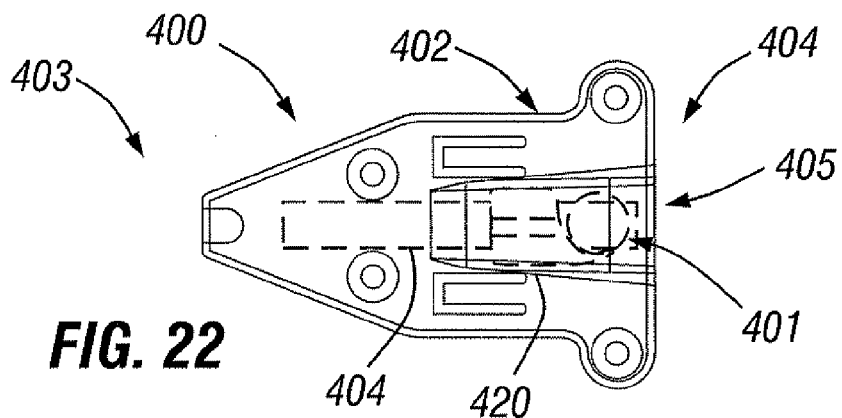
FIG. 22 is a top view of another embodiment of a lens case according to the invention comprising a haptic folder or manipulator configured to move the haptics of an intraocular lens relative to the optic thereof.

Referring to FIG. 21, in some embodiments, a lens case 300e comprises a protruding finger 360 attached to a distal end 315e of a housing and/or support member 361 of the lens case 300e. A distal end 362 of the finger 360 is configured to engage one or more of the haptics 308 of the intraocular lens 11, so as to move the one or more haptics 308 into a delivery position suitable for insertion of the intraocular lens 301 into an eye. Actuation of the finger 360 may be initiated by engagement of the distal end 315e with the inserter 14 or some other object configured for that purpose.

Referring to FIGS. 22 and 23a-d, in certain embodiments, a lens case 400 for storing an intraocular lens 401 comprises a housing 402, a support member 404, a proximal end 403, a distal end 404, and an opening 405 disposed at the distal end 404 and configured to engage an inserter such as the inserter 14. The intraocular lens 401 comprises an optic 410a attached to leading haptic 408a and a trailing haptic 408b. The trailing haptic includes a distal end 409. The lens case 400 also comprises a haptic manipulator or haptic folder 411 that is configured to engage and manipulate at least one of the haptics 408a, 408b. The haptic folder 411 may comprise one or more detents 412 or similar such structures that are configured to engage mating indentations in the lens case 400 or a component disposed therein. The detents 412 may be configured to generally provided resistance to motion of the haptic folder 411 within the lens case 400 and/or to fix or hold the haptic folder 411 at a predetermined location within the lens case 400 during the process of transferring of the intraocular lens 401 into an inserter and/or inserter cartridge. The haptic folder is generally configured to engage at least one of the haptic 408a, b and/or to hold, carry, and/or push the intraocular lens 401. In the illustrated embodiment, engagement of the distal portion 409 of the trailing haptic 408b is provided by a protrusion or finger 413.

Figure 23A:
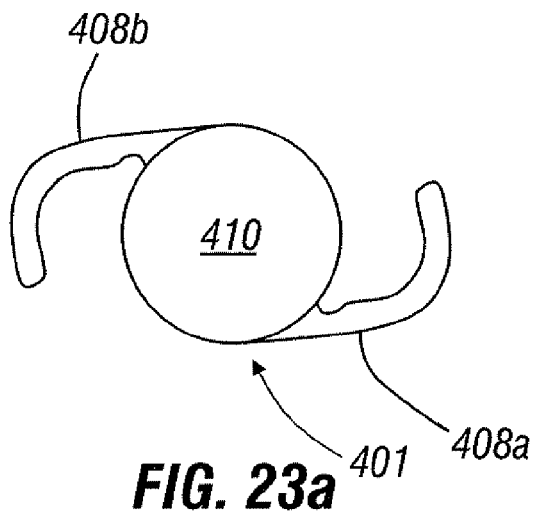
FIG. 23a is a top view of an intraocular lens for use in the lens case illustrated in FIG. 22.
Figure 23B:
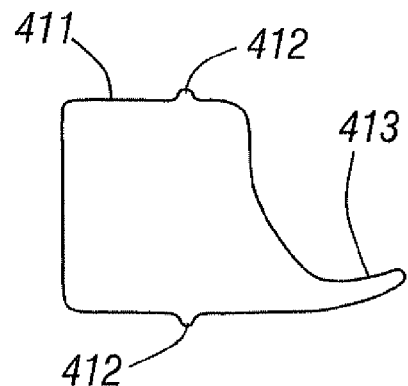
FIG. 23b-d are various views and embodiments of a haptic folder illustrated in FIG. 22.
Figure 23C:
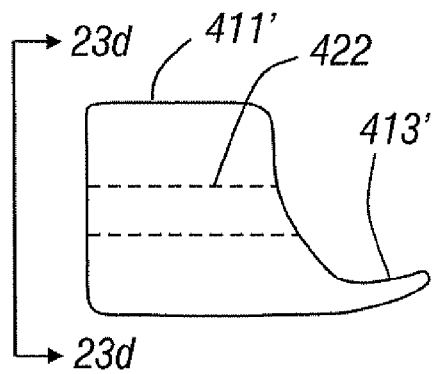
Figure 23D:
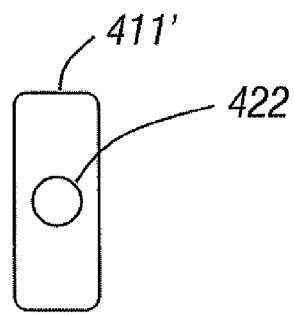

Referring to FIGS. 23c and 23d, in some embodiments haptic folder 411 is a shuttle 411' that is configured to be transferred along with the intraocular lens 401 from the lens case 400 to an inserter or cartridge. For example, the shuttle 411' includes a through hole 422 that is disposed longitudinally along the shuttle 411 and sized so as to allow the push rod of an inserter to pass therethrough, thus allowing the pushrod tip access to the intraocular lens 401 when the intraocular lens 401 and the shuttle 411' are disposed within the inserter.

Figure 24A:
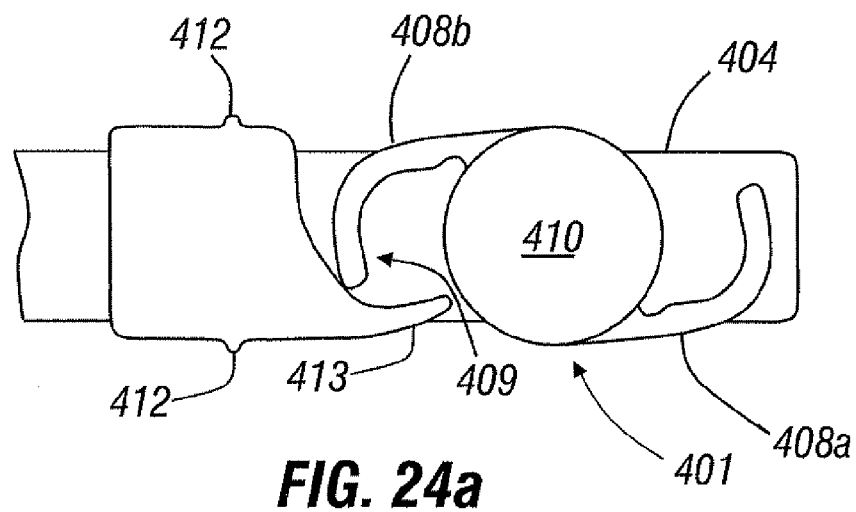
FIG. 24a-c are top views of the haptic folder or manipulator shown in FIG. 23a showing interaction with an intraocular lens.
Figure 24B:
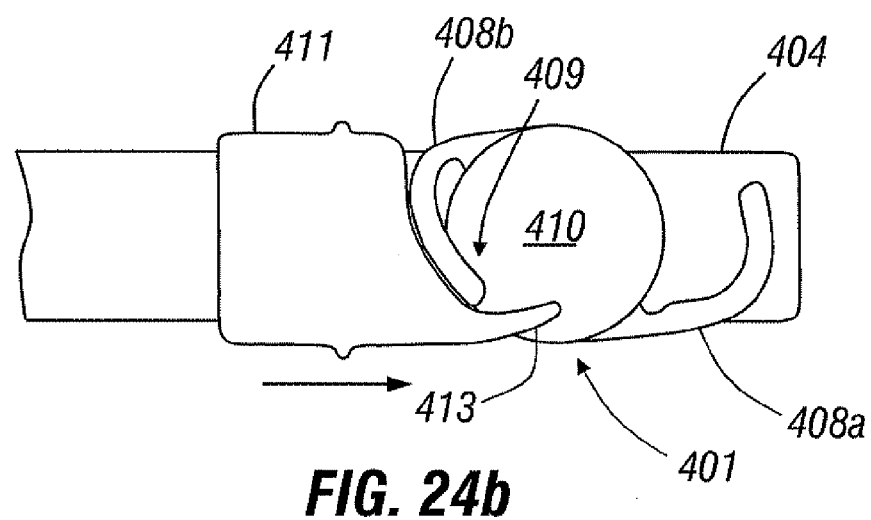

Referring to FIGS. 24a and 24b, in some embodiments the haptic folder 411 is configured to engage and move the haptic 408b to a predetermined position or configuration relative to the optic 410. In the illustrated embodiment, the predetermined position configuration comprises the distal portion 409 of the haptic 408b being positioned over the periphery of the optic 410; however, other locations and configurations of the haptic 408b are possible, as discussed above in relation to the haptics 308. The predetermined position may be any position or configuration of the haptic 408b suitable for preparing the intraocular lens 401 for insertion into an eye using an inserter such as the inserter 14. Any of the devices or means used with the various embodiments of the lens case 300 discussed herein (e.g., those illustrated in FIGS. 16-22) may be used, for example, to actuate the shuttle 411 to move the haptic 408.

Figure 24C:
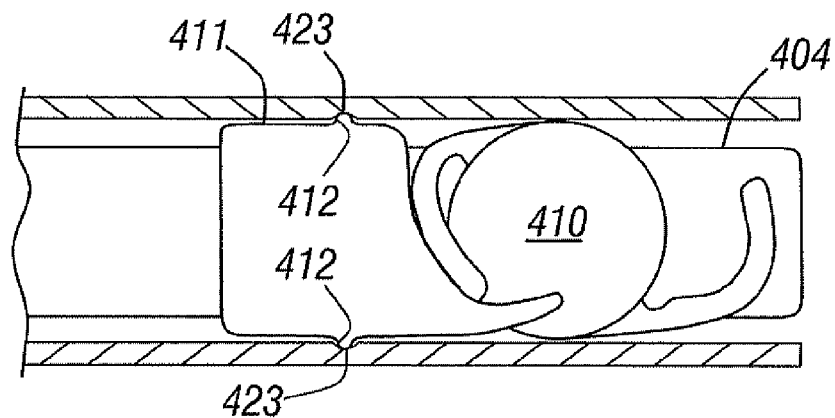

With further referenced to FIG. 24c, the lens case 400 or a fixed surfaced disposed therein may comprise one or more indentations 423 for receiving the detents 412 of the haptic folder 411 when the haptic folder 411 arrives at a predetermined location within the lens case 400. The lens holder is generally configured so that once the trailing haptic is in the predetermined configuration, the detent 412 and the indentations 423 engage one another to prevent or impede further motion of the haptic folder 411 within the lens case 400 (e.g., to prevent the haptic folder from staying with the intraocular lens 401 after disengagement between the lens case 400 and the inserter or cartridge receiving the intraocular lens 401.

Figure 25A:
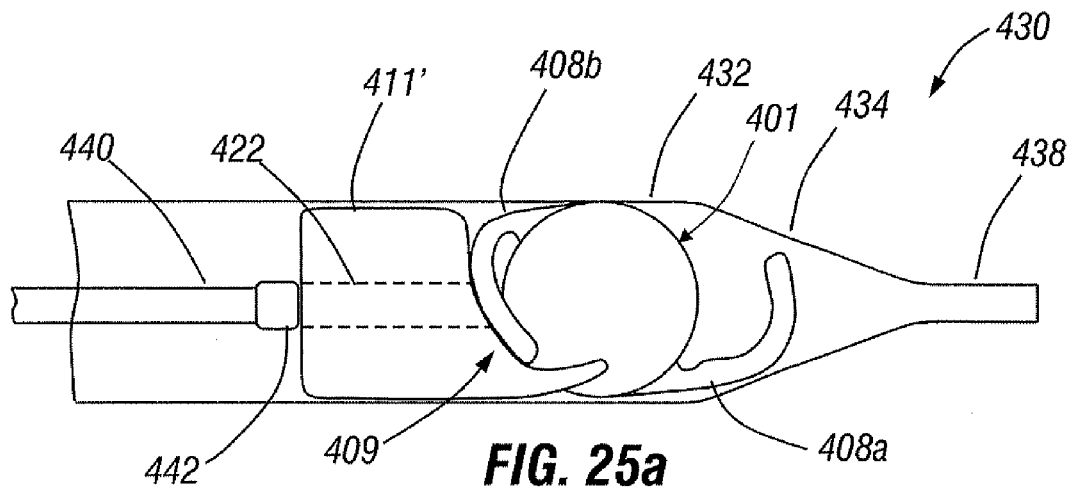
FIG. 25a-c are top views of the haptic folder or manipulator shown in FIG. 23a showing interaction with an intraocular lens inside an inserter.
Figure 25B:
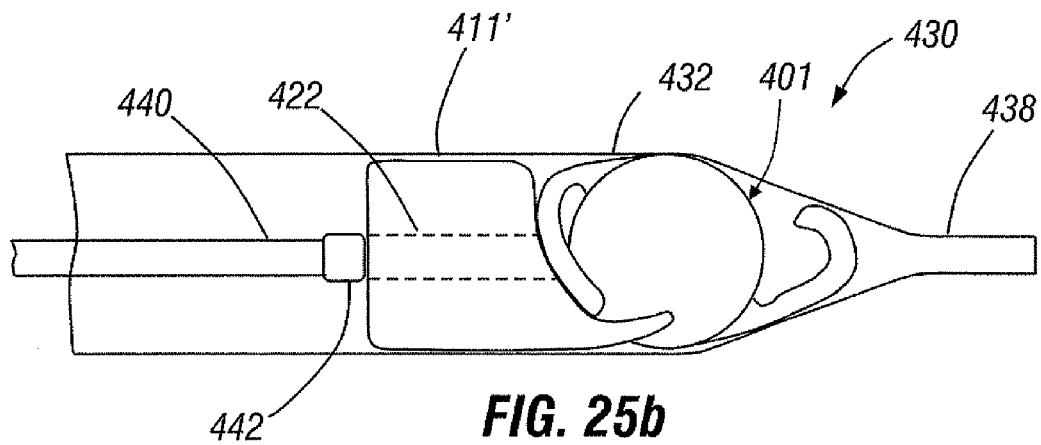
Figure 25C:
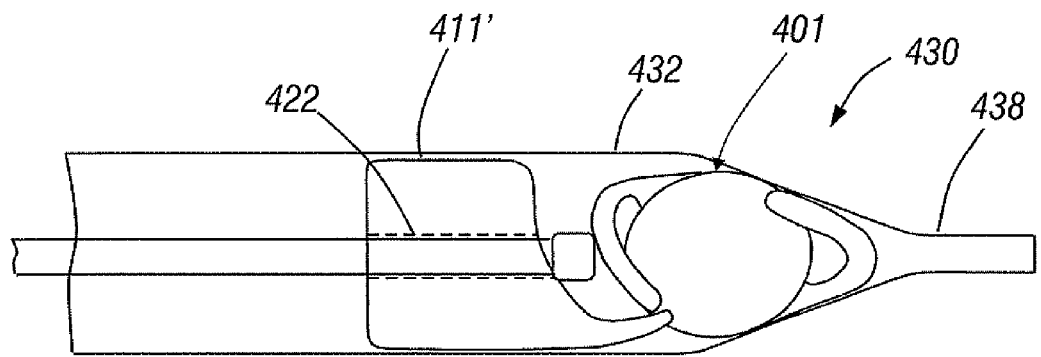

Referring to FIGS. 25a-c, in certain embodiments, the lens case 400 is part of an insertion system comprising the lens case 400, an inserter 430, and the shuttle 411'. The inserter 430 may comprise a receiving, loading, or holding chamber 432, a tapered transition section 434, an insertion tube 438, and a pushrod 440. In one embodiment, the inserter 430 is the handpiece 20 and the holding chamber 432 is the nosepiece 30. In some embodiments, the pushrod may have an enlarged distal tip 442 and/or be made of a softer material. The lens case 400 may be configured to transfer both the intraocular lens 401 and the shuttle 411' together into the inserter 430 (e.g., as in FIG. 25a). In this manner, the shuttle 411' functions both to move the haptic 408b to the predetermined position and to maintain the haptic 408b in that position as the intraocular lens 401 moves from the receiving chamber 432 into the transition section 434 and toward the insertion tube 438. Alternatively, the shuttle 411' may be replaced with a haptic folder that does not stay with the intraocular lens 401 after transfer (e.g., the haptic folder 411 illustrated in FIGS. 24a-c).

As illustrated in FIG. 25b, the distal tip 442 of the pushrod 440 may be sized slightly larger than the diameter of the through-hole 422 of the shuttle 411'. In this manner, the tip 442 of the pushrod 440 does not initially contact the intraocular lens 440 as it is moved toward the insertion tube 438. Other configurations and means may also be used to prevent the initial contact between tip 442 and the intraocular lens 401, such as biasing the tip 442 toward one side of the through hole 422.

Figure 26:
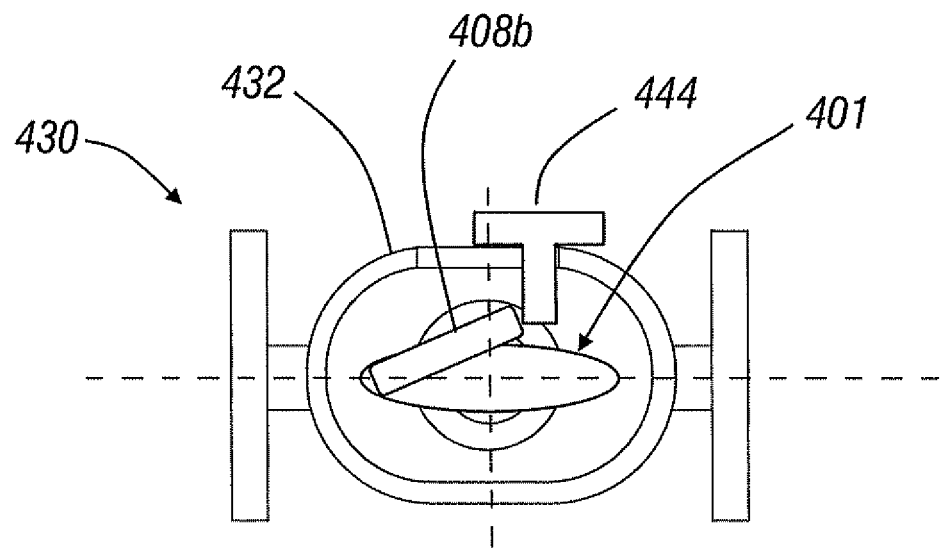
FIG. 26 is an end view of another embodiment of an inserter according to the invention showing a rib for holding the haptics of an intraocular lens.

Referring to FIG. 26, in certain embodiments, a rib or plug 444 may be used in place of or in conjunction with the shuttle 411' (e.g., when using the haptic folder 411) in order to hold the haptic 408b in the predetermined position after the intraocular lens 401 has been transferred to the inserter 430. The rib 444 may be part of the inserter 430, such as the loading chamber 432, and hingedly or otherwise mounted thereon. Once the intraocular lens 401 (and optionally the shuttle 411') is in place in the load chamber 432, the rib 444 is moved into position to hold the haptic 408b in position. Alternatively, the rib 444 may be biased toward its final position and be temporarily displaced slightly as the intraocular lens 401 and/or the shuttle 411' are moved into place inside the receiving chamber.

Figure 27:
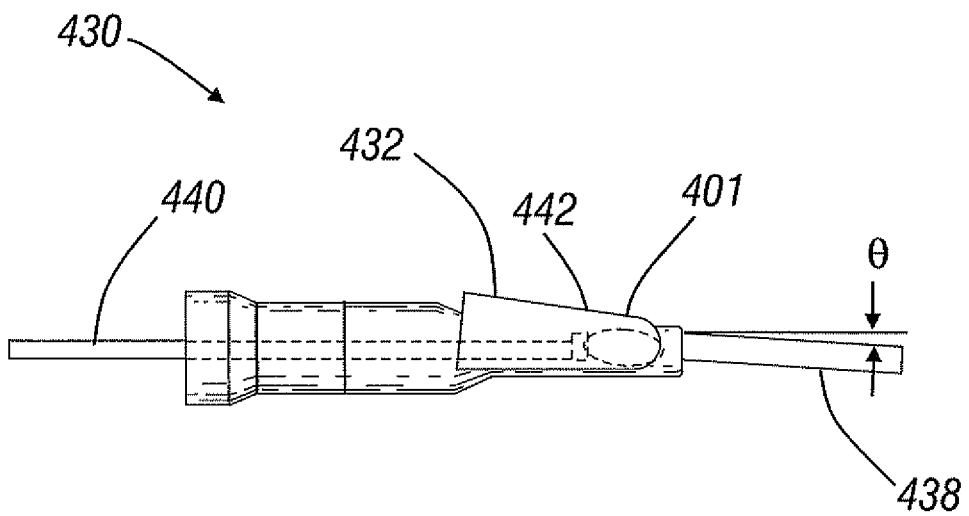
FIG. 27 is a view of another embodiment of an inserter according to the invention showing a sloped insertion tube.

Referring to FIG. 27, in some embodiments, the insertion tube 438 of the inserter 430 may be configured to have a slight angle θ relative to the direction of travel of the pushrod 440. This configuration may be used to help prevent the tip 442 from riding up into the intraocular lens 401 or at least reduce the amount by which the tip 442 rides up into the intraocular lens 401. This may be beneficial, since this type of engagement of the tip 442 with the intraocular lens 401 may damage or even tear the intraocular lens 401. In some embodiments, for example when the tip 442 is made of a relatively soft material, some engagement of the tip 442 may be desirable. The angle θ may be selected to control the amount of engagement of tip 442 with a surface of the intraocular lens 401 as it moves into and through the insertion tube 438. In this sense, engagement between the tip 442 and intraocular Lens 401 refers to interaction between the tip and the anterior surface of the lens.

Figure 28:
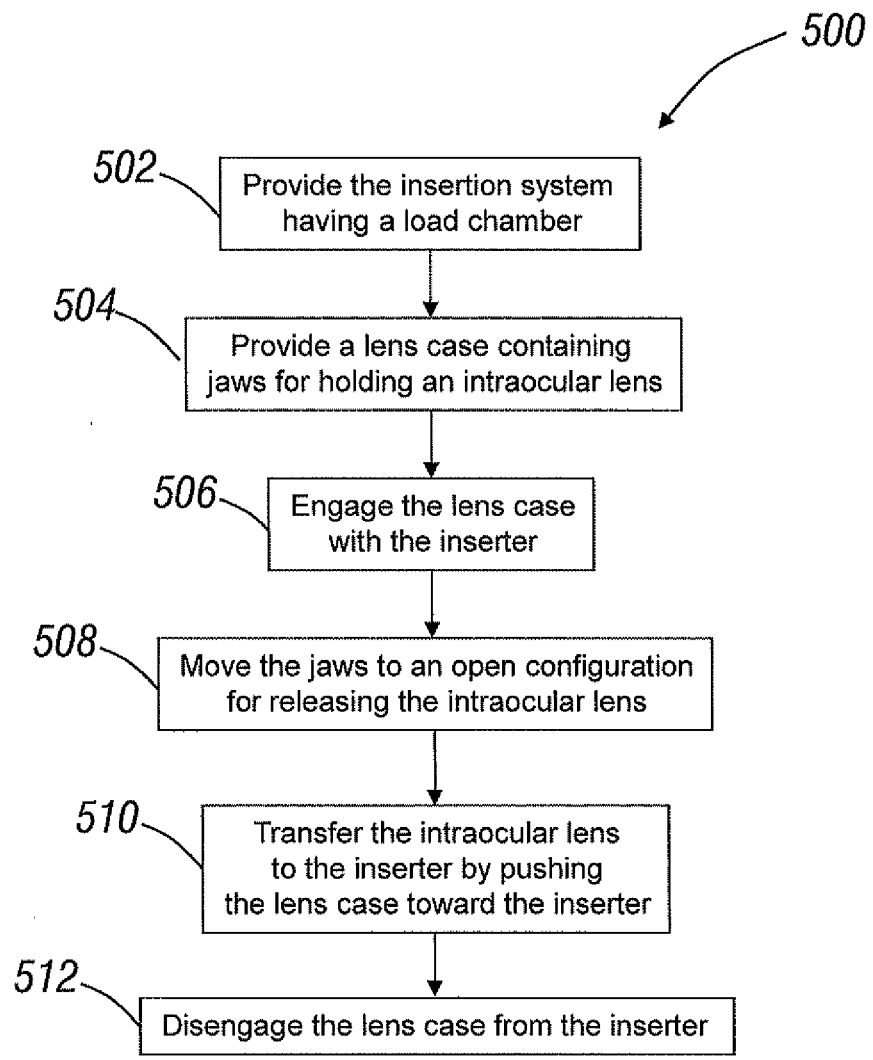
FIG. 28 is a flow chart of a method according to the invention for preparing an intraocular lens for delivery into the eye of a subject.

Referring to FIGS. 28 and 29, a method 500 of preparing transferring an intraocular lens from a lens case to an inserter, in preparation for delivery of the lens into the eye of a subject comprises an operational block 502, which comprises providing the inserter 14 for delivering the intraocular lens 401 into the eye of a subject. The method 500 also comprises an operational block 504, which comprises providing the lens case 300. The method 500 further comprises an operational block 506, which comprises engaging the lens case 300 with the inserter so as to allow transfer of the intraocular lens from the lens case 300 to the inserter. The method 500 additionally comprises an operational block 508, which comprises moving the jaws 312 to an open configuration upon engagement between the lens case and the inserter. The method 500 also comprises an operational block 510, which comprises transferring or pushing the intraocular lens 401 to the inserter 14 by pushing the lens case 300 toward the inserter 14. The method 500 also comprises an operational block 512 that comprises disengaging the lens case from the inserter.

Figure 29A:
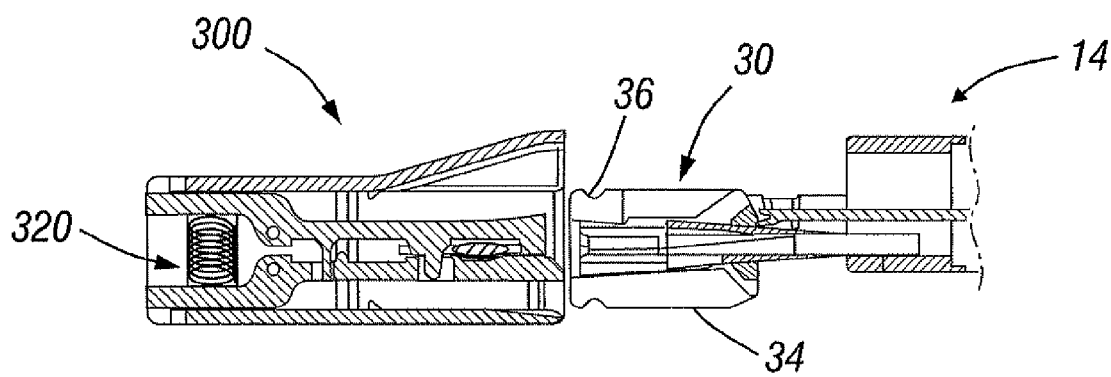
FIG. 29a-d are side views showing use of the lens cartridge shown in FIG. 13a-d.
Figure 29B:
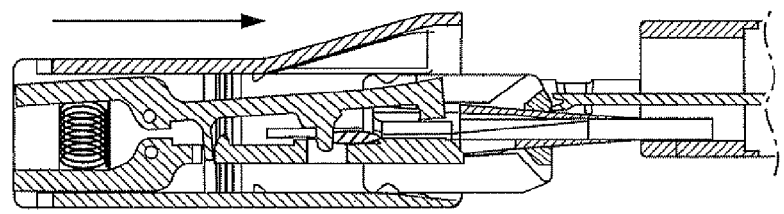

The method 500 may be used, when applicable, in whole or in part with any lens case in accordance with embodiments of the invention, for example the lens cases 300', 300", 300a-e, and 400. The method may also be used with other inserters, such as the inserter 430. Use of the method 500 with the lens case 300 and the inserter 14 is at least partially illustrated in FIGS. 29a-d. In FIG. 29a, the lens case 300 is aligned with the transfer interface 36 of the load chamber 34. In FIG. 29b, the lens case 300 is advanced towards the inserter 14 until the transfer interface 36 begins to engage an opening in the distal end of the lens case 300. In certain embodiments, a cover (not shown) is disposed over an opening in the distal end of the lens case 300 for protection and the cover is removed at the beginning of, or just prior to, the transfer process. Alternatively, the cover may be configured to be removed, punctured, or otherwise opened through engagement of the lens case 300 and the inserter 14.

Figure 29C:
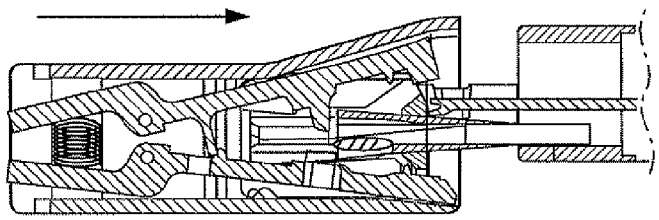
Figure 29D:
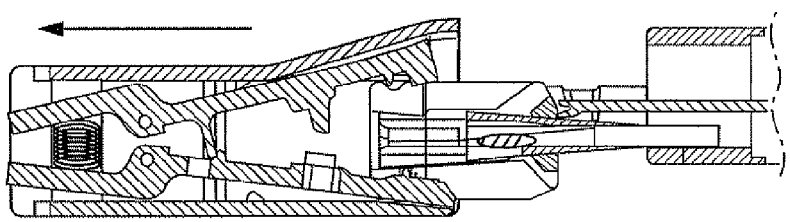

As the lens case 300 and the inserter 14 engage, mating portions on each device (not clearly shown) encourage the upper and lower jaws 312 to begin to open in order to release the intraocular lens 401 for delivery into the inserter 14. In certain embodiments, the leading and/or trailing haptics 308a, 308b are also moved into a delivery position. In other embodiments, the positioning of the haptics 308 is carried out before the engagement between the lens case 300 and the inserter 14, for example as discussed above herein. Referring to FIG. 29c, the lens case 300 is fully engaged and the jaws 312 are fully separated so that the intraocular lens may be deposited inside the load chamber 34. In some embodiments, the locking mechanism 317 (see elements 318a and 318b in FIG. 13c) is provided to maintain the jaws 312 in the open configuration. Referring to FIG. 29d, the lens case 300 is disengaged, leaving the intraocular lens 401 inside the loading chamber 34. Thus, the lens case 300 is configured to deliver the intraocular lens 401 to inserter 14 upon disengagement between the lens case 300 and the inserter 14.

Figure 30:
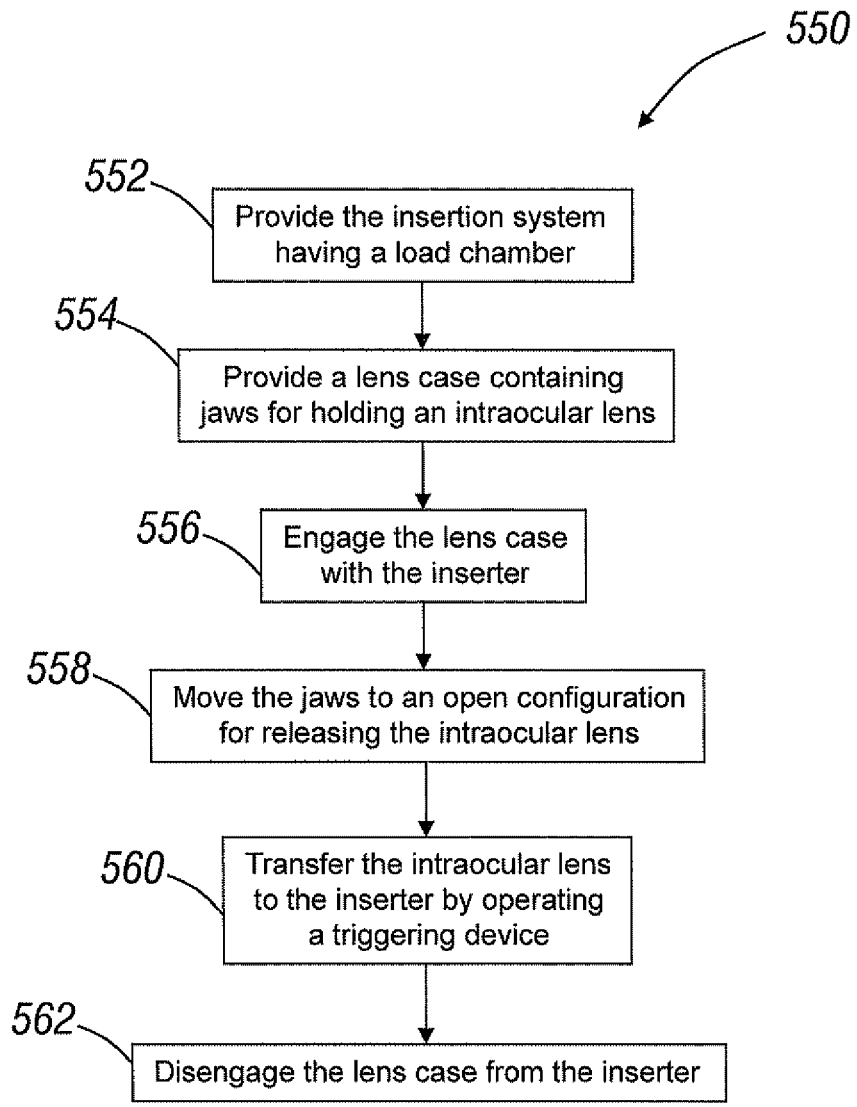
FIG. 30 is a flow chart of another method according to the invention for preparing an intraocular lens for delivery into the eye of a subject.

Referring to FIGS. 30 and 31, a method 550 is illustrated for transferring an intraocular lens from a lens case to an inserter in preparation for delivering the intraocular lens into the eye of a subject. The method 550 is similar to the method 500, except that transfer of the intraocular lens is accomplished by actively operating a triggering device rather than relying on the action of pushing the lens case towards the inserter. Accordingly, the method 500 comprises an operational block 552, which comprises providing the inserter 14 for delivering the intraocular lens 401 into the eye of a subject. The method 550 also comprises an operational block 554, which comprises providing the lens case 300". The method 550 further comprises an operational block 556, which comprises engaging the lens case 300" with the inserter so as to allow transfer of the intraocular lens from the lens case 300" to the inserter. The method 550 additionally comprises an operational block 558, which comprises moving the jaws 312 to an open configuration upon engagement between the lens case and the inserter. The method 550 also comprises an operational block 560, which comprises transferring or pushing the intraocular lens 401 to the inserter 14 by operating the triggering device 330". The method 550 also comprises an operational block 562 that comprises disengaging the lens case from the inserter.

The method 550 may be used, when applicable, in whole or in part with any lens case in accordance with embodiments of the invention, for example the lens cases 300, 300', 300a-e, and 400. The method 550 may also be used with other inserters, such as the inserters 430. FIGS. 31a-d at least partially illustrate use of the one method 550. For each figure, a top view of the lens case 300" and a distal portion of the inserter 14 is shown on top, while a side view of each of these elements is shown directly below. In FIG. 31a, the lens case 300", which contains the intraocular lens 11, is aligned with the transfer interface 36 of the load chamber 34. In FIG. 31b, the lens case 300" is advanced towards the inserter 14 until the transfer interface 36 begins to engage an opening in the distal end of the lens case 300". In certain embodiments, a cover (not shown) is disposed over an opening over the distal end of the lens case 300" for protection, where the cover may be removed at the beginning of, or just prior to, the transfer process of the intraocular lens 11. Alternatively, the cover may be configured to be removed, punctured, or opened through engagement of the lens case 300" and the inserter 14. As the lens case 300" and the inserter 14 engage, mating portions on each device (not clearly shown) cause the jaws 312a", 312b", 312c", and 312d" to open in order to release the intraocular lens 11 for delivery into the inserter 14. In certain embodiments, the leading and/or trailing haptics 308a, b are also moved into a delivery position during the process. Referring to FIG. 31c, the lens case 300" is fully engaged with the inserter 14 and the jaws 312 are fully separated. At this point, the triggering devices 330" may be fully pushed or otherwise manipulated or engaged to advance the intraocular lens 11 into the load chamber 34 of the inserter 14. In some embodiments, a locking mechanism is provided to maintain the jaws 312 in the open configuration. Referring to FIG. 31d, the lens case 300" is disengaged, leaving the intraocular lens 11 inside the loading chamber 34. Thus, the lens case 300" is configured to deliver the intraocular lens 11 to inserter 14 upon disengagement between the lens case 300" and the inserter 14.

The present invention enables a physician or technician to rapidly transfer an intraocular lens (IOL) from a lens storage case directly into an inserter, and then deliver the IOL into a patient's eye using the inserter. During this entire procedure, no forceps or other manual contact with the IOL is necessary. Portions of the intraocular lens, desirably the haptics, may be manipulated during transfer into the inserter from a relaxed configuration to one that is more suitable for insertion into the eye. Furthermore, a manifold that couples to the inserter facilitates introduction of a viscoelastic medium into a load chamber of the inserter. Desirably, the manifold is packaged with the inserter, and the IOL in its case is packaged separately. These two components plus the viscoelastic medium are all that is required for the procedure, other than the standard operating room implements.

FIG. 32 are perspective assembled and exploded views, respectively, of a handpiece 600 of an exemplary inserter according to an embodiment of the invention. The handpiece 600 has a proximal end 602 and a distal end 604. The inserter further comprises a cartridge or nosepiece 606, seen in FIG. 35, coupled to the distal end 604 thereof.

The exemplary handpiece 600 includes a generally tubular barrel 610 having a pair of bifurcated brackets 612 on a distal end thereof for retaining the nosepiece 606. A plunger 614 translates longitudinally within the barrel 610. With reference to the exploded view of FIG. 33 and the detailed views of FIGS. 42-46, the brackets 612 at the distal end of the barrel 610 comprise narrow walls that extend in parallel and define therebetween a transverse space 613 that accommodates rotation of the nosepiece 606, as described below. The transverse space 613 terminates at its proximal end at a radially-oriented face 616. A short tubular dock 618 projects in a distal direction from the face 616 and is configured to receive the tip of a insertion tube of the nosepiece, again as will be described below. A tubular sleeve 620 having indicia thereon such as a directional arrow fits closely over the distal end of the barrel 610 against one or more raised ribs 622 formed thereon. A pair of finger plates 624 project generally radially outward from the proximal end of the barrel 610.

The plunger 614 comprises a shaft-like member with the assembly of a drive cap 630 and cover 632 fixed on a proximal end thereof, and a distal end 634 that engages a pushrod 636. The pushrod 636 terminates at its proximal end in an enlarged head 638 that receives in an axial recess (not shown) the distal end 634 of the plunger 614. The pushrod 636 also features a distal bifurcated tip 640 that contacts and urges the IOL from the inserter during the implant procedure. The shaft-like plunger 614 passes through an annular barrel 642 and piston 644 prior to engagement with the pushrod head 638. An elastomeric O-ring 646 seats within a circular groove in the piston 644 and frictionally engages an inner surface of the barrel 610. The plunger 614 includes a spiral groove 648 that extends the full length thereof and interacts with an inwardly directed pin or tooth 650 in the bore of the piston 644.

FIGS. 34 and 35 are perspective assembled and exploded views of an insertion system 660 according to an embodiment of the invention, wherein the nosepiece 606 connects to the handpiece 600 and a viscoelastic application manifold 662 couples to the nosepiece. As will be explained below, the insertion system 660 receives an intraocular lens (IOL) from a lens case and is then used to surgically insert the IOL into a patients eye. The viscoelastic application manifold 662 facilitates the introduction of a viscoelastic medium, such as sodium hyaluronate, into the nosepiece 606, lubricating the internal passages for proper delivery of the IOL. However, it should be understood that the viscoelastic medium could be applied manually without the manifold 662.

FIGS. 36 and 37 are perspective assembled and exploded views of an exemplary lens case 670 and internal IOL transfer mechanism 672 of the present invention. The lens case 670 comprises a hollow main body 674 having an open end 676 and a cap 678 that mates thereover. The transfer mechanism 672 fits within the main body 674 and is secured therein with structural detents or other such latches. The cap 678 includes a pair of elongated fingers 680 that project through the open end 676 and engage the transfer mechanism 672, as will be explained below. The lens case 670 may be ergonomically shaped with a pair of finger depressions 682 on opposite sides of the main body 674. The user thus grasps the finger depressions 682 and can easily disengage the cap 678 from the main body 674. A pair of longitudinal upper rails 684 project into the hollow interior of the main body 674 toward a pair of longitudinal lower rails 686. The pairs of rails 684, 686 provide positioning walls and help guide the nosepiece 606 into engagement with the transfer mechanism 672, as will be described below. Desirably, the main body 674 and cap 678 are molded of the same rigid transparent polymer, while the parts of the transfer mechanism 672 are molded of a somewhat softer material such as polypropylene. The transfer mechanism 672 snaps into the end of the main body 674 opposite the open end 676.

The IOL transfer mechanism 672 is shown enlarged in FIGS. 38 and 39 with a top jaw 700 pivoted upward to expose internal components thereof. The transfer mechanism comprises a jaw assembly 702 featuring the upper jaw 700 and a lower jaw 704. The upper jaw 700 pivotally couples to the lower jaw 704 at a rear junction 706, and desirably the two jaws are molded as one piece with the junction comprising a living hinge (not shown). As described previously, the jaws 700, 704 include mating faces that define protrusions and voids for receiving and retaining an IOL. The exemplary IOL includes a circular optic 710 having a pair of fixation members or haptics 712a, 712b configured to hold and/or center the optic 710 within the eye. It will be understood by those of skill in the art that the principles of the present invention described herein for storing IOL and transferring it directly to an inserter are applicable to various forms of IOLs, including those with no haptics, a single haptic, or more than two haptics.

The lower jaw 704 defines a generally circular recess 720 within which rests the optic 710. More specifically, leading and trailing partial circular walls that are stepped border the recess 720 and define ledges that support the optic 710 such that the haptics 712a, 712b extend out of the recess. As will be explained below, the jaws 700, 704 close on the IOL such that the haptics 712a, 712b are retained in their relaxed configuration during storage.

The IOL transfer mechanism 672 further includes a haptic support 730, a haptic folder or shuttle 732 and a puller 734. The jaw assembly 702 features a pair of rear brackets 740 that project forward from the rear junction 706. The lower edge of the brackets 740 define edges that cooperate with the lower rails 686 (FIG. 37) on the lens case main body 674. The upper portions of the brackets 740 include a pair of beams 742 that project in parallel to define a longitudinal slot 744 therebetween. The forward end of each of the beams 742 includes inward tapers that narrows the slot 744.

The puller 734 comprises a generally π-shaped member and pair of forward-directed arms 750 connected at a rear bridge 752. Each of the arms 750 features an outwardly-directed lug 754, while a pair of trapezoidally-shaped lugs 756 extend outward from the rear bridge 752. A stepped inner receptacle 760 between the frame arms 750 receives a head portion 770 of the shuttle 732. Preferably, the head portion 770 includes one or more rails or ribs that mate with corresponding features on the frame inner receptacle 760. The shuttle 732 defines a pointed leading end 772 that is offset from the center line of the assembly so as to engage the trailing haptic 712b and fold it over the optic 710, as will be explained. Furthermore, the shuttle 732 has an arrowhead configuration which tapers outward from the pointed leading end 772 to a pair of flexible barbs 774 just before the head portion 770. As explained below, the barbs 774 help transfer the shuttle 732 along with the IOL from the transfer mechanism 672 to the nosepiece 606.

As seen in FIG. 39A, the assembled IOL transfer mechanism 672 includes the IOL positioned within the recess 720, the shuttle 732 received within the receptacle 760 of the puller 734, and the puller positioned such that the trapezoidally-shaped lugs 756 reside within the longitudinal slot 744. In this assembly, the shuttle 732 and puller 734 generally align in a plane that intersects the IOL. The top jaw 700 is shown pivoted upward although prior to assembly within the lens case 670 it would be folded downward to close the jaw assembly 702. In this regard, the top jaw 700 includes features which help retain the IOL and/or haptics 712 in their desired resting positions.

FIG. 39B shows the IOL enlarged and resting on the lower jaw 704. As in the earlier-described embodiments, for example the lens case 300 of FIGS. 16a-16c, the IOL transfer mechanism 672 is capable of configuring one or both haptics 712 as desired to facilitate transfer of the IOL into an inserter and/or into the eye. In the illustrated embodiment, the transfer mechanism 672 engages the trailing haptic 712b and folds it over the optic 710. Most specifically, the leading end 772 of the shuttle 732 translates longitudinally within the transfer mechanism 672 and contacts the trailing haptic 712b to fold it over the optic 710. FIG. 39B shows the position of the shuttle leading end 772 prior to this operation, with the trailing haptic 712b in its first or storage position.

However, prior to actuation, the IOL remains in an unstressed or low stress storage position so that the optic 710 does not become deformed during long storage periods in the lens case 670, which can result in degradation of the optical performance of the IOL. FIG. 39B shows the IOL in its storage position on the lower jaw 704. The IOL rests over the circular recess 720 (FIG. 39A) and is held thereon by a pair of pins 780 that project upward from the lower jaw 704. The pins 780 extend into the innermost corners of the spiral spaces between the optic 710 and haptics 712. Note similar IOL retention pins 780 projecting downward from the upper jaw 700 in FIG. 38.

A leading end of the lower jaw 704 is shaped as a wedge with diverging upper and lower surfaces 782, 784, respectively. One side of the upper surface 782 continues above the level of the IOL and terminates at a post 786 that contacts and restrains the leading haptic 712a. Finally, the haptic support 730 seen in FIG. 38 includes an L-shaped member on its leading end with an upwardly directed finger 788, which can be seen in the enlargement of FIG. 39B. In the storage position of the IOL, the finger 788 projects from below the lower jaw 704 to the level of the IOL and contacts and restrains the trailing haptic 712b as shown.

Movement of the various components of the IOL transfer mechanism 672 to prepare the IOL, and in particular the trailing haptic 712b, for transfer to nosepiece 606 will be explained below with reference to FIGS. 49A-49J. Prior to that discussion, as well as a further discussion of transferring IOL into the patient's eye, a better explanation of the exemplary inserter is necessary.

The inserter 800, seen in the assembled view of FIG. 40 in an IOL transfer mode, comprises the coupled handpiece 600 and nosepiece 606. In this position, the inserter 800 engages the lens case 670 whereupon the IOL is automatically transferred to the nosepiece 606. FIG. 41 is an enlarged perspective exploded view of a distal end of the handpiece 600 and the nosepiece 606, FIGS. 42-46 are various views of the barrel 610 of the handpiece, and FIGS. 47A-47C detail the nosepiece 606.

Reference to FIGS. 41-46, the brackets 612 on the distal end 604 of the handpiece 600 comprise narrow parallel walls defining a transverse space 613 therebetween that receives the nosepiece 606. Each of the brackets 612 defines a leading hook 810 that forms the forward-most border of a side-opening cutout (not numbered) that receives one of a pair of pivot shafts 812 on the nosepiece 606. The nosepiece 606 therefore pivots on the shafts 812 between the brackets 612 and in the space 613. As seen best in the detail of FIG. 46, each cutout is defined by the leading hook 810, a trailing wall 814, and a floor 816. A finger 818 projects away from the floor 816 into the cutout and curves toward the leading hook 810. The curved finger 818, floor 816, and leading hook 810 define a dogbone-shaped slot for receiving one of the nosepiece shafts 812. More particularly, the slot extends from a first enlarged end 820 to a second enlarged end 822. The enlarged slot ends 820, 822 are substantially circular and sized to closely receive the cylindrical pivot shafts 812 of the nosepiece 606. Because of the flexibility of the cantilevered finger 818, the pivot shafts 812 may translate from the first enlarged end 820 to the second enlarged end 822 to enable the nosepiece 606 to pivot. The shape of the slot provides opposite relatively stable resting points (the enlarged ends 820, 822) for the pivot shafts 812. The dogbone-shaped slot therefore provides two bistable positions so that the nosepiece 606 may be "locked" in its storage and IOL-loading position, and then "locked" in a position enabling rotation. Note that a distal tip 824 of the curved finger 818 prevents movement of the shafts 812 in the opposite direction from the second enlarged end 822 back to the first enlarged end 820.

Each of the brackets 812 further includes a square opening 826 extending transversely therethrough. Moreover, inner wall surfaces of the leading hooks 810 are chamfered at corners 828 to facilitate rotational repositioning of the nosepiece 606. FIGS. 43-45 illustrate the short tubular dock 618 that projects in a distal direction from the barrel face 616. Note the stepped end of the dock 618 that will be referenced below. Immediately adjacent to the dock 618, a small through hole 830 in the barrel face 616 provides an opening for the IOL inserter pushrod 636 (FIG. 33).

With reference now to FIGS. 47A-47D further details of the nosepiece 606 of the present invention are shown. The nosepiece 606 includes a delivery channel 840 defined primarily within a distal insertion tube 842 and extending to a proximal load chamber 844 formed within a main body 846. The pivot shafts 812 project in opposite directions from the main body 846 as does a pair of square pegs 848 located just proximal from the shafts. The nosepiece 606 includes a transfer interface 850 at the proximal end of the load chamber 844 for receiving the IOL.

As best seen in the cross-section of FIG. 47D, the insertion tube 842 terminates at a distal delivery port 852 that is formed at an angle much like the end of a hypodermic needle. The insertion tube 842 extends in a proximal direction until connecting with sidewalls 854 of the main body 846. The delivery channel 844 has a distal linear section adjacent the tip 852, but tapers gradually wider toward the main body 846. As with other conventional inserter cartridges, the tapered delivery channel 844 compresses and forms the IOL into an elongated and/or folded configuration suitable for delivery into the eye through the delivery port 852. It is important to note that a lower wall 856 of the insertion tube 842 extends farther axially in a proximal direction than does an upper wall 858. This offset commencement of the insertion tube 842 serves to interact with the IOL transfer mechanism 672 as will be explained.

The sidewalls 854 of the main body 846 primarily define the load chamber 844. As seen from the end view of FIG. 47C, the sidewalls 854 are shaped so as to define a transfer interface 850 that opens to two opposed longitudinal grooves 860. With reference to the dashed line of FIG. 47B, the opposed longitudinal grooves 860 gradually taper toward each other to define the narrowing load chamber 844. Furthermore, the grooves 860 are contiguous with and lead in to the tapered portion of the delivery channel 840. The grooves 860 are initially spaced apart approximately the diameter of the IOL optic 710 so that the optic is easily received within the transfer interface 850. As the IOL travels from a proximal to a distal direction through the load chamber 844 and into the delivery channel 840, the narrowing grooves 860 gradually compress it into the rolled or compressed profile that fits into the generally circular load chamber 844.

FIGS. 48A-48D are partial sectional views of the distal end of the inserter 800 showing the nosepiece 606 coupled to the handpiece 600 in several modes of operation. The handpiece 600 is seen in section so that only the far bracket 612 is visible.

Figure 48A:
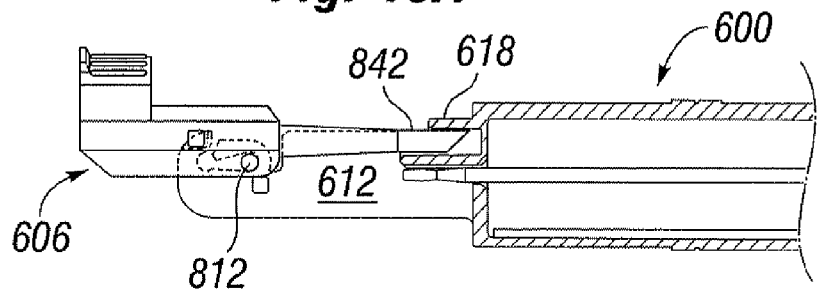
FIGS. 48A-48D are partial sectional views of the distal end of the inserter showing the nosepiece coupled to the handpiece in several modes of operation including an IOL transfer mode and an IOL-delivery mode.

First, FIG. 48A illustrates the nosepiece 606 in a docked or IOL transfer mode. That is, the nosepiece 606 has a first orientation or position in FIG. 48A in which the pivot shafts 812 are positioned at the first enlarged ends 820 (FIG. 46) of the slots defined by the handpiece brackets 612 and the insertion tube 842 extends into the tubular dock 618. Because of the shape of the curved fingers 818, which narrows the central portion of the slot, the pivot shafts 812 and thus the nosepiece 606 are frictionally retained in this position. Contact between the pivot shafts 812 and the right hand side of the slots in the brackets 612, and retention of the distal end of the insertion tube 842 in the dock 618, firmly holds the nosepiece 606 in the first position against compressive forces pushing it against the handpiece 600. It is in the first position in which the inserter 800 comprising the handpiece 600 and nosepiece 606 engage the lens case 670 so as to transfer the IOL therefrom into the load chamber of the nosepiece.

Figure 48B:
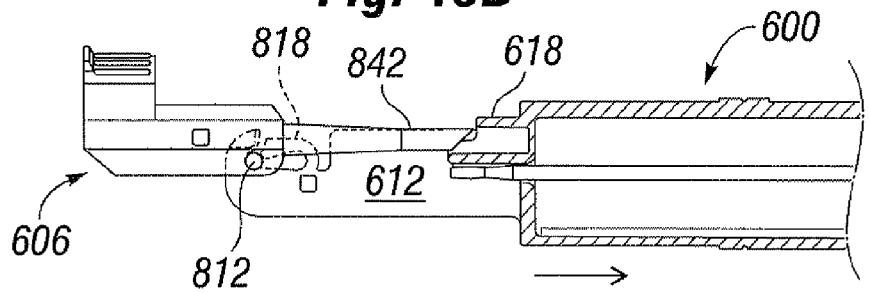

To rotate the nosepiece 606, it is first pulled away from the handpiece 600 as seen in FIG. 48B. Movement of the opposed pivot shafts 812 to the left as shown resiliently flexes the curved fingers 818, which then spring back into their original position as seen in FIG. 46 and retain the pivot shafts 812 in the second enlarged slot positions 822. The resiliency of the fingers 818 produces and audible and tactile snap when pulling the nosepiece 606 away from the handpiece 600. In this position, the insertion tube 842 has retracted far enough to clear the shorter side of the stepped end of the dock 618 (at the top in FIG. 48B). In this position, the insertion tube 842 can be pivoted upward but is restrained from downward motion because of the longer side of the dock 618.

Figure 48C:
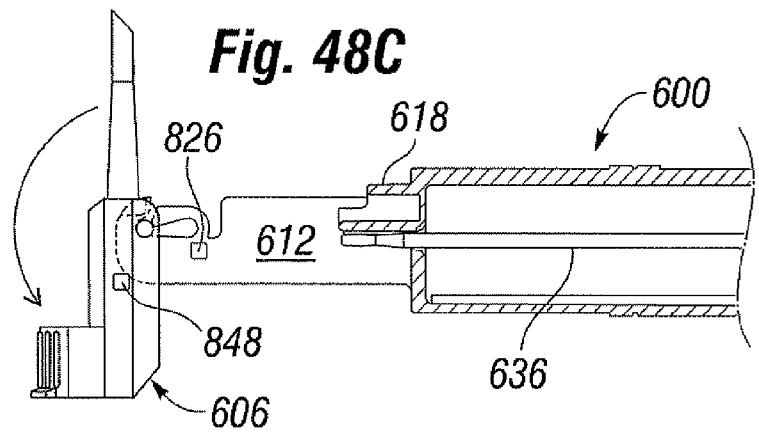

FIG. 48C shows the nosepiece 606 pivoting about the brackets 612 in a counterclockwise direction. It is at this position that the square pegs 848 that project sideways from the nosepiece 606 contact the inside corners 828 of the brackets 612. Because of the chamfered contour of the inside corners 828, as seen in FIGS. 44 and 45, the square pegs 848 continue between and therefore slightly spread apart the bifurcated brackets 612.

Figure 48D:
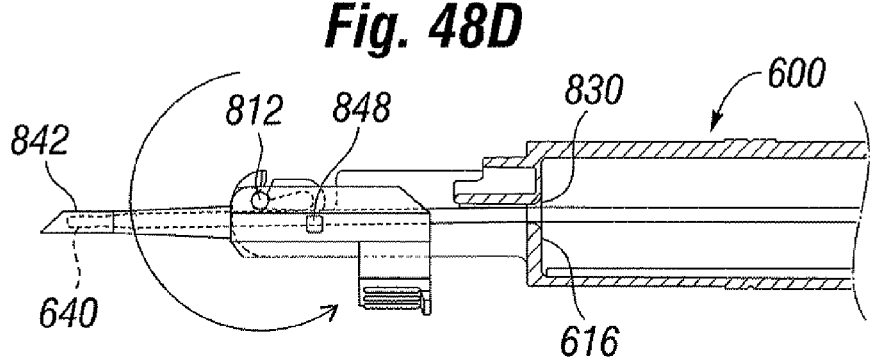

Ultimately, the nosepiece 606 rotates a full 180° into the second position shown in FIG. 48D, and is oriented for delivering the IOL into the eye of a subject. Note that the square pegs 848 on the nosepiece 606 register with and snap into the square holes 826 on the brackets 612 (FIG. 48C). This positive engagement along with the capture of the pivot shafts 812 in the enlarged end 822 of the bracket slot securely holds the nosepiece 606 in the IOL delivery position with the insertion tube 842 extending directly away from the handpiece 600. Note the retracted position of the pushrod 636 in FIG. 48C, and its extended position in FIG. 48D with the bifurcated tip 640 displaced all the way through the nosepiece 606. Indeed, the through hole 830 in the barrel face 616 substantially lines up with the delivery channel within the insertion tube 842, although a slight angular misalignment is acceptable and indeed may be desirable to help urge the IOL through the insertion tube.

Prior to receiving the IOL, the technician must prepare the inserter 800 by applying a viscoelastic medium to the internal passages of the nosepiece 606. Use of a viscoelastic medium such as Healon® sodium hyaluronate is well known in the field, and facilitates passage of the IOL through the inserter by providing optically safe lubrication therein. However in the past the technique involved manually applying the viscoelastic medium using a syringe-like apparatus with a thin cannula tip to apply the substance to the inside of the load chamber. This is a time-consuming and exacting procedure which sometimes results in uneven applications. Accordingly, the present invention provides an improved system and method for applying the viscoelastic medium which enables a speedy, simple, and reliable application.

The inserter 800 of the present invention is desirably packaged with the nosepiece 606 in the first position shown in FIGS. 40 and 48A. The aforementioned viscoelastic application manifold 662 may be packaged on the end of the nosepiece 606 as shown in FIG. 34, or as a separate item. In any event, the manifold 662 has a shape on one side 664 that conforms to the shape of the transfer interface 850 on the nosepiece 606, and the technician places the manifold in the position of FIG. 34. The manifold 662 includes a pair of conically recessed inlet ports 668 leading to internal channels (not shown) within the manifold. The internal channels are shaped and positioned such that a viscoelastic medium injected into the inlet ports 668 is guided thereby into the appropriate spaces within the nosepiece 606. More specifically, the internal channels of the manifold 662 guided the viscoelastic medium into the two opposed longitudinal grooves 860 of the load chamber 844 (see FIG. 47C). Two inlet ports 668 are shown which lead to two internal channels to separately lubricate the longitudinal grooves 860. However, it is conceivable to provide just one inlet port which diverges within the manifold 662 toward the separate grooves 860.

FIGS. 49A-49J illustrate sequential steps in an interaction between the lens case 670 having the IOL transfer mechanism 672 and the nosepiece 606 at the front end of the inserter 800. First, an automatic haptic-positioning feature of the lens case 670 will be described with respect to FIGS. 49A-49C.

Figure 49A:
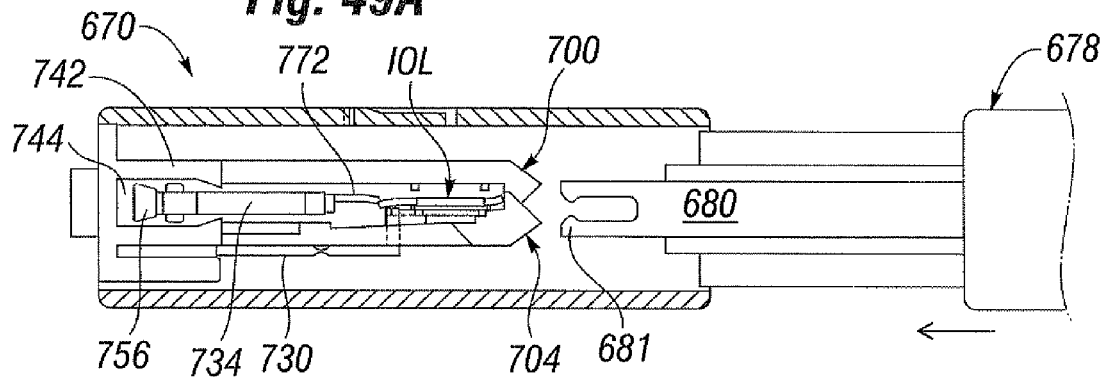
FIGS. 49A-49J are side views of several steps in an interaction between the exemplary intraocular lens (IOL) case with internal IOL transfer mechanism and the IOL-receiving nosepiece.

FIG. 49A shows the lens case 670 holding the IOL within the transfer mechanism 672 and with the end cap 678 slightly detached to the right for clarity. As mentioned, the end cap 678 includes a pair of bifurcated fingers 680. The terminal end of each finger 680 toward the transfer mechanism 672 features a pair of split tongs 681 with inwardly-directed teeth. The transfer mechanism 672 includes the upper and lower jaws 700, 704 in their closed position restraining the IOL. The haptic support 730 resides underneath the lower jaws 704 while the puller 734 is between the jaws. The rear end of the puller 734 including the trapezoidal-shaped lugs 756 slides within the slots 744 defined between the beams 742. The shuttle leading end 772 is just seen extending past the puller 734.

Figure 49B:
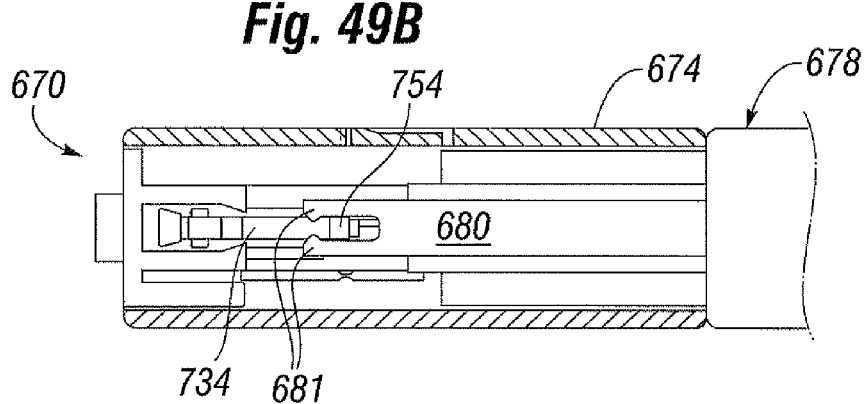

FIG. 49B shows the lens case 670 assembled, with the cap 678 secured to the main body 674. In this position, the elongated fingers 680 are aligned and extend far enough so that the split tongs 681 surround the outwardly-directed lugs 754 of the puller 734. Everything else remains in the same position as seen in FIG. 49A, and the IOL (not shown) remains in its relaxed configuration with the haptics unstressed. It is in this condition that the IOL leaves the manufacturing facility in the appropriate packaging and is not disturbed until just before the surgical IOL implant procedure.

Figure 49C:
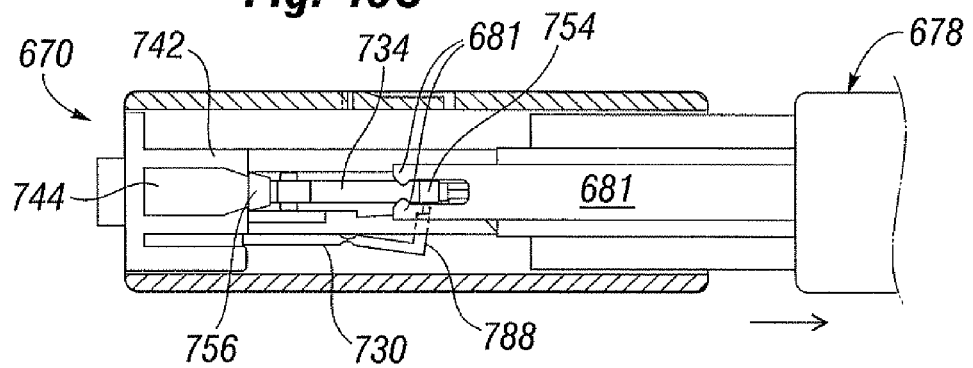

At the time of the procedure, the physician or technician removes the end cap 678 as seen in FIG. 49C. Pulling the end cap 678 off of the main body 674 (to the right in the drawing) displaces both the puller 734 and shuttle therewithin. More particularly, the inwardly-directed teeth of the split tongs 681 grab the outwardly-directed lugs 754 of the puller 734 and pull them to the right, causing the entire puller to translate to the right. Although not shown, guide rails between the jaws 700, 704 insure alignment of the puller 734 during this movement and permit the puller to move far enough so that the trapezoidally-shaped lugs 756 force past the narrow portion of the beams 742 and out of the slot 744. Once the lugs 756 are clear of the slots 744, structure (not shown) on the jaws 700, 704 prevents further movement of the puller 734 to the right. Because the split tongs 681 are resilient they spread apart past the lugs 754 and the cap 670 may be completely removed from the main body 674.

It should also be noted that a portion of the haptic support 730 flexes downward upon the rightward movement of the puller 734 and shuttle. That is, movement of the shuttle 732 first contacts and cams the finger 788 of the haptic support 730 downward, by virtue of it being pivoted about a living hinge. The reader will recall FIG. 39B which shows the finger 788 restraining the trailing haptic 712b. By removing the end cap 678, this restraint is removed automatically.

Figure 49D:
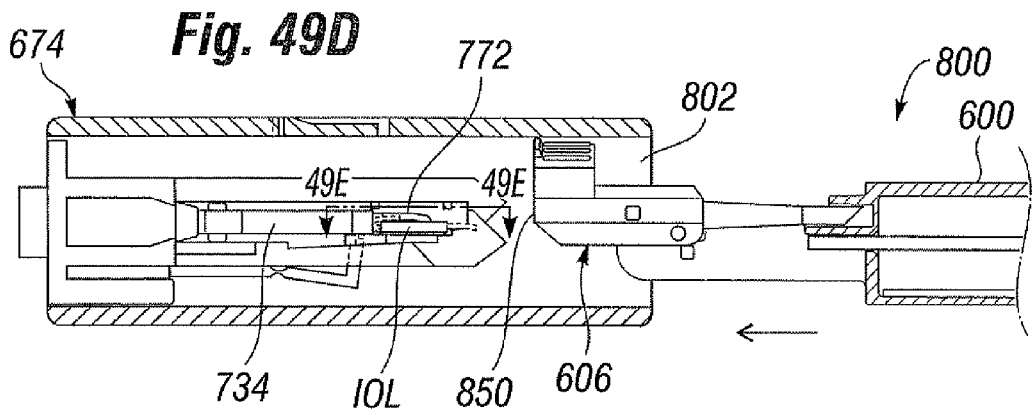
Figure 49E:
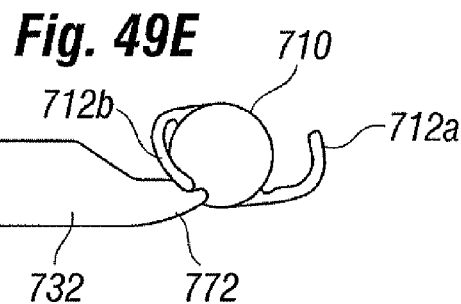

FIG. 49D shows the lens case main body 674 without the lens cap such that a transfer port 802 is exposed. It is through this transfer port 802 that the nosepiece 606 of the inserter 800 projects into engagement with the transfer mechanism 672. Note that the nosepiece 606 is in its first position for loading the IOL with the transfer interface 850 facing away from the handpiece 600.

FIG. 49D illustrates the prepositioned puller 734 and the shuttle leading end 772 relative to the IOL. More particularly, the leading end 772 projects over the optic 710 of the IOL. As seen more clearly from above in the detail of FIG. 49E, the leading end 772 manipulates or folds the trailing haptic 712b over the optic 710. Folding the trailing haptic 712b over the optic 710 in this way facilitates delivery of the IOL from the inserter 800 into the subject's eye. The trailing haptic 712b is temporary placed in a higher stress condition in order prevent it from becoming damaged during insertion into the eye. The trailing haptic 712b remains in this position over the optic 710 throughout the remaining steps of the transfer between the lens case 670 and inserter 800. To ensure this arrangement, the shuttle 732 remains in the position relative to the IOL shown in FIG. 49D through the transfer procedure.

Figure 49F:
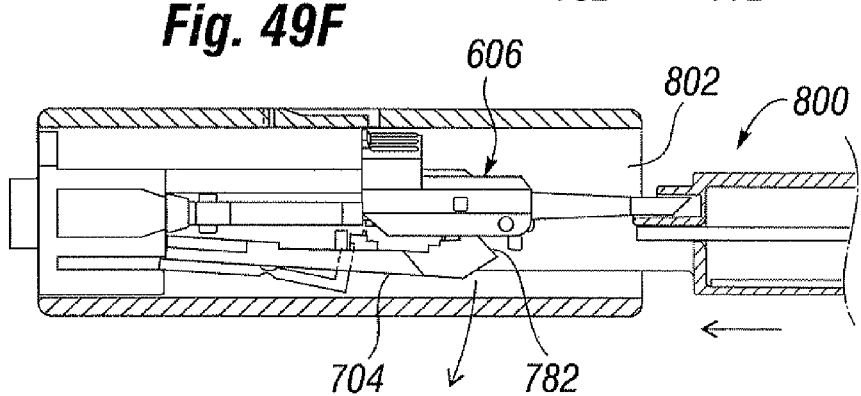

FIG. 49F shows farther advancement of the inserter 800 through the transfer port 802 and illustrates the result of the first contact between the nosepiece 606 and the transfer mechanism 672. The reader will recall from FIG. 47D that the lower wall 856 of the nosepiece insertion tube 842 extends farther axially in a proximal direction than does an upper wall 858. It is the lower wall 856, therefore, that first contacts the wedge-shaped upper surface 782 of the lower jaw 704 and causes it to pivot downward as shown. Prior to this movement, however, it should be understood that the sides of the optic 710 of the IOL are captured by the two opposed longitudinal grooves 860 of the load chamber 844 (see FIG. 47C) of the nosepiece 606. Although not explicitly shown, comparison of the axial position of the IOL in FIG. 49D with the position of the nosepiece 606 in FIG. 49E demonstrates that the IOL is now surrounded by the sidewalls 854. Actually, diametrically opposed edges of the IOL are frictionally held by the viscoelastic medium in the grooves 860, and the IOL is therefore suspended across the sidewalls 854. Pivoting movement of the lower jaw 704 removes all of the remaining restraints and alignment pins from the underside of the IOL.

Figure 49G:
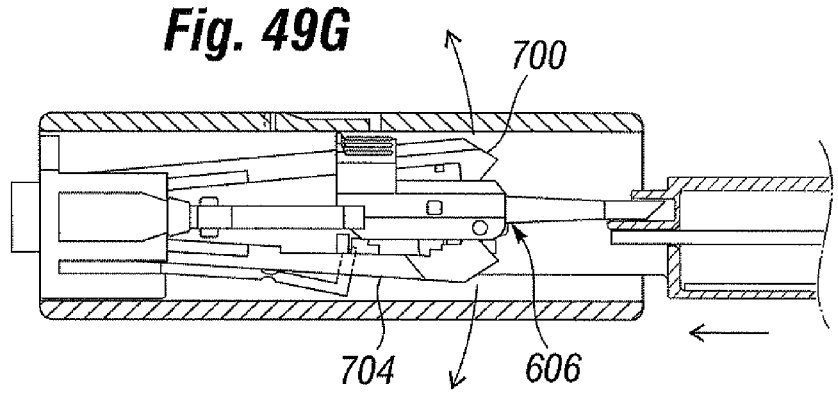

In FIG. 49G, the inserter 800 translates farther to the left so that the nosepiece 606 causes the upper jaw 700 to pivot upward. That is, the upper wall 858 of the nosepiece insertion tube 842 (FIG. 47D) contacts and cams upward the wedge-shaped leading edge of the upper jaw 700. This action removes all of the various restraints and alignment pins from above the IOL. At this stage, the IOL is fully suspended within the nosepiece 606 without any contact with the upper or lower jaws 700, 704.

Figure 49H:
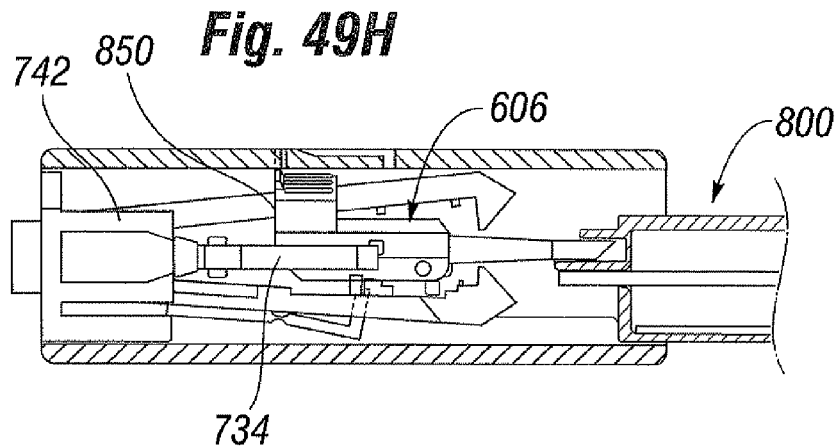

FIG. 49H illustrates full engagement of the inserter 800 with the lens case 670. The nosepiece 606 has translated still farther to the left until it can go no farther, which is desirably accompanied by an audible and tactile click. Ultimately, the edges of the transfer interface 850 at the leading edge of the nosepiece 606 contact the stepped inner receptacle 760 (FIG. 38) of the puller 734 which is braced on its other side by the beams 742. Although not shown in FIG. 49H, the shuttle 732 is also compressed between the nosepiece 606 and the puller 734 such that the flexible barbs 774 (FIG. 38) wedge in between the longitudinal grooves 860 of the nosepiece load chamber 844, while the head portion 770 of the shuttle 732 exceeds size of the opening of the load chamber 844 and remains outside. This position represents complete transfer of the IOL from the lens case 670 to the inserter 800 (indeed, it should be apparent from the preceding discussion that the transfer occurs not suddenly but instead over a short continuum). It is important to note here that though the shuttle 732 transfers along with the IOL from the lens case 670 to the inserter 800, it represents a haptic folder in the general sense (such as at 411 above) within the lens case that configures one or both haptics to facilitate transfer of the IOL, and may remain with the lens case.

Figure 49I:
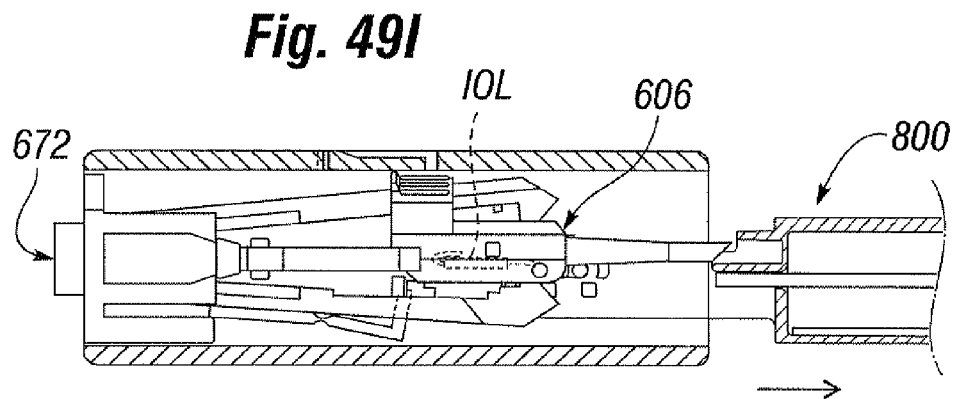

FIG. 49I shows the subsequent retraction of the inserter 800 from the transfer mechanism 672. The nosepiece 606 now contains the IOL and the shuttle 732. Note that pulling the inserter 800 to the right does not initially move the nosepiece 606, such that the bracket 612 move to the right with respect to the pivot shafts 812, as in the step between FIGS. 48A and 48B. The pivot shafts 812 thus transition from the first enlarged end 820 to the second enlarged end 822 in the dog bone-shaped slot, freeing the insertion tube 842 from the dock 618 and permitting subsequent rotation of the nosepiece 606.

Figure 49J:
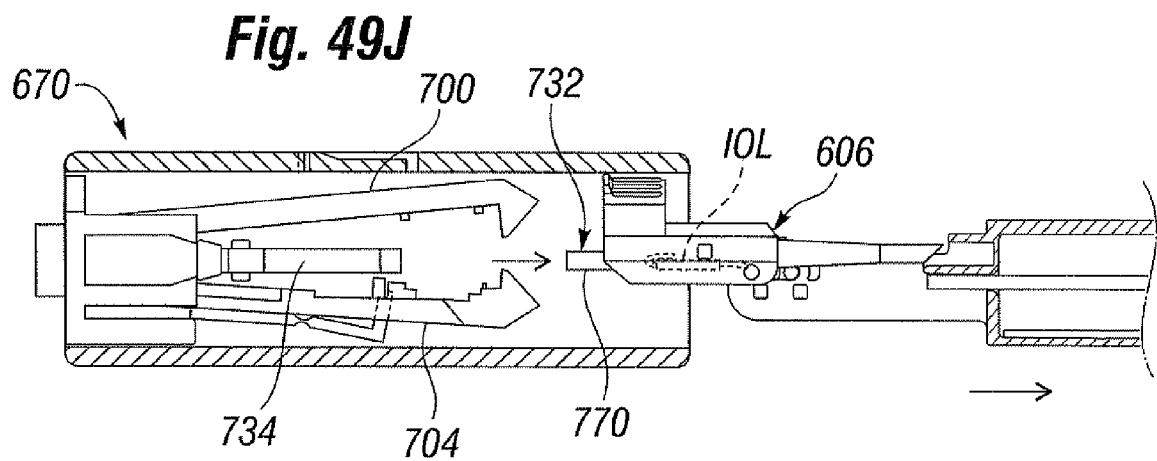

Finally, FIG. 49J shows the inserter 800 with the IOL therein pulling free of the lens case 670. The head portion 770 of the shuttle 732 can be seen projecting out of the nosepiece load chamber 844.

After transfer of the IOL from the lens case 672 the inserter 800, it is necessary to move the nosepiece 606 into its second position for delivering the IOL into the subject's eye. This operation was described previously with respect to FIGS. 48A-48D. Although the head portion 770 of the shuttle 732 projects out of the nosepiece load chamber 844, it will not interfere with rotation of nosepiece 606. Now the inserter 800 with the IOL loaded therein is ready to deliver the IOL to the subjects eye.

Figure 50A:
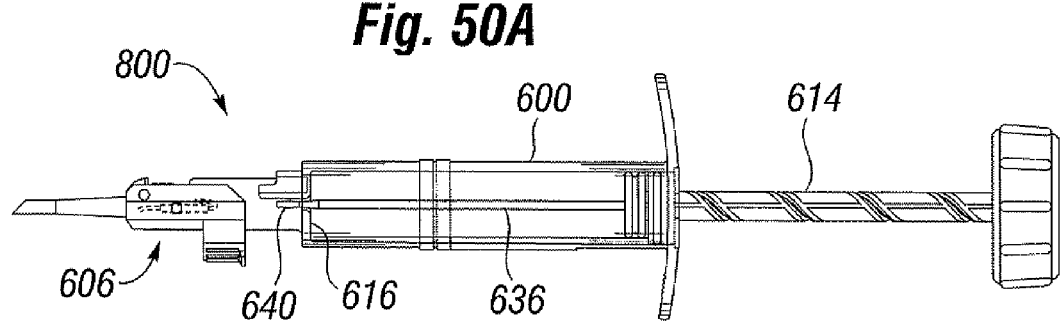
FIGS. 50A-50C are elevational views of several steps in use of the exemplary insertion system to expel an IOL through the nosepiece.
Figure 50B:
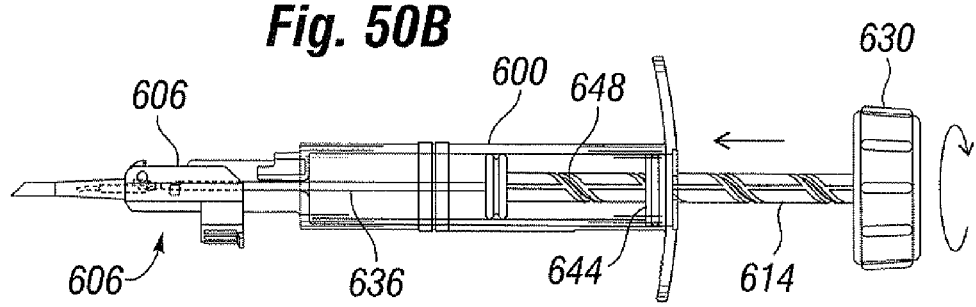
Figure 50C:
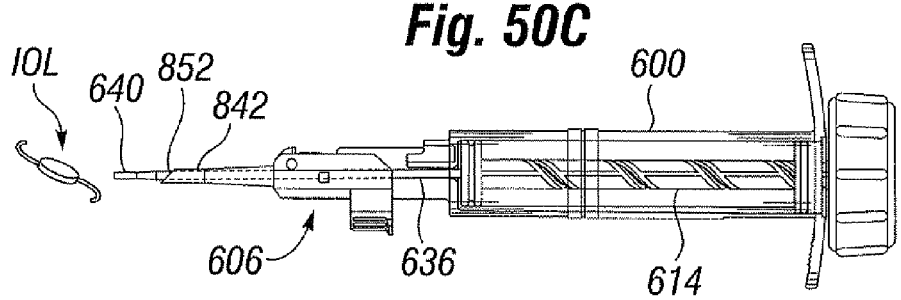

FIGS. 50A-50C are elevational views of several steps in use of the inserter 800 to expel an IOL through the nosepiece 606. FIG. 50A shows the nosepiece 606 in its second position for delivering the IOL, and the plunger 614 of the handpiece 600 fully retracted. In this position, the pushrod 636 remains substantially within the handpiece with the bifurcated tip 640 extending just past the through hole in the barrel face 616 (see also the detail of FIG. 48D).

FIG. 50B shows axial displacement of the plunger 614 and pushrod 636 to the left. As indicated by the circular arrow on the right, the technician displaces the plunger 614 by turning the cap 630 so that the spiral groove 648 interacts with the inwardly directed tooth 650 (FIG. 33) in the bore of the piston 644 and forces the plunger to the left. In this snapshot, the pushrod 636 has entered the load chamber of the nosepiece 606 such that the bifurcated tip 640 contacts and begins to urge the IOL from the inserter. It should be noted that the illustrated embodiment permits the user to choose between advancing the plunger 614 by twisting the cap 630, or more directly by axially depressing the cap 630. In the latter procedure, the piston 644 displaces axially with the plunger 614. In either situation, a ball and socket hinge arrangement between the distal end 634 of the plunger 614 and enlarged head 638 of the pushrod 636 ensures that the two parts relatively rotate and the bifurcated tip 640 remains in a desired orientation.

Finally, in FIG. 50C the plunger 614 has fully translated through the handpiece 600 so that the bifurcated tip 640 clears the distal delivery port 852 and expels the IOL from the insertion tube 842. The final movement of the plunger 614 and pushrod 636 is done extremely carefully so as not to expel the IOL from the end of the insertion tube 842 with any velocity. Indeed, the preferred method is to carefully position a leading haptic and then urge the remainder of the IOL slowly into place without allowing it to spring out.

The various embodiments of IOL insertion systems of the present invention enable rapid transfer of an IOL from a lens case to an inserter, and then into a patient's eye. The insertion system described with reference to FIGS. 32-50 in particular provide a number of conveniences and advantages heretofore unknown in the field. It is worth describing the entire insertion procedure to point out these efficiencies.

After preparing the patient and acquiring the proper IOL and inserter, the physician or technician removes the end cap 678 from the lens case 670. This single movement automatically folds the trailing haptic 712b over the optic 710, as was seen in FIG. 49E. Previously, if manipulation of the haptics was required it would have been done manually with forceps.

The physician applies a viscoelastic medium to the load chamber 844 of the nosepiece 606 (often termed the IOL cartridge in earlier systems). The physician positions the viscoelastic manifold 662 against transfer interface 850 of the nosepiece 606, as seen in FIG. 34. The manifold 662 presents the conically-shaped inlet ports 668 in which to inject the viscoelastic medium. The process is greatly simplified from the previous difficult task of manually applying the viscoelastic medium using a syringe and thin cannula to "paint" the relatively tiny inner surfaces of the nosepiece (cartridge).

Next, the physician engages the inserter 800, with the nosepiece 606 in the load position seen in FIG. 40, with the lens case 670. By simply advancing the nosepiece 606 into the lens case 670 the IOL is transferred into the load chamber 844. Previously, the physician would have to manually remove the IOL from its storage container using forceps and position it in the load chamber. Moreover, the shuttle 632 transfers with the IOL and maintains the trailing haptic 712b in its desirable position over the optic 710. The physician then disengages the inserter 800 from the lens case 670, which can be discarded.

The physician then manipulates the nosepiece 606 from the first, load position to the second, IOL delivery position. This involves movement of the nosepiece 606 in accordance with FIGS. 48A-40D. Simply by disengaging the inserter 800 from the lens case 670, the nosepiece 606 has been slightly retracted away from the handpiece 600 so as to permit rotation. The physician then rotates by 180° the insertion tube 842 so that it points away from the handpiece. Registration of the square pegs 848 on the nosepiece 606 with the square holes 826 on the brackets 612 locks the nosepiece in the second, delivery position with an audible and tactile click.

Finally, the physician positions the insertion tube 842 in the patient's eye, and actuates the inserter as seen in FIGS. 50A-50C. Namely, rotation of the drive cap 630 causes linear movement of the plunger 614, which in turn translates the pushrod 636. The bifurcated tip 640 on the end of the pushrod enters the load chamber 844 and captures the proximal edge of the IOL. The shuttle 732 desirably has a central channel in its underside so that the bifurcated tip 640 easily passes therethrough and captures the end of the IOL.

As described in several embodiments above, the present invention provides an improvement over IOL delivery systems of the prior art in that the IOL is maintained in a relaxed configuration suitable for storage of the intraocular lens then the haptics are manipulated during transfer into the inserter to a configuration that is more suitable for insertion into the eye. Among several embodiments disclosed herein, a shuttle initially provided within the storage case moves at least one haptic relative to the optic during transfer of the lens from the lens case to the inserter, the shuttle being transferred along with the IOL to the inserter. There are a number of other configurations disclosed above, and also numerous others that are contemplated but not described in greater detail herein.

For instance, a lens case may be provided for holding the IOL with telescoping forceps. The IOL includes an optic, a leading haptic, and a trailing haptic arrayed along the axis of movement of the IOL from the lens case into the inserter. By providing segmented forceps with separately movable segments that are independently secured to the leading haptic, the optic body, and the trailing haptic, the IOL can be manipulated during transfer from the lens case to the inserter automatically without manual interference. During storage, the segmented forceps are extended and secure the lens in an unstressed state with the haptics elevated above the anterior surface or below the posterior surface of the optic. By engaging the inserter with the lens case, the forceps are activated by contact and a distal segment holding the leading haptic collapses so as to locate the leading haptic over the edge of the optic. Continued movement of the inserter toward the lens case causes a middle segment of the forceps holding the optic to collapse toward a proximal segment, which holds the trailing end, thus placing the optic underneath the trailing haptic. A plug or other such restraint can then be inserted between the forceps and behind the trailing haptic to scoop the trailing haptic over the optic body and urge the IOL into the cartridge. The plug is designed to restrain the haptics in their manipulated position over the optic and prevents the IOL from resuming its original shape during transfer between the forceps and the inserter. In this sense, the plug functions much like the shuttles described above.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A system for delivering an intraocular lens (IOL) into the eye of a subject, comprising:

an IOL inserter having a handpiece and a nosepiece, the nosepiece having a transfer interface for receiving an IOL, a load chamber open to the transfer interface, and an insertion tube open to the load chamber, the inserter further including a pushrod movable through the nosepiece for urging the IOL from the load chamber and through the insertion tube in a delivery procedure; and a lens case for storing the IOL prior to usage, the lens case comprised of a main body having an open end, a cap that mates over the open end, a transfer port that engages the transfer interface of the nosepiece, and a transfer mechanism coupled to the main body, wherein the transfer mechanism is comprised of a jaw assembly configured to hold the IOL in a fixed location when in a closed configuration and release the IOL when in an open configuration, a haptic folder or shuttle comprised of a leading end configured to engage a haptic and fold it over an optic, and a puller comprised of arms; wherein the cap is comprised of elongated fingers configured to engage the arms of the puller and displace the haptic folder or shuttle upon removal of the cap from the lens case such that the haptic folder or shuttle moves the haptic to its predetermined position relative to the optic; and wherein the transfer interface transfers the IOL from the lens case, through the transfer port, and into the load chamber upon engagement between the lens case and nosepiece, the transfer mechanism further permitting disengagement of the lens case and transfer mechanism from the nosepiece upon IOL transfer therebetween.

2. The system of claim 1, wherein the nosepiece is movable relative to the handpiece between a first position for loading the intraocular lens and a second position for delivering the intraocular lens into the subject's eye.

3. The system of claim 2, wherein the transfer interface of the nosepiece faces away from the handpiece in the first position, and the insertion tube faces away from the handpiece in the second position.

4. The system of claim 3, wherein the nosepiece rotates 180° about the handpiece between the first and second positions.

5. The system of claim 4, wherein the nosepiece includes a pivot shaft moveable between two ends of a slot in the handpiece, and wherein the pivot shaft is positioned at a first end in the first position of the nosepiece and at a second end in the second position of the nosepiece.

6. The system of claim 5, wherein the nosepiece is restrained from rotation about the handpiece when the pivot shaft is positioned at the first end.

7. The system of claim 1, further including a viscoelastic manifold adapted to engage the transfer interface of the nosepiece, the manifold having at least one inlet port leading to internal channels such that a viscoelastic medium injected into the inlet port is guided by the internal channels into the load chamber.

* * * * *